(12) United States Patent
Bertinato et al.

(10) Patent No.: US 7,368,573 B2
(45) Date of Patent: *May 6, 2008

(54) TRIAMIDE-SUBSTITUTED HETEROBICYCLIC COMPOUNDS

(75) Inventors: Peter Bertinato, Old Lyme, CT (US); Michel A. Couturier, Pawcatuck, CT (US); Ernest S. Hamanaka, Gales Ferry, CT (US); Marcus D. Ewing, Colchester, CT (US); Ralph P. Robinson, Gales Ferry, CT (US); Derek L. Tickner, Waterford, CT (US)

(73) Assignee: Pfizer Inc., New York, NY (US)

( * ) Notice: Subject to any disclaimer, the term of this patent is extended or adjusted under 35 U.S.C. 154(b) by 36 days.

This patent is subject to a terminal disclaimer.

(21) Appl. No.: 11/424,488

(22) Filed: Jun. 15, 2006

(65) Prior Publication Data

US 2006/0223851 A1 Oct. 5, 2006

Related U.S. Application Data

(63) Continuation of application No. 11/049,852, filed on Feb. 3, 2005.

(60) Provisional application No. 60/633,763, filed on Dec. 6, 2004, provisional application No. 60/541,678, filed on Feb. 4, 2004.

(51) Int. Cl.
  C07D 215/38 (2006.01)
  C07D 215/46 (2006.01)
  A61K 31/47 (2006.01)
(52) U.S. Cl. .................. 546/162; 546/163; 514/313
(58) Field of Classification Search ................ 546/156, 546/162, 163; 514/312, 313
See application file for complete search history.

(56) References Cited

U.S. PATENT DOCUMENTS

| | | | |
|---|---|---|---|
| 5,712,279 A | 1/1998 | Biller et al. | |
| 5,804,588 A | 9/1998 | Dyke et al. | |
| 5,919,795 A | 7/1999 | Chang et al. | |
| 5,968,950 A | 10/1999 | Quallich et al. | |
| 6,066,653 A | 5/2000 | Gregg et al. | |
| 6,093,732 A | 7/2000 | Tucker et al. | |
| 6,121,282 A | 9/2000 | Dominianni et al. | |
| 6,369,075 B1 | 4/2002 | Ruggeri et al. | |
| 6,492,365 B1 | 12/2002 | Wetterau et al. | |
| 2002/0032238 A1 | 3/2002 | Priepke et al. | 514/616 |
| 2002/0042516 A1 | 4/2002 | Tom et al. | 546/169 |
| 2003/0162788 A1 | 8/2003 | Thomas et al. | 514/252.05 |
| 2005/0234099 A1* | 10/2005 | Bertinato et al. | 514/313 |
| 2007/0093525 A1* | 4/2007 | Bertinato et al. | 514/313 |

FOREIGN PATENT DOCUMENTS

| | | |
|---|---|---|
| EP | 0059983 | 6/1986 |
| EP | 0643057 | 9/1994 |
| EP | 1099438 | 5/2001 |
| EP | 1099701 | 5/2001 |
| EP | 0584446 | 6/2002 |
| EP | 1447402 | 8/2004 |
| WO | WO 95/32948 | 12/1995 |
| WO | WO 96/040640 | 12/1996 |
| WO | WO 9640640 | 12/1996 |
| WO | WO 9743257 | 11/1997 |
| WO | WO 9827979 | 7/1998 |
| WO | WO 99/14196 | 3/1999 |
| WO | WO 0005201 | 2/2000 |
| WO | WO 0228835 | 4/2002 |
| WO | WO 03002533 | 1/2003 |
| WO | WO 03035624 | 5/2003 |
| WO | WO 03072532 | 9/2003 |
| WO | WO 04056775 | 7/2004 |
| WO | WO 04056777 | 7/2004 |

OTHER PUBLICATIONS

Jensen, A.E., et al., Improved nickel-catalyzed cross-coupling reaction conditions between ortho-substituted aryl iodides/nonaflates and alkylzinc iodides in solution and in the solid-phase, *Tetrahedron*, vol. 56: 4197-4201, 2000.
Mathias, L.J., Esterification and alkylation reactions employing Isoureas,*Synthesis*, 561-576, 1979.
Wetterau, J.R., et al., Localization of intracellular triacylglycerol and cholesteryl ester transfer activity in rat tissues, *Biochimica et Biophysica Acta*, vol. 675: 61-617, 1986.
Wetterau, J.R., et al., Absence of microsomal triglyceride transfer protein in individuals with abetalipoproteinemia, *Science*, vol. 258: 999-1001, 1992.
US5804588 equivalent to RU98123074.
US6093732 equivalent to RU2220960.
WO 99/14196 equivalent to EA 002633B1.
WO 96/040640 equivalent to RU 96111018.
WO 95/32948 equivalent to RU2155754.

* cited by examiner

*Primary Examiner*—D. Margaret Seaman
(74) *Attorney, Agent, or Firm*—Gregg C. Benson; Robert M. Kennedy

(57) ABSTRACT

This invention relates to MTP/Apo-B secretion inhibitors of Formula (I)

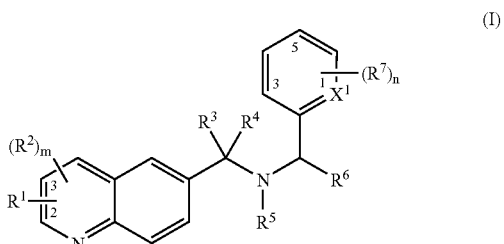

wherein $R^1$-$R^7$, $X^1$, m and n are as defined in the specification, as well as pharmaceutical compositions comprising the compounds, and methods of use of the compounds and compositions. The compounds of the invention are useful in treating obesity and associated diseases, conditions or disorders.

6 Claims, 2 Drawing Sheets

TRIAMIDE-SUBSTITUTED HETEROBICYCLIC COMPOUNDS

CROSS REFERENCE TO RELATED APPLICATIONS

This application is a continuation of pending U.S. patent application Ser. No. 11/049,852 filed on Feb. 3, 2005 which claims the benefit of U.S. Provisional Patent Application Nos. 60/541,678 filed on Feb. 4, 2004 and 60/633,763 filed on Dec. 6, 2004, the disclosures of all of which are incorporated herein by reference in their entirety.

FIELD OF THE INVENTION

This invention relates to substituted quinoline compounds and the use thereof. The present compounds are inhibitors of microsomal triglyceride transfer protein (MTP) and/or apolipoprotein B (Apo B) secretion and are useful, for example for weight management and for the treatment of obesity and associated diseases. These compounds are also useful for the prevention and treatment of atherosclerosis and its clinical sequelae, for lowering serum lipids, and for the prevention and treatment of related diseases. The invention further relates to pharmaceutical compositions comprising these compounds and to methods of treating obesity, atherosclerosis, and related diseases and/or conditions with said compounds, used either alone or in combination with other pharmaceutical agents, including lipid lowering agents. Further still, the invention relates to certain chemical processes and intermediates that are useful in the preparation of the compounds of the present invention.

BACKGROUND OF THE INVENTION

Obesity is a major public health concern because of its increasing prevalence and associated health risks. Moreover, obesity may affect a person's quality of life through limited mobility and decreased physical endurance as well as through social, academic and job discrimination.

Obesity and overweight are generally defined by body mass index (BMI), which is correlated with total body fat and serves as a measure of the risk of certain diseases. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or higher. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Recent studies have found that obesity and its associated health risks are not limited to adults, but also affect children and adolescents to a startling degree. According to the Center for Disease Control, the percentage of children and adolescents who are defined as overweight has more than doubled since the early 1970s, and about 15 percent of children and adolescents are now overweight. Risk factors for heart disease, such as high cholesterol and high blood pressure, occur with increased frequency in overweight children and adolescents compared with normal-weight subjects of similar age. Also, type 2 diabetes, previously considered an adult disease, has increased dramatically in children and adolescents. Overweight conditions and obesity are closely linked to type 2 diabetes. It has recently been estimated that overweight adolescents have a 70% chance of becoming overweight or obese adults. The probability increases to about 80% if at least one parent is overweight or obese. The most immediate consequence of being overweight as perceived by children themselves is social discrimination.

There are possible adverse health consequences of being overweight or obese as such individuals are at increased risk for ailments such as hypertension, dyslipidemia, type 2 (non-insulin dependent) diabetes, insulin resistance, glucose intolerance, hyperinsulinemia, coronary heart disease, angina pectoris, congestive heart failure, stroke, gallstones, cholescystitis, cholelithiasis, gout, osteoarthritis, obstructive sleep apnea and respiratory problems, gall bladder disease, certain forms of cancer (e.g., endometrial, breast, prostate, and colon) and psychological disorders (such as depression, eating disorders, distorted body image and low self esteem) (CDC website, supra). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Currently available prescription drugs for managing obesity generally reduce weight by primarily inducing satiety or decreasing dietary fat absorption. Satiety is achieved by increasing synaptic levels of norepinephdne, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," Obes Res., 3(suppl 4), 415s-7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

Microsomal triglyceride transfer protein catalyzes the transport of triglyceride, cholesteryl ester, and phospholipids and has been implicated as a putative mediator in the assembly of Apo B-containing lipoproteins, which are biomolecules that contribute to the formation of atherosclerotic lesions. Specifically, the subcellular (lumen of the microsomal fraction) and tissue (liver and intestine) distribution of MTP have led to speculation that it plays a role in the assembly of plasma lipoproteins, as these are the sites of plasma lipoprotein assembly. The ability of MTP to catalyze the transport of triglyceride between membranes is consistent with this speculation, and suggests that MTP may catalyze the transport of triglyceride from its site of synthesis in the endoplasmic reticulum membrane to nascent lipoprotein particles within the lumen of the endoplasmic reticulum.

It has been reported that MTP/Apo B secretion inhibitors are useful in reducing food intake in mammals (European patent application publication No. 1 099 438 A2). The use of certain MTP/Apo B secretion inhibitors in the treatment of atherosclerosis and associated diseases including obesity is disclosed in a number of patents. See, for example, U.S. Pat. Nos. 5,919,795; 6,369,075 and 6,121,282.

Compounds which inhibit MTP and/or otherwise inhibit Apo B secretion are accordingly useful in the treatment of atherosclerosis and conditions frequently associated therewith. Such conditions include, for example, hypercholesterolemia, hypertriglyceridemia, pancreatitis, and obesity; and hypercholesterolemia, hypertriglyceridemia, and hyperlipidemia associated with pancreatitis, obesity, and diabetes. For a detailed discussion, see for example, Wetterau et al., Science, 258, 999-1001, (1992), Wetterau et al., Biochem. Biophys. Acta., 875, 610-617 (1986), European patent application/publication Nos. 0 584 446 B1 and 0 643 057 A1, the latter of which refers to certain compounds which have utility as inhibitors of MTP. Other examples of MTP and/or Apo B secretion inhibitors may be found in e.g., U.S. Pat. Nos. 5,712,279; 5,968,950; 6,066,653 and 6,492,365; PCT patent application publication Nos. WO 96/40640, WO 97/43257, WO 98/27979, WO 00/05201, WO 02/28835 and WO 03/002533; and European patent application publication No. 1 099 701 A1.

Although investigations are ongoing, there still exists a need for a more effective and safe therapeutic treatment for reducing or preventing weight-gain.

SUMMARY OF THE INVENTION

The present invention relates to a compound of Formula (I)

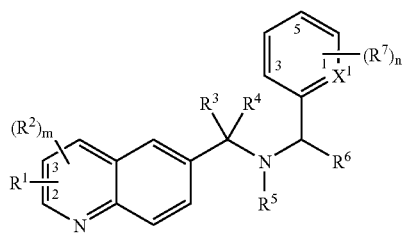

(I)

wherein:
$R^1$ is a group of the formula $R^{1a}$ or $R^{1b}$

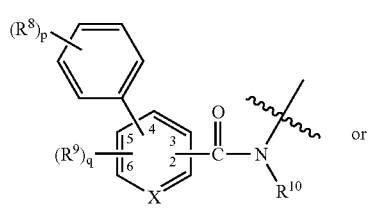

$R^{1a}$ or

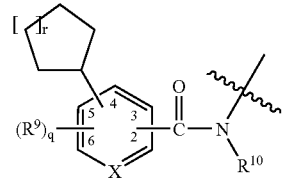

$R^{1b}$ and is attached to the 2 or 3 position of the quinoline group of Formula (I);

m is an integer from 0 to 2;
n is an integer from 0 to 4;
p is an integer from 0 to 5;
q is an integer from 0 to 3;
r is a bond or an integer from 1 to 3;
X is —N— or —C($R^a$)— where $R^a$ is H or $R^9$;
$X^1$ is —N— or —C($R^b$)— where $R^b$ is H or $R^7$;
$R^2$, $R^7$, $R^8$ and $R^9$ are each independently selected from the group consisting of halo, —OH, —CN, ($C_1$-$C_4$)alkyl, ($C_1$-$C_4$)alkoxy-, alkoxyalkyl- having 2 to 4 carbon atoms, halo-substituted($C_1$-$C_4$)alkyl-, halo-substituted($C_1$-$C_4$)alkoxy-, ($C_1$-$C_4$)alkylthio-, hydroxy($C_1$-$C_4$)alkyl-, benzyloxy, ($C_2$-$C_4$)alkenyl, ($C_2$-$C_4$)alkynyl, —C(O)N($R^c$)($R^{11}$), —N($R^{11}$)C(O)$R^{12}$, —N($R^{11}$)CO$_2R^{12}$, —N($R^{11}$)S(O)$_sR^{12}$, —C(O)$R^{12}$, —CO$_2R^{12}$, —OC(O)$R^{12}$, —SO$_2$N($R^c$)($R^{11}$) and —S(O)$_vR^{12}$;

each $R^c$ is independently H or ($C_1$-$C_4$)alkyl;
s is the integer 1 or 2;
v is an integer from 0 to 2;
$R^3$ and $R^4$ are each H or are taken together with the carbon atom to which they are attached to form a carbonyl group;
$R^5$ and $R^{10}$ are each independently selected from the group consisting of H, ($C_1$-$C_4$)alkyl, halo-substituted ($C_1$-$C_4$)alkyl, ($C_3$-$C_7$)cycloalkyl, —C(O)$R^{12}$, alkoxyalkyl- having 2 to 4 carbon atoms, alkylthioalkyl- having 2 to 4 carbon atoms and —SO$_2R^{12}$;
$R^6$ is ($C_1$-$C_{10}$)alkyl optionally substituted with 1 to 3 substituents independently selected from the group consisting of halo, —OH and —CN, or
$R^6$ is pyridyl, phenyl or phenyl($C_1$-$C_6$)alkyl- in which the pyridyl and phenyl group and the phenyl moiety of the phenylalkyl group are optionally substituted with 1 to 3 substituents independently selected from the group consisting of ($C_1$-$C_4$)alkyl, halo-substituted ($C_1$-$C_4$)alkyl, ($C_1$-$C_4$)alkoxy-, halo-substituted ($C_1$-$C_4$)alkoxy-, halo, —OH and —CN, or
R is ($C_2$-$C_{10}$)alkenyl, ($C_2$-$C_{10}$)alkynyl, —CH$_2$N($R^c$)($R^{13}$), —C(O)N(R14)($R^{15}$), —CO$_2R^{20}$ or —CH$_2$— W—Y where W is —O— or —S—; and
Y is selected from the group consisting of H, ($C_1$-$C_8$)alkyl, ($C_3$-$C_7$)cycloalkyl, ($C_3$-$C_7$)cycloalkyl($C_1$-$C_6$)alkyl-, phenyl and phenyl($C_1$-$C_6$)alkyl-, where the ($C_1$-$C_8$)alkyl group is optionally substituted with 1 to 3 substituents independently selected from the group consisting of halo, oxo, —OH, —CN, —CF$_3$, —OCF$_3$, —OR$^{12}$, —C(O)$R^{12}$, —C(O)OR$^{12}$, —OC(O)$R^{12}$, —N($R^{11}$)C(O)$R^{12}$ and —C(O)N($R^c$)($R^{11}$); the ($C_3$-$C_7$)cycloalkyl group and the cycloalkyl moiety of the cycloalkylalkyl group are optionally substituted with 1 to 3 substituents independently selected from the group consisting of halo, oxo, ($C_1$-$C_6$)alkyl, —OH, —CN, —CF$_3$, —OCF$_3$, —C(O)OR$^{12}$ and —OR$^{12}$; and the phenyl group and the phenyl moiety of the phenylalkyl group are optionally substituted with 1 to 3 substituents independently selected from the group consisting of halo, $(C_1-C_6)$alkyl, —OH, —CN, —CF$_3$, —OCF$_3$, —C(O)OR$^{12}$ and —OR$^{12}$;

each R$^{11}$ is independently selected from the group consisting of H, $(C_1-C_4)$alkyl, halo-substituted$(C_1-C_4)$alkyl, $(C_3-C_7)$cycloalkyl, $(C_1-C_3)$alkoxy$(C_2-C_4)$alkyl- having 3 to 5 carbon atoms and $(C_1-C_3)$alkylthio$(C_2-C_4)$alkyl- having 3 to 5 carbon atoms;

each R$^{12}$ is independently $(C_1-C_4)$alkyl or $(C_3-C_7)$cycloalkyl, where the $(C_1-C_4)$alkyl is optionally substituted with 1 to 3 substituents independently selected from the group consisting of $(C_1-C_4)$alkoxy-, halo, —OH, —CN, —CF$_3$ and —OCF$_3$;

R$^{13}$ is selected from the group consisting of $(C_3-C_6)$alkyl, phenylmethyl-, —C(O)R$^{16}$ and —S(O)$_2$R$^{16}$;

R$^{14}$ is selected from the group consisting of H, $(C_1-C_6)$alkyl, $(C_3-C7)$cycloalkyl, $(C_3-C_7)$cycloalkyl$(C_1-C_6)$alkyl-, phenyl and phenyl$(C_1-C_6)$alkyl-, where the $(C_1-C6)$alkyl group is optionally substituted with 1 to 3 substituents independently selected from the group consisting of halo, oxo, —OH, —CN, —CF$_3$, —OCF$_3$, —OR$^{12}$, —C(O)R$^{12}$, —CO$_2$R$^{12}$, —OC(O)R$^{12}$, —N(R$^{11}$)C(O)R$^{12}$ and —C(O)N(R$^c$)(R$^{11}$); the $(C_3-C_7)$cycloalkyl group and the cycloalkyl moiety of the cycloalkylalkyl group are optionally substituted with 1 to 3 substituents independently selected from the group consisting of halo, oxo, $(C_1-C_6)$alkyl, —OH, —CN, —CF$_3$, —OCF$_3$ and —OR$^{12}$; and the phenyl group and the phenyl moiety of the phenylalkyl group are optionally substituted with 1 to 3 substituents independently selected from the group consisting of halo, $(C_1-C_6)$alkyl, $(C_1-C_6)$alkoxy-, —OH, —CN, —CF$_3$, —OCF$_3$ and —OR$^{12}$;

R$^{15}$ is selected from the group consisting of H, $(C_1-C_8)$alkyl, $(C2-C_6)$alkenyl, $(C_2-C_6)$alkynyl, $(C_3-C_7)$cycloalkyl, $(C_3-C_7)$cycloalkyl$(C_1-C_6)$alkyl, phenyl, phenyl$(C_1-C_6)$alkyl-, pyridyl, pyridyl$(C_1-C_6)$alkyl-, —C(O)R$^{12}$ and —SO$_2$R$^{12}$, where the $(C_1-C_8)$alkyl group is optionally substituted with 1 to 3 substituents independently selected from the group consisting of halo, oxo, —OH, —CN, —CF$_3$, —OCF$_3$, —OR$^{12}$, —C(O)R$^{12}$, —C(O)OH, —C(O)OCH$_2$C$_6$H$_5$, —C(O)OCH$_2$C(O)N(R$^c$)(R$^{11}$), —C(O)OR$^{12}$, —OC(O)R$^{12}$, —N(R$^{11}$)C(O)R$^{12}$ and —C(O)N(R$^c$)(R$^{11}$); and the phenyl group and the phenyl moiety of the phenylalkyl group are optionally substituted with 1 to 3 substituents independently selected from the group consisting of halo, $(C_1-C_6)$alkyl, $(C_1-C_6)$alkoxy-, —OH, —CN, —CF$_3$, —OCF$_3$, —OR, —C(O)OH, —C(O)OCH$_2$C$_6$H$_5$, and —C(O)OR$^{12}$; or R$^{15}$ is —(CH$_2$)$_t$N(R$^{17}$)(R$^{18}$) where t is an integer from 2 to 4 and R$^{17}$ and R$^{18}$ are taken together with the nitrogen atom to which they are attached to form a heterocyclic ring containing 3 to 6 ring-atoms in which rings containing 5 or 6 ring-atoms are optionally substituted with oxo and optionally include an additional heteroatom moiety selected from the group consisting of —O—, —S— and —N(R$^{19}$)—; or R$^{14}$ and R$^{15}$ are taken together with the nitrogen atom to which they are attached to form a heterocyclic ring containing 3 to 6 ring-atoms in which rings containing 5 or 6 ring-atoms are optionally substituted with oxo and optionally include an additional heteroatom moiety selected from the group consisting of —O—, —S— and —N(R$^{19}$)—;

R$^{19}$ is H, $(C_1-C_6)$alkyl or halo-substituted$(C_1-C_6)$alkyl;

R$^{16}$ is $(C_1-C_6)$alkyl, phenyl or phenyl$(C_1-C_4)$alkyl-, where the $(C_1-C_6)$alkyl group is optionally substituted with 1 to 3 substituents independently selected from the group consisting of halo, —CN, $(C_1-C_4)$alkoxy- and $(C_1-C_4)$alkylthio, and the phenyl group and the phenyl moiety of the phenylalkyl group are optionally substituted with 1 to 3 substituents independently selected from the group consisting of halo, $(C_1-C_4)$alkyl and $(C_1-C_4)$alkoxy-; and R$^{20}$ is selected from the group consisting of $(C_1-C_6)$alkyl, $(C_3-C_7)$cycloalkyl, $(C_3-C_7)$cycloalkyl$(C_1-C_6)$alkyl-, phenyl and phenyl$(C_1-C_6)$alkyl-, where the $(C_1-C_6)$alkyl group is optionally substituted with 1 to 3 substituents independently selected from the group consisting of halo, oxo, —OH, —CN, —CF$_3$, —OCF$_3$, —OR$^{12}$, —C(O)R$^{12}$, —CO$_2$R$^{12}$, —OC(O)R$^{12}$, —N(R$^{11}$)C(O)R$^{12}$ and —C(O)N(R$^c$)(R$^{11}$); the $(C_3-C_7)$cycloalkyl group and the cycloalkyl moiety of the cycloalkylalkyl group are optionally substituted with 1 to 3 substituents independently selected from the group consisting of halo, oxo, $(C_1-C_6)$alkyl, —OH, —CN, —CF$_3$, -OCF$_3$ and —OR$^{12}$; and the phenyl group and the phenyl moiety of the phenylalkyl group are optionally substituted with 1 to 3 substituents independently selected from the group consisting of halo, $(C_1-C_6)$alkyl, $(C_1-C_6)$alkoxy-, —OH, —CN, —CF$_3$, —OCF$_3$ and —OR$^{12}$;

a pharmaceutically acceptable salt thereof or a prodrug of said compound or said salt.

Preferably X is —C(R$^a$)— and X$^1$ is —N— or —C(R$^b$)—, more preferably X is —C(R$^a$)— and X$^1$ is —C(R$^b$)—. In other aspects of the invention both of X and X$^1$ are —N—, or X is —N— and X$^1$ is —C(R$^b$)—. R$^a$, R$^b$ and R$^c$, independently, are preferably H.

In the numbering system used herein to identify the positioning of substituents on the aromatic rings containing X and/or X$^1$ ring-atoms where reference is made to a structural formula depicting such aromatic ring(s) as containing an X or X$^1$ ring-atom, highest priority is assigned to the X and X$^1$ ring atoms, and they are accordingly each numbered "1" as shown in Formula (I) above. However, the numbering system used in naming specific compounds of the invention in which such aromatic ring(s) is/are phenyl (i.e., X is —C(R$^a$)— and/or X$^1$ is —C(R$^b$)—) is the conventional numbering system for phenyl rings for the ring in which X is —C(R$^a$)— or X$^1$ is —C(R$^b$)—.

In R$^1$, the —C(O)N(R$^{10}$)— moiety is preferably positioned ortho (i.e., adjacent) to the R$^8$-bearing phenyl group or the $(C_4-C_7)$cycloalkyl group in R$^1$, and, when X is —N—, is preferably attached to the 2 or 3 position of the pyridine ring of R$^1$. In this embodiment, the R$^8$-bearing phenyl group or the $(C_4-C_7)$cycloalkyl group is preferably attached to the 2 or 3 position of the pyridyl ring not occupied by —C(O)N(R$^{10}$)—. In a preferred embodiment where X is —N—, the R$^8$-bearing phenyl group or the $(C_4-C_7)$cycloalkyl occupies the 2 position and —C(O)N(R$^{10}$)— occupies the 3 position of the pyridine ring as illustrated in Formula (R$^{1a1}$) and Formula (R$^{1b1}$) below:

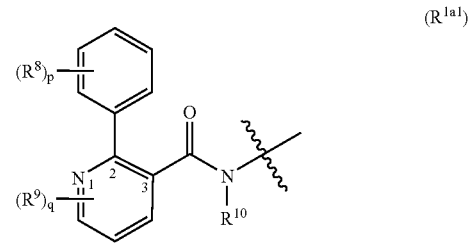

-continued

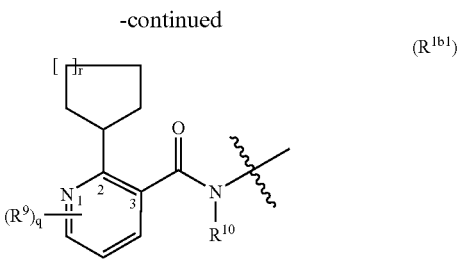
(R$^{1b1}$)

The R$^1$ group is preferably attached to the 2 position of the quinoline group in Formula (I), i.e. ortho to the N atom of the quinoline group.

Preferred embodiments are shown in Formulas (IA) and (IB) below:

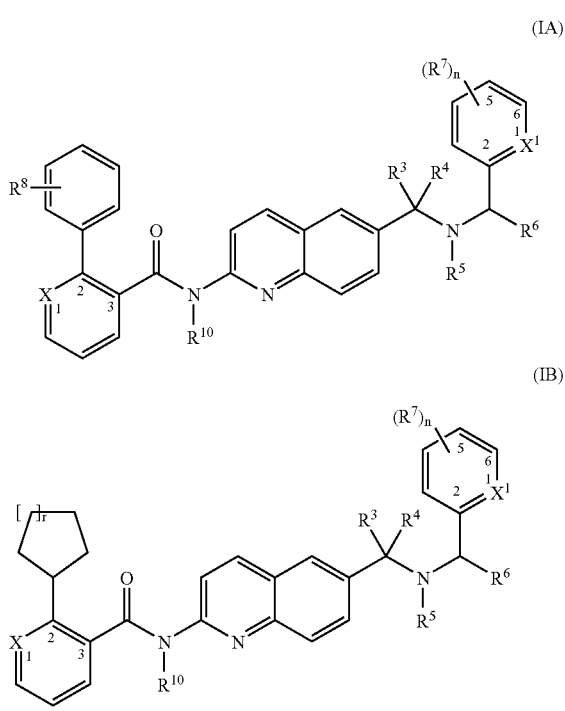

where X, X$^1$, r, R$^3$, R$^4$, R$^5$, R$^6$, R$^7$, R$^8$, R$^{10}$ and n are as defined above, generally and preferably.

The integer r is preferably 1 or 2.

Each R in Formula (I), independently, is preferably selected from the group consisting of F, Cl, —CH$_3$ and —CF$_3$, more preferably from among Cl, —CH$_3$ and —CF$_3$. The integer m is preferably 0 or 1, more preferably 0.

Preferably, each R$^7$ is independently selected from the group consisting of halo, —OH, —CN, (C$_1$-C$_4$)alkyl, (C$_1$-C$_4$)alkoxy-, alkoxyalkyl- having 2 to 4 carbon atoms, halo-substituted(C$_1$-C$_4$)alkyl- and halo-substituted(C$_1$-C$_4$)alkoxy-. More preferably, R$^7$ is selected from the group consisting of from F, Cl, Br, (C$_1$-C$_4$)alkyl, (C$_1$-C$_4$)alkoxy-, fluoro-substituted(C$_1$-C$_4$)alkyl- (e.g., —CF$_3$, —CHF$_2$, —C$_2$F$_5$) and fluoro-substituted(C$_1$-C$_4$)alkoxy- (e.g., —OCF$_3$). Still preferably, R$^7$ is selected from the group consisting of Cl, (C$_1$-C$_4$)alkyl, (C$_1$-C$_4$)alkoxy- and —CF$_3$. Most preferably R$^7$ is selected from the group consisting of Cl, —CH$_3$, —OCH$_3$ and —CF$_3$. The integer n is preferably 0 or 1, more preferably 0. When n is 1, R$^7$ is preferably attached to the 5 or 6 position of the ring in Formula (I).

Each R$^8$, independently, is preferably selected from the group consisting of halo, —OH, (C$_1$-C$_4$)alkyl, (C$_1$-C$_4$)alkoxy-, alkoxyalkyl- having 2 to 4 carbon atoms, halo-substituted(C$_1$-C$_4$)alkyl-, halo-substituted(C$_1$-C$_4$)alkoxy-, benzyloxy, (C$_2$-C$_4$)alkenyl and —S(O)$_v$R$^{12}$; more preferably, from the group consisting of from F, Cl, Br, (C$_1$-C$_4$)alkyl, (C$_1$-C$_4$)alkoxy-, fluoro-substituted(C$_1$-C$_4$)alkyl-, benzyloxy-, —S(O)$_v$R$^{12}$ and fluoro-substituted(C$_1$-C$_4$)alkoxy-. Still more preferably, R$^8$ is selected from the group consisting of Cl, (C$_1$-C$_4$)alkyl, (C$_1$-C$_4$)alkoxy- and —CF$_3$. Still more preferably, R$^8$ is selected from the group consisting of (C$_1$-C$_4$)alkyl, (C$_1$-C$_4$)alkoxy- and —CF$_3$. Still more preferably, R$^8$ is (C$_1$-C$_4$)alkyl or —CF$_3$. Most preferably, R$^8$ is —CH(CH$_3$)$_2$, —C(CH$_3$)$_3$ or —CF$_3$. In a further preferred embodiment R$^8$ is selected from the group consisting of (C$_1$-C$_4$)alkyl (particularly branched chain alkyl such as —CH(CH$_3$)$_2$ or —C(CH$_3$)$_3$), (C$_1$-C$_4$)alkyloxy-, —CF$_3$, benzyloxy-, (C$_2$-C$_4$)alkenyl- (e.g., —C(CH$_3$)=CH$_2$) and —S(O)$_v$R$^{12}$ (e.g., —S(O)$_v$(C$_1$-C$_4$)alkyl such as —SCH$_3$ or —S(O)$_2$CH$_3$)). The integer p is preferably 1 or 2; more preferably, 1. When p is 1, R$^8$ is preferably attached at the 4 position of the phenyl group.

Each R$^9$, independently, is preferably selected from the group consisting of F, Cl, —CH$_3$ and —CF$_3$, more preferably from among Cl, —CH$_3$ and —CF$_3$. Most preferably, R$^9$ is —CH$_3$. The integer q is preferably 0 or 1; more preferably, 0.

R$^5$ and R$^{10}$, independently, are preferably H, (C$_1$-C$_4$)alkyl or halo-substituted(C$_1$-C$_4$)alkyl; more preferably, H, —CH$_3$ or —CF$_3$; most preferably, H or —CH$_3$.

Each R$^{11}$, independently, is preferably selected from the group consisting of H, (C$_1$-C$_4$)alkyl and fluoro-substituted (C$_1$-C$_4$)alkyl-.

Each R$^{12}$, independently, is preferably (C$_1$-C$_4$)alkyl optionally substituted with 1 to 3 substituents independently selected from the group consisting of (C$_1$-C$_4$)alkoxy- and halo (e.g., F or Cl). In one aspect of the invention, the R$^{12}$ (C$_1$-C$_4$)alkyl group is unsubstituted.

Many of the compounds of this invention have one or more chiral carbon atoms. For example, in the compounds of Formula (I), the carbon atom to which R$^6$ is attached will be asymmetric in the majority of the present compounds. The description of specific compounds herein as being "R" or "S" means that the carbon atom to which R$^6$ is attached has the assigned configuration, i.e., "R" or "S", which is determined in accordance with the sequence rules originally described in Cahn R S, Ingold C and Prelog V, *Angew. Chem*. Int. Ed., 5, 385 (1966).

R$^6$ is preferably (C$_1$-C$_{10}$)alkyl, pyridyl, phenyl, phenyl (C$_1$-C$_6$)alkyl-, —CH$_2$—W—Y, —CH$_2$N(R$^c$)(R$^{13}$), —C(O)N(R$^{14}$)(R$^{15}$) or —CO$_2$R$^{20}$ in which the (C$_1$-C$_{10}$)alkyl, pyridyl or the phenyl group or moiety is optionally substituted.

More preferably, R$^6$ is optionally substituted (C$_1$-C$_{10}$) alkyl, optionally substituted pyridyl, —CH$_2$—W—Y, —C(O)N(R$^{14}$)(R$^{15}$) or —CO$_2$R$^{20}$.

Still more preferably, R$^6$ is optionally substituted (C$_1$-C$_{10}$) alkyl, optionally substituted pyridyl, —C(O)N(R$^{14}$)(R$^{15}$) or —CO$_2$R$^{20}$.

Still more preferably, R$^6$ is optionally substituted (C$_1$-C$_{10}$) alkyl, optionally substituted pyridyl or —C(O)N(R$^{14}$)(R$^{15}$).

Still more preferably, R$^6$ is optionally substituted (C$_1$-C$_{10}$) alkyl or —C(O)N(R$^{14}$)(R$^{15}$).

Most preferably, R$^6$ is —C(O)N(R$^{14}$)(R$^{15}$).

Many of the compounds of this invention have one or more chiral carbon atoms. For example, in the compounds of Formula (I), the carbon atom to which $R^6$ is attached will be asymmetric in the majority of the present compounds. The description of specific compounds herein as being "R" or "S" means that the carbon atom to which $R^6$ is attached has the assigned configuration, i.e., "R" or "S", which is determined in accordance with the sequence rules originally described in Cahn R S, Ingold C and Prelog V, *Angew. Chem.* Int. Ed., 5, 385 (1966).

In the embodiment of the invention where $R^6$ is optionally substituted $(C_1-C_{10})$alkyl, the alkyl is preferably a $(C_1-C_8)$ alkyl. Preferably, the alkyl is unsubstituted or is substituted with 1 to 3 substituents independently selected from the group consisting of F and —OH. The substituents $R^3$ and $R^4$ in this embodiment are preferably taken together with the carbon atom to which they are attached to form a carbonyl group. The other substituents and parameters in this embodiment ($R^6$ is optionally substituted $(C_1-C_{10})$alkyl) are as defined above in this application, generally and preferably. Preferred compounds of this embodiment of the invention ($R^6$ is optionally substituted $(C_1-C_{10})$alkyl) include the compounds of Examples 98, 100, 101 and 105 where X and $X^1$ are both —CH—:

Representative compounds of this embodiment of the invention ($R^6$ is optionally substituted $(C_1-C_{10})$alkyl) include the compounds corresponding to those of Examples 98, 100, 101 and 105 except that X is —N— instead of —CH—.

Representative compounds of this embodiment of the invention ($R^6$ is optionally substituted $(C_1-C_{10})$alkyl) include the following compounds corresponding to those of Examples 98, 100, 101 and 105 except that X and $X^1$ are both —N— instead of —CH—.

Representative compounds of this embodiment of the invention ($R^6$ is optionally substituted $(C_1-C_{10})$alkyl) include the following compounds corresponding to those of Examples 98, 100, 101 and 105 except that $X^1$ is —N— instead of —CH—.

In the embodiment where $R^6$ is pyridyl, phenyl or phenyl$(C_1-C_6)$alkyl- in which the pyridyl or the phenyl group or moiety is optionally substituted, the substituents are preferably selected from $(C_1-C_4)$alkyl, halo-substituted $(C_1-C_4)$ alkyl- (e.g., Cl— or F-substituted alkyl- such as —$CH_2CH_2Cl$, —$CF_3$ or —$CHF_2$), $(C_1-C_4)$alkoxy- (e.g., —$OCH_3$, —$OC_2H_5$ or —$OCH(CH_3)_2$), halo (e.g., F or Cl), and OH; more preferably, from $(C_1-C_4)$alkyl, F-substituted $(C_1-C_4)$alkyl-, $(C_1-C_4)$alkoxy-, F and Cl; and most preferably from $(C_1-C_4)$alkyl, —$CF_3$, —$OCH_3$, F and Cl. $R^6$ in this embodiment is preferably pyridyl, particularly 2-pyridyl. The substituents $R^3$ and $R^4$ in this embodiment are preferably taken together with the carbon atom to which they are attached to form a carbonyl group. The other substituents and parameters for this embodiment are as defined above in this application, generally and preferably.

Preferred compounds of this embodiment of the invention ($R^6$ is optionally substituted pyridyl, phenyl or phenyl$(C_1-C_6)$alkyl-) and X and $X^1$ are both —CH— include the compounds of Examples 108, 111 and 112.

Representative compounds of this embodiment of the invention ($R^6$ is optionally substituted pyridyl, phenyl or phenyl$(C_1-C_6)$alkyl-) and X is —N— and $X^1$ is —CH— include the compounds corresponding to those of Examples 108, 111 and 112 except that X is —N— and $X^1$ is —CH—:

In other embodiments of the invention, $R^6$ is $(C_2-C_{10})$ alkenyl or $(C_2-C_{10})$alkynyl, preferably $(C_2-C_8)$alkenyl or $(C_2-C_8)$alkynyl, more preferably $(C_2-C_6)$alkenyl or $(C_2-C_6)$ alkynyl, most preferably $(C_2-C_4)$alkenyl (e.g., allyl) or $(C_2-C_4)$alkynyl (e.g., propargyl).

In the embodiment where $R^6$ is —$CH_2$—W—Y, W is preferably —O—, Y is preferably selected from the group consisting of H. $(C_1-C_6)$alkyl, $(C_3-C_7)$cycloalkyl$(C_1-C_4)$ alkyl-, phenyl and phenyl$(C_1-C_4)$alkyl-; more preferably, from H. $(C_1-C_6)$alkyl, phenyl and phenyl$(C_1-C_4)$alkyl-; most preferably, from H, $(C_1-C_6)$alkyl, phenyl and phenylmethyl-.

The $(C_1-C_6)$alkyl group of Y is unsubstituted or is substituted, preferably with 1 to 3 substituents. In a preferred embodiment, the substituents are independently selected from the group consisting of F. Cl, —$C(O)R^{12}$, —$C(O)OR^{12}$ and —$C(O)N(R^c)(R^{11})$.

The cycloalkyl moiety of the cycloalkylalkyl group of Y is unsubstituted or is substituted, preferably with 1 to 3 substituents. In a preferred embodiment the substituents are independently selected from the group consisting of F, Cl, oxo and $(C_1-C_4)$alkyl.

The phenyl group and the phenyl moiety of the phenylalkyl group of Y are unsubstituted or substituted, preferably with 1 to 3 substituents. In a preferred embodiment, the substituents are independently selected from the group consisting of F, Cl, $(C_1-C_4)$alkyl, —OH, —$CF_3$, —$OCF_3$, —$C(O)OR^{12}$ and —$OR^{12}$; more preferably, from F, Cl, $(C_1-C_4)$alkyl and —$CF_3$.

In this embodiment ($R^6$ is —$CH_2$—W—Y), $R^3$ and $R^4$ are preferably taken together with the carbon atom to which they are attached to form a carbonyl group. The other substituents and parameters are as defined above in this application, generally and preferably.

Preferred compounds of this embodiment of the invention ($R^6$ is —$CH_2$—W—Y) include the compounds of Examples 69-71 where X and $X^1$ are both —CH—:

Representative compounds of this embodiment of the invention ($R^6$ is —$CH_2$—W—Y) include the compounds corresponding to those of Examples 69-71 except that X is —N— instead of —CH—.

Representative compounds of this embodiment of the invention ($R^6$ is —$CH_2$—W—Y) include the compounds corresponding to those of Examples 69-71 except that X and $X^1$ are both —N— instead of —CH—.

Representative compounds of this embodiment of the invention ($R^6$ is —CH2—W—Y) include the compounds corresponding to those of Examples 69-71 except that $X^1$ is —N— instead of —CH—.

In the embodiment where $R^6$ is —$CH_2N(R^c)(R^{13})$, $R^{13}$ is preferably selected from the group consisting of phenylmethyl-, —$C(O)R^{16}$ and —$S(O)_2R^{16}$. More preferably, $R^{13}$ is —$C(O)R^{16}$ or —$S(O)_2R^{16}$; most preferably, —$C(O)R^{16}$.

$R^{16}$ is preferably is $(C_1-C_6)$alkyl, phenyl or phenyl$(C_1-C_4)$alkyl-; more preferably $(C_1-C_6)$alkyl or phenyl.

The $(C_1-C_5)$alkyl group of $R^{16}$ is unsubstituted or is substituted, preferably with 1 to 3 substituents. In a preferred embodiment the substituents are independently selected from the group consisting of F, Cl and $(C_1-C_4)$alkoxy-.

The phenyl group and the phenyl moiety of the phenylalkyl group of $R^{16}$ are unsubstituted or are substituted, preferably with 1 to 3 substituents. In a preferred embodiment the substituents are independently selected from the group consisting of F. Cl, $(C_1-C_4)$alkyl and $(C_1-C_4)$alkoxy-; more preferably, from Cl, —$CH_3$ and —$OCH_3$.

$R^3$ and $R^4$ in this embodiment are preferably taken together with the carbon atom to which they are attached to form a carbonyl group. The other substituents and parameters are as defined above in this application, generally and preferably.

Preferred compounds of this embodiment of the invention ($R^6$ is —$CH_2N(R^c)(R^{13})$) include the compounds of Examples 79, 80 and 82-84 where X and $X^1$ are both —CH—:

Representative compounds of this embodiment of the invention ($R^6$ is —$CH_2N(R^c)(R^{13})$) include the compounds corresponding to those of Examples 79, 80 and 82-84 except that X is —N— instead of —CH—.

Representative compounds of this embodiment of the invention ($R^6$ is —$CH_2N(R^c)(R^{13})$) include the compounds corresponding to those of Examples 79, 80 and 82-84 except that X and $X^1$ are both —N— instead of —CH—.

Representative compounds of this embodiment of the invention ($R^6$ is —$CH_2N(R^c)(R^{13})$) include the compounds corresponding to those of Examples 79, 80 and 82-84 except that $X^1$ is —N— instead of —CH—.

The embodiment where $R^6$ is —$C(O)N(R^{14})(R^{15})$ is a preferred embodiment of the invention.

$R^{14}$ is preferably selected from the group consisting of H, ($C_1$-$C_6$)alkyl, ($C_3$-$C_6$)cycloalkyl, ($C_3$-$C_6$)cycloalkyl($C_1$-$C_4$)alkyl-, phenyl and phenyl($C_1$-$C_4$)alkyl-; more preferably, from H and ($C_1$-$C_4$)alkyl, particularly —$CH_3$ or —$C_2H_5$.

The ($C_1$-$C_6$)alkyl group of $R^{14}$ is optionally substituted, preferably with 1 to 3 substituents. In a preferred embodiment the substituents are independently selected from the group consisting of F, Cl, —OH, —$OCF_3$, and —$OR^{12}$; more preferably, from F, Cl, —OH and —$OCF_3$. Most preferably, the optional substituent is F.

The cycloalkyl group and the cycloalkyl moiety of the cycloalkylalkyl group of $R^{14}$ are optionally substituted, preferably with 1 to 3 substituents. In a preferred embodiment the substituents are independently selected from the group consisting of F, Cl, oxo, ($C_1$-$C_4$)alkyl, —OH, —$CF_3$, —$OCF_3$ and —$OR^{12}$; more preferably, from F, Cl, oxo and ($C_1$-$C_4$)alkyl.

The phenyl group and the phenyl moiety of the phenylalkyl group of $R^{14}$ are optionally substituted, preferably with 1 to 3 substituents. In a preferred embodiment the substituents are independently selected from the group consisting of F, Cl, ($C_1$-$C_4$)alkyl, ($C_1$-$C_4$)alkoxy, —OH, —$CF_3$, —$OCF_3$ and —$OR^{12}$; more preferably, from F, Cl, ($C_1$-$C_4$)alkyl and ($C_1$-$C_4$)alkoxy-; most preferably, from Cl, —$CH_3$ and —$OCH_3$.

$R^{15}$ is preferably selected from the group consisting of H, ($C_1$-$C_8$)alkyl (particularly n-pentyl), ($C_3$-$C_7$)cycloalkyl, ($C_3$-$C_7$)cycloalkyl($C_1$-$C_6$)alkyl-, phenyl, phenyl($C_1$-$C_6$)alkyl-, pyridyl, pyridyl($C_{1-C6}$)alkyl-, —$C(O)R^{12}$, —$SO_2R^{12}$ and —$(CH_2)_rN(R^{17})(R^{18})$; more preferably, from H, ($C_1$-$C_8$)alkyl, ($C_3$-$C_6$)cycloalkyl, ($C_3$-$C_6$)cycloalkyl($C_1$-$C_6$)alkyl-, phenyl, phenyl($C_1$-$C_6$)alkyl-, pyridyl an pyridyl($C_1$-$C_6$)alkyl-. Still more preferably, $R^{15}$ is selected from the group consisting of H, ($C_1$-$C_8$)alkyl, ($C_3$-$C_8$)cycloalkyl, ($C_3$-$C_6$)cycloalkyl($C_1$-$C_6$)alkyl-, phenyl($C_1$-$C_6$)alkyl-, pyridyl and pyridyl($C_1$-$C_6$)alkyl-. Still more preferably, $R^{15}$ is selected from the group consisting of H, ($C_1$-$C_8$)alkyl, ($C_3$-$C_6$)cycloalkyl, ($C_3$-$C_6$)cycloalkyl($C_1$-$C_4$)alkyl-, phenyl ($C_1$-$C_4$)alkyl- and pyridyl($C_1$-$C_4$)alkyl- (e.g., pyridylmethyl such as 2-pyridylmethyl). Most preferably, $R^{15}$ is H, optionally substituted phenyl($C_1$-$C_4$)alkyl- (e.g., optionally substituted benzyl) or optionally substituted ($C_1$-$C_8$)alkyl.

The ($C_1$-$C_8$)alkyl group of $R^{15}$ is preferably unsubstituted or it may be substituted, preferably with 1 to 3 substituents. Substituted alkyl for $R^{15}$ includes, for example, groups such as —($C_1$-$C_8$)alkyl$CO_2$H and various esters thereof (e.g., —($CH_2)_2CO_2CH_3$).In a preferred embodiment the substituents are independently selected from the group consisting of F, Cl, oxo, —C(O)OH, —$C(O)OCH_2C_6H_5$, —$C(O)OCH_2C(O)N(R^c)(R^{11})$, —$C(O)OR^{12}$, —OH, —$OCF_3$, and —$OR^{12}$; more preferably, from F, Cl, oxo, —OH and —$OCF_3$; most preferably, from F, oxo, —OH and —$OCF_3$.

The phenyl group and the phenyl moiety of the phenylalkyl group of $R^{15}$ are unsubstituted or are substituted, preferably with 1 to 3 substituents. In a preferred embodiment the substituents are independently selected from the group consisting of F, Cl, ($C_1$-$C_4$)alkyl, ($C_1$-$C_4$)alkoxy-, —OH, —CN, —$CF_3$, —$OCF_3$, —C(O)OH, —$C(O)OCH_2C_6H_5$, and —$C(O)OR^{12}$, more preferably from F, Cl, ($C_1$-$C_4$)alkyl, ($C_1$-$C_4$)alkoxy-, —OH, —$CF_3$, —$OCF_3$, —$C(O)OCH_2C_6H_5$, and —$C(O)OR^{12}$. In a preferred embodiment, the phenylalkyl group of $R^{15}$ is unsubstituted benzyl or a fluoro-substituted benzyl, particularly 4-F-benzyl.

When $R^{15}$ is —$(CH_2)_rN(R^{17})(R^{18})$, and $R^{17}$ and $R^{18}$ are taken together with the nitrogen atom to which they are attached to form an optionally substituted heterocyclic ring containing 5 or 6 ring-atoms and optionally including an additional heteroatom moiety, the additional heteroatom moiety is preferably —O— or —$N(R^{11})$—, where $R^{19}$ is preferably ($C_1$-$C_4$)alkyl or F-substituted($C_1$-$C_4$)alkyl- (e.g., —$CF_3$ or —$CHF_2$); more preferably, ($C_1$-$C_4$)alkyl.

Alternatively, in another preferred embodiment, $R^{14}$ and $R^{15}$ are taken together with the nitrogen atom to which they are attached to form a heterocyclic ring containing 3 to 6 ring-atoms (preferably 5 or 6) in which rings containing 5 or 6 ring-atoms are optionally substituted with oxo and optionally include an additional heteroatom moiety. Preferably, the additional heteroatom moiety is —O— or —$N(R^{19})$—, where $R^{19}$ is preferably ($C_1$-$C_4$)alkyl or F-substituted($C_1$-$C_4$)alkyl- (e.g., —$CF_3$ or —$CHF_2$); more preferably, ($C_1$-$C_4$)alkyl. The additional heteroatom moiety is more preferably —O—.

In this embodiment, where $R^6$ is —$C(O)N(R^{14})(R^{15})$, $R^3$ and $R^4$ are preferably taken together with the carbon atom to which they are attached to form a carbonyl group. The other substituents and parameters are as defined above in this application, generally and preferably.

Preferred compounds of this embodiment of the invention ($R^6$ is —$C(O)N(R^{14})(R^{15})$), where X and $X^1$ are both —CH—, include the compounds of Examples 1-7, 9-12,16-21, 25, 26, 30-32, 34, 35, 47-55 and 58-64.

A particularly preferred compound of this embodiment is:
(S)-2-[(4'-trifluoromethyl-biphenyl-2-carbonyl)-amino]-quinoline-6-carboxylic acid (pentylcarbamoyl-phenylmethyl)-amide, the compound of Example 1.

The following two compounds, where X and $X^1$ are both —CH—, are also of particular interest:
(S)-2-[(4'-trifluoromethyl-biphenyl-2-carbonyl)-amino]-quinoline-6-carboxylic acid [(4-hydroxy-pentylcarbamoyl)-phenyl-methyl]-amide and
(S)-2-[(4'-trifluoromethyl-biphenyl-2-carbonyl)-amino]-quinoline-6-carboxylic acid [(4-oxo-pentylcarbamoyl)-phenyl-methyl]-amide.

Representative compounds of this embodiment of the invention (where $R^6$ is —$O)N(R^{14})(R^5)$) include the compounds corresponding to those of Examples 1-7, 9-12, 16-21, 25, 26, 30-32, 34, 35, 47-55 and 58-64 except that X is —N— instead of —CH—.

Representative compounds of this embodiment of the invention (where $R^6$ is —$C(O)N(R^{14})(R^{15})$) include the compounds corresponding to those of Examples 1-7, 9-12, 16-21, 25, 26, 30-32, 34, 35, 47-55 and 58-64 except that X and $X^1$ are both —N— instead of —CH—.

Representative compounds of this embodiment of the invention (where $R^6$ is —C(O)N($R^{14}$)($R^{15}$)) include the compounds corresponding to those of Examples 1-7, 9-12, 16-21, 25, 26, 30-32, 34, 35, 47-55 and 58-64 except that $X^1$ is —N— instead of —CH—.

The embodiment where $R^6$ is —$CO_2R^{20}$ is also a preferred embodiment of the invention.

$R^{20}$ is preferably selected from the group consisting of ($C_1$-$C_6$)alkyl, ($C_5$-$C_7$)cycloalkyl, ($C_5$-$C_7$)cycloalkyl($C_1$-$C_4$)alkyl-, phenyl and phenyl($C_1$-$C_4$)alkyl-; more preferably, from ($C_1$-$C_6$)alkyl.

The ($C_1$-$C_6$)alkyl group of $R^{20}$ is unsubstituted or is substituted, preferably with 1 to 3 substituents. In a preferred embodiment, the substituents are independently selected from the group consisting of halo, oxo, —OH, —$OCF_3$, —$OR^{12}$, —C(O)$R^{12}$, —$CO_2R^{12}$, —OC(O)$R^{12}$, —N($R^{11}$)C(O)$R^{12}$ and —C(O)N($R^c$)($R^{11}$); more preferably, from halo, OH, —C(O)$R^{12}$, —$CO_2R^{12}$ and —OC(O)$R^{12}$; most preferably, from F, Cl, —OH and —C(O)$R^{12}$.

The cycloalkyl group and the cycloalkyl moiety of the cycloalkylalkyl group of $R^{20}$ are unsubstituted or are substituted, preferably with 1 to 3 substituents. In a preferred embodiment, the substituents are independently selected from the group consisting of halo, oxo, ($C_1$-$C_4$)alkyl, —OH, —$CF_3$, —$OCF_3$ and —$OR^{12}$; more preferably, from halo (e.g., F or Cl), oxo, ($C_1$-$C_4$)alkyl and —$CF_3$.

The phenyl group and the phenyl moiety of the phenylalkyl group of $R^{20}$ are unsubstituted or are substituted, preferably with 1 to 3 substituents. In a preferred embodiment the substituents are independently selected from the group consisting of halo, ($C_1$-$C_6$)alkyl, ($C_1$-$C_6$)alkoxy-, —OH, —$CF_3$, —$OCF_3$ and —$OR^{12}$; more preferably, from halo (e.g., F or Cl), ($C_1$-$C_6$)alkyl, ($C_1$-$C_4$)alkoxy and —$CF_3$.

$R^3$ and $R^4$ in this embodiment are preferably taken together with the carbon atom to which they are attached to form a carbonyl group. The other substituents and parameters are as defined above in this application, generally and preferably.

Representative compounds of this embodiment of the invention, where $R^6$ is —$CO_2R^{20}$, are (S)-phenyl-({2-[(4'-trifluoromethyl-biphenyl-2-carbonyl)-amino]-quinoline-6-carbonyl}-amino)-acetic acid methyl ester and the corresponding ethyl, n-propyl, isopropyl, n-butyl, isobutyl, s-butyl, t-butyl, n-pentyl, isopentyl, neopentyl, t-pentyl, n-hexyl, isohexyl, neohexyl and t-hexyl esters; particularly the methyl, ethyl, n-propyl, isopropyl, n-butyl, t-butyl, n-pentyl and n-hexyl esters where X and X' are both —CH—.

Representative compounds of this embodiment of the invention, where $R^6$ is —$CO_2R^{20}$, include the following compounds where X is —N— and $X^1$ is —CH—:

(S)-phenyl-[(2-{[2-(4-trifluoromethyl-phenyl)-pyridine-3-carbonyl]-amino}-quinoline-6-carbonyl])-amino]-acetic acid methyl ester and the corresponding ethyl, n-propyl, isopropyl, n-butyl, isobutyl, s-butyl, t-butyl, n-pentyl, isopentyl, neopentyl, t-pentyl, n-hexyl, isohexyl, neohexyl and t-hexyl esters; particularly the methyl, ethyl, n-propyl, isopropyl, n-butyl, t-butyl, n-pentyl and n-hexyl esters.

Representative compounds of this embodiment of the invention ($R^6$ is —$CO_2R^{20}$), where X and $X^1$ are both —CH—, are the compound of Example 113 and the corresponding ethyl, n-propyl, isopropyl, n-butyl, isobutyl, s-butyl, t-butyl, n-pentyl, isopentyl, neopentyl, t-pentyl, n-hexyl, isohexyl, neohexyl and t-hexyl esters; particularly the methyl, ethyl, n-propyl, isopropyl, n-butyl, t-butyl, n-pentyl and n-hexyl esters.

Representative compounds of this embodiment of the invention, where $R^6$ is —$CO2R^{20}$, include the following compounds where X is —CH— and $X^1$ is —N—:

(S)-pyridin-2-yl-({2-[(4'-trifluoromethyl-biphenyl-2-carbonyl)-amino]-quinoline-6-carbonyl}-amino)-acetic acid methyl ester and the corresponding ethyl, n-propyl, isopropyl, n-butyl, isobutyl, s-butyl, t-butyl, n-pentyl, isopentyl, neopentyl, t-pentyl, n-hexyl, isohexyl, neohexyl and t-hexyl esters; particularly the methyl, ethyl, n-propyl, isopropyl, n-butyl, t-butyl, n-pentyl and n-hexyl esters.

Additional preferred compounds of the invention include the compounds of Examples 39, 40, 42-46, 114, 115, 117, 119-122, 124-126, 128, 130-144, 146-150, 152, 155, 157, 160-169, 171-174, 176, 177, 189-196 198-200, 202-208 210, 211 and 213-215.

A preferred embodiment of the invention pertains to compounds of Formula (IA-1).

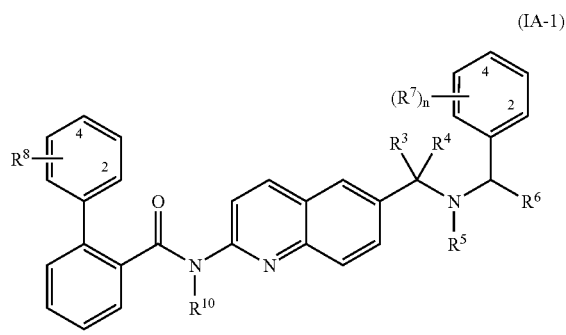

(IA-1)

wherein $R^3$, $R^4$, $R^5$, $R^6$, $R^7$, $R^8$, $R^{10}$ and n are as defined above, generally and preferably. The $R^8$ substituent is preferably positioned at C-4 of the phenyl ring.

Another preferred embodiment of the invention pertains to compounds of Formula (IA-1a)

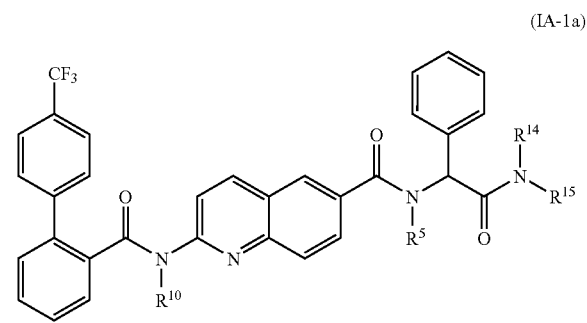

(IA-1a)

wherein $R^5$, $R^{10}$, $R^{14}$ and $R^{15}$ are as defined above, generally and preferably. In these embodiments the carbon atom to which —C(O)N($R^{14}$)($R^{15}$) is attached preferably has the (S) configuration. R/S mixtures, e.g., racemic mixtures, are also preferred.

A further preferred embodiment of the invention pertains to compounds of Formula (IA-1b)

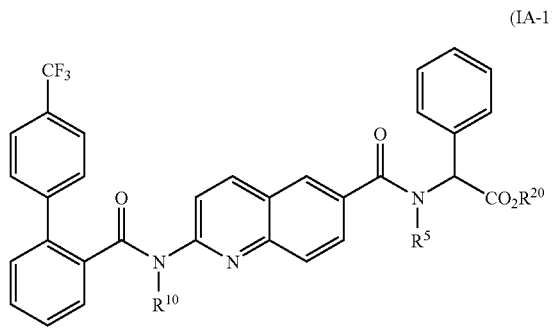

(IA-1b)

wherein $R^5$, $R^{10}$ and $R^{20}$ are as defined above, generally and preferably.

A further preferred embodiment of the invention pertains to compounds of Formula (IA-1c)

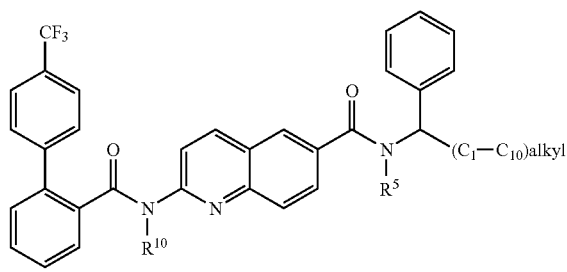

(IA-1c)

wherein the $(C_1-C_{10})$alkyl is optionally substituted and $R^5$ and $R^{10}$ are as defined above, generally and preferably. In these embodiments the carbon atom to which $—(C_1-C_{10})$alkyl is attached preferably has the (R) configuration. R/S mixtures, e.g., racemic mixtures, are also preferred.

Compounds corresponding to the compounds of Formulas (IA-1a), (IA-1b) and (IA-1c) in which $R^8$ is $(C_1-C_4)$alkyl instead of $—CF_3$ are also preferred embodiments.

The invention also relates to polymorphic forms of the compounds of the invention; in particular to polymorphs of (S)-2-[(4'-trifluoromethyl-biphenyl-2-carbonyl)-amino]-quinoline-6-carboxylic acid (pentylcarbamoyl-phenyl-methylamide, which is the (S) isomer of the compound of Formula (IA-1a) wherein $R^5$, $R^{10}$ and $R^{14}$ are H and $R^{15}$ is $—(CH_2)_4CH_3$. More specifically, the present invention provides crystalline Forms A and B of (S)-2-[(4'-trifluoromethyl-biphenyl-2-carbonyl)-amino]-quinoline-6-carboxylic acid (pentylcarbamoyl-phenyl-methyl)-amide having X-ray powder diffraction patterns substantially the same as shown in FIGS. 1 and 2 respectively. It is to be understood that some level of noise is inherent in the generation of a diffraction pattern, i.e., peaks in intensity are to be discriminated from background according to methods well-known in the art. In a preferred embodiment, the X-ray powder diffraction pattern for Form A is substantially the same as that shown in FIG. 1. In a more preferred embodiment, Form A has an X-ray powder diffraction pattern having peaks at 2-theta values substantially the same as the 2-theta values for at least ten of the peaks of highest intensity in the X-ray powder diffraction pattern shown in FIG. 1.

Another aspect of this invention pertains to the compounds of Formulas (D), (F) and (D-G) which are intermediates useful in the preparation of compounds of Formula (I).

Formula (D-$G_1$) represents a preferred subgenus of Formulas (D-G). $R^5$, $R^6$, $R^7$, $X^1$ and n are as defined above, generally and preferably. In a preferred embodiment, $R^6$ is $(C_1-C_8)$alkyl, 2-pyridyl or $—C(O)N(R^{14})(R^{15})$ in which $R^{14}$ is H, $—CH_3$ or $—C_2H_5$) and $R^{15}$ is $(C_1-C_8)$alkyl, benzyl or a fluorinated benzyl such as 4-fluorobenzyl.

The $—OR^{21}$ moiety in (F) is $—OH$ or any leaving group that is displaceable with $—OH$ under routine conditions of acid- or base-catalyzed hydrolysis. $R^{21}$ may also be a cation, for example of an alkali metal, such as $K(^+)$. Typically, $R^{21}$ will be H, an alkyl group, preferably of 1 to 4 carbon atoms (e.g., $—CH_3$, $—CH(CH_3)_2$, $—CH_2)_2CH_3$, or $—C(CH_3)_3$), phenyl, a phenylalkyl group of 1 to 4 alkyl carbon atoms, e.g., benzyl, or a cation. Preferably, $R^{21}$ is H, $(C_1-C_4)$alkyl, benzyl or a cation. $R^2$, $R^8$, $R^9$, $R^{10}$, X, m, p, and q are as defined above, generally and preferably.

Formula (F-1) represents a preferred subgenus of Formula (F) and Formula (F-1') represents a preferred subgenus of Formula (F-1). In a preferred embodiment, $R^{10}$ in (F), (F-1), (F-1') is H or $—CH_3$; more preferably, H. In a further preferred embodiment, $R^8$ is $—CF_3$ or $(C_1-C_4)$alkyl. Other intermediates of particular interest of the present invention include compounds which are the same as the compounds of Formulas (F), (F-1) and (F-1') except that they have a $(C_4-C_7)$cycloalkyl group in place of the $R^8$-bearing phenyl group.

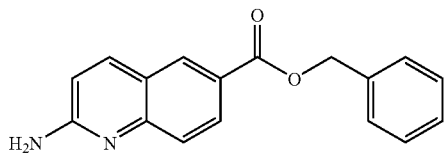

(D)

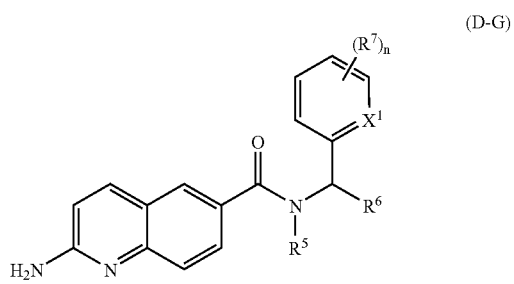

(D-G)

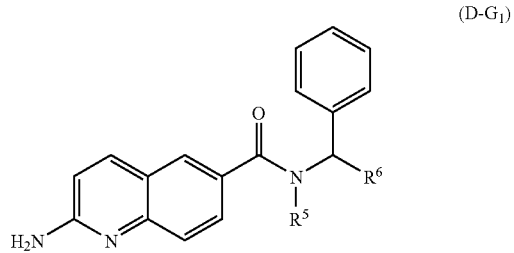

(D-$G_1$)

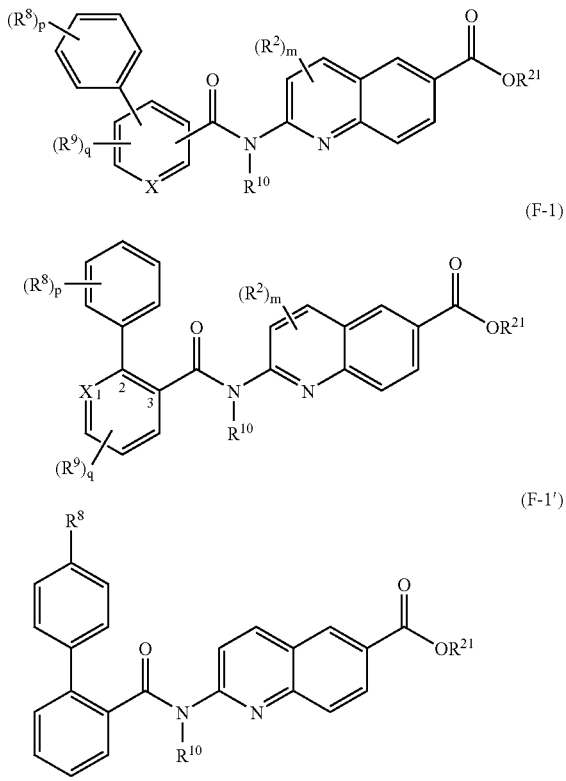

This invention also relates to the salts, solvates and hydrates of the compounds of the invention. The compounds and intermediates of the invention that are basic in nature are capable of forming a wide variety of salts with various inorganic and organic acids. The acids that may be used to prepare pharmaceutically acceptable acid addition salts of such compounds of the are those that form non-toxic acid addition salts, i.e. salts containing pharmacologically acceptable anions. Certain of the intermediates of the invention are acidic in nature and are capable of forming salts with various bases. Sodium and potassium salts are preferred.

The present invention also relates to prodrugs of the present compounds. Compounds of Formula (I) having free amino or hydroxy groups can be converted into, for example, esters or amides, that are reconvertable in vivo to the underivatized compounds of Formula (I).

In another embodiment of the invention, a pharmaceutical composition is provided which comprises a compound of Formula (I). In a further embodiment the composition also comprises at least one additional pharmaceutical agent, which is preferably an antihypertensive agent, an anti-inflammatory agent, a lipid-lowering agent, a cholesterol-lowering agent, an antidiabetes agent or an anti-obesity agent.

Also provided is a method of treating obesity in an animal in need of such treatment, which comprises administering to the animal a therapeutically effective amount of a compound of Formula (I), a pharmaceutically acceptable salt thereof, or a solvate or hydrate of said compound or said salt. In a further embodiment the method further comprises administering said compound of Formula (I), a pharmaceutically acceptable salt thereof, or a solvate or hydrate of said compound or said salt in combination with at least one additional pharmaceutical agent, preferably another anti-obesity agent.

Also provided is a method of treating obesity in an animal in need of such treatment which comprises administering to the animal a therapuetically effective amount of an intestinal-selective MTP inhibitor compound of Formula (I). Preferably, the $ED_{25}$ of a compound of Formula (I) for the inhibition of intestinal fat absorption is at least 5-fold lower than the $ED_{25}$ of the compound for the lowering of serum triglycerides. More preferably, the $ED_{25}$ for the inhibition of intestinal fat absorption is at least 10-fold lower than the $ED_{25}$ of the compound for the lowering of serum triglycerides. Still more preferably, the compound exhibits an $ED_{25}$ for the inhibition of intestinal fat absorption which is at least 50-fold lower than the $ED_{25}$ of the compound for the lowering of serum triglycerides.

As used herein, the term "selectivity" or "selective" refers to a greater effect of a compound in a first assay, compared to the effect of the same compound in a second assay. In the present invention, the first assay is for the ability of the compound to inhibit intestinal fat absorption and the second assay is for the ability of the compound to lower serum triglycerides. In a preferred embodiment, the ability of the compound to inhibit intestinal fat absorption is measured by the $ED_{25}$ of the compound in an intestinal fat absorption assay, such that a greater effect of the compound results in the observation of a lower absolute (numerical) value for the $ED_{25}$. In another preferred embodiment, the ability of the compound to lower serum triglycerides is measured by the $ED_{25}$ of the compound in a serum triglyceride assay. Again, a greater effect of a compound in the serum triglyceride-lowering assay results in the observation of a lower absolute (numerical) value for the $ED_{25}$. An illustrative example of each assay is provided hereinbelow, but it is to be understood that any assay capable of measuring the effectiveness of a compound in inhibiting intestinal fat absorption, or capable of measuring the effectiveness of a compound in lowering serum triglycerides, is encompassed by the present invention.

In a preferred embodiment, the intestinal-selective MTP inhibitor compound is a compound of Formula (IA-1a), wherein $R^5$, $R^{10}$, $R^{14}$ and $R^{15}$ are as defined above, generally and preferably, and the carbon atom to which the —$C_6H_5$ is attached has the (S) configuration. More preferably, the intestinal-selective MTP inhibitor compound is (S)-2-[(4'-trifluoromethyl-biphenyl-2-carbonyl)-amino]-quinoline-6-carboxylic acid (pentylcarbamoyl-phenyl-methyl)-amide.

Also provided is a method of weight control in an animal which comprises administering to the animal a weight-controlling amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

The present invention also provides a method of reducing food intake in an animal which comprises administering to the animal a food-intake-reducing amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

Also provided is a method of causing reduced fat absorption in an animal which comprises administering to the animal a fat-absorption-reducing amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

Also provided is a method of treating atherosclerosis, pancreatitis secondary to hypertriglyceridemia or hyperglycemia in an animal in need of such treatment, which comprises administering to the animal a therapeutically effective amount of the compound of Formula (I), a pharmaceutically acceptable salt thereof, or a solvate or hydrate of said compound or said salt. The compound of Formula (I) may be used alone or in combination with at least one additional pharmaceutical agent, preferably one that is useful in treating atherosclerosis, pancreatitis secondary to hypertriglyceridemia or hyperglycemia.

Also provided is a method of treating atherosclerosis, pancreatitis secondary to hypertriglyceridemia or hyperglycemia (1) by causing a reduced absorption of dietary fat through MTP inhibition, (2) by lowering triglycerides through MTP inhibition or (3) by decreasing the absorption of free fatty acids through MTP inhibition; in an animal in need of such treatment, which comprises administering to the animal a therapeutically effective amount of the compound of Formula (I), a pharmaceutically acceptable salt thereof, or a solvate or hydrate of said compound or said salt. The compound of Formula (I) may be used alone or in combination with at least one additional pharmaceutical agent, preferably one that is useful in treating atherosclerosis, pancreatitis secondary to hypertriglyceridemia or hyperglycemia.

Also provided is a method of treating diabetes, including impaired glucose tolerance, insulin resistance, insulin dependent diabetes mellitus (Type I) and non-insulin dependent diabetes mellitus (NIDDM or Type II), which comprises administering to the animal a therapeutically effective amount of a compound of Formula (I), a pharmaceutically acceptable salt thereof, or a solvate or hydrate of said compound or said salt. The compound of Formula (I) may be used alone or in combination with at least one additional pharmaceutical agent, preferably one that is useful in treating diabetes. In a preferred embodiment the diabetes is Type II diabetes. In another preferred embodiment the animal is a human. In a further preferred embodiment the animal is feline, preferably a cat.

A further aspect of the present invention pertains to a pharmaceutical kit for use by a consumer in the treatment or prevention of obesity, atherosclerosis, pancreatitis secondary to hypertriglyceridemia or hyperglycemia. The kit comprises (a) a suitable dosage form comprising a compound of Formula (I); and (b) instructions describing a method of using the dosage form to treat or prevent obesity, atherosclerosis, pancreatitis secondary to hypertriglyceridemia or hyperglycemia.

Another embodiment of the present invention relates to a pharmaceutical kit comprising: (a) a first pharmaceutical composition comprising a compound of Formula (I), (b) a second pharmaceutical composition comprising a second compound useful for the treatment or prevention of obesity, atherosclerosis, pancreatitis secondary to hypertriglyceridemia or hyperglycemia; and (c) a container for containing the first and second compositions.

Definitions

As used herein, the term "alkyl" refers to a straight- or branched-chain hydrocarbon radical of the general formula $C_nH_{2n+1}$. For example, the term "$(C_1$-$C_6)$alkyl" refers to a monovalent, straight- or branched-chain, saturated aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion of any group, e.g., an alkoxy, acyl, alkylamino, dialkylamino, or alkylthio group, has the same meaning as above.

"Halo-substituted alkyl" refers to an alkyl group substituted with one or more halogen atoms (e.g., —$CH_2Cl$, —$CHF_2$, —$CF_3$, —$C_2F_5$, and the like). Likewise, "fluoro-substituted alkyl" means the alkyl group is substituted with one or more fluorine atoms.

The term "acyl" refers to alkyl-, partially saturated or fully saturated cycloalkyl-, partially saturated or fully saturated heterocycle-, aryl-, and heteroaryl-substituted carbonyl groups. For example, acyl includes groups such as $(C_1$-$C_6)$ alkanoyl, $(C_3$-$C_6)$cycloalkylcarbonyl, heterocyclecarbonyl, aroyl (e.g., benzoyl) and heteroaroyl.

The term "substituted", as used herein to modify a group or moiety, means, unless otherwise specified, that the group or moiety is substituted with one or more substituents that are commonly used in medicinal chemistry for such a group or moiety.

The term "halo" means F, Cl, Br or I. Preferably, halo will be F, Cl or Br; more preferably, F or Cl.

The term "solvate" refers to a molecular complex of a compound represented by Formula (I) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The phrase "pharmaceutically acceptable" indicates that the substance or composition must be compatible chemically and/or toxicologically, with the other ingredients comprising a formulation, and/or the mammal being treated therewith.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent that blocks or protects the carboxy functionality such as an ester group. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino) ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii)

prevents or delays the onset of one or more symptoms of the particular disease, condition, or disorder described herein.

The term "animal" means humans as well as all other warm-blooded members of the animal kingdom possessed of a homeostatic mechanism, including mammals (e.g., companion animals, zoo animals and food-source animals) and birds. Some examples of companion animals are canines (e.g., dogs), felines (e.g., cats) and horses; some examples of food-source animals are pigs, cows, sheep, poultry and the like. Preferably, the animal is a mammal. Preferably, the mammal is a human, a companion animal or a food-source animal. Most preferably, the animal is a human.

The terms "treating", "treat", or "treatment" embrace both preventative, i.e. prophylactic, and palliative treatment.

The term "compounds of the present invention" (unless specifically identified otherwise) refer to compounds of Formulas (I), including the compounds of Formulas (IA), (IA-1), (IA-1a), (IA-1b) and (IA-1c), as defined above generally and preferably, prodrugs thereof, pharmaceutically acceptable salts of the compounds and/or prodrugs, and hydrates or solvates of the compounds, salts, and/or prodrugs, as well as all stereoisomers, tautomers and isotopically labeled compounds.

BRIEF DESCRIPTION OF THE DRAWINGS

FIG. (1) shows the x-ray diffraction pattern of a sample of crystalline Form A of the title compound of Example (1). The sample was prepared as described in Example (1c).

FIG. (2) shows the x-ray diffraction pattern of a sample of crystalline Form B of the title compound of Example (1). The sample was prepared as described in Example (1d).

Figure 1:
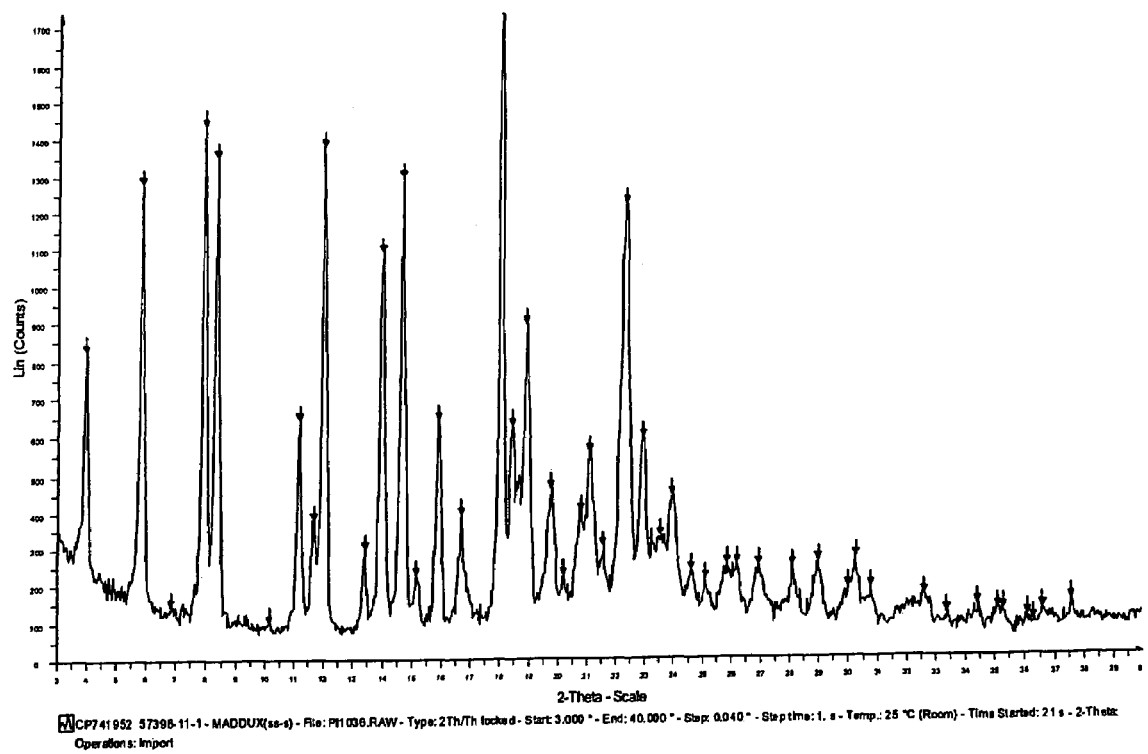
Figure 2:
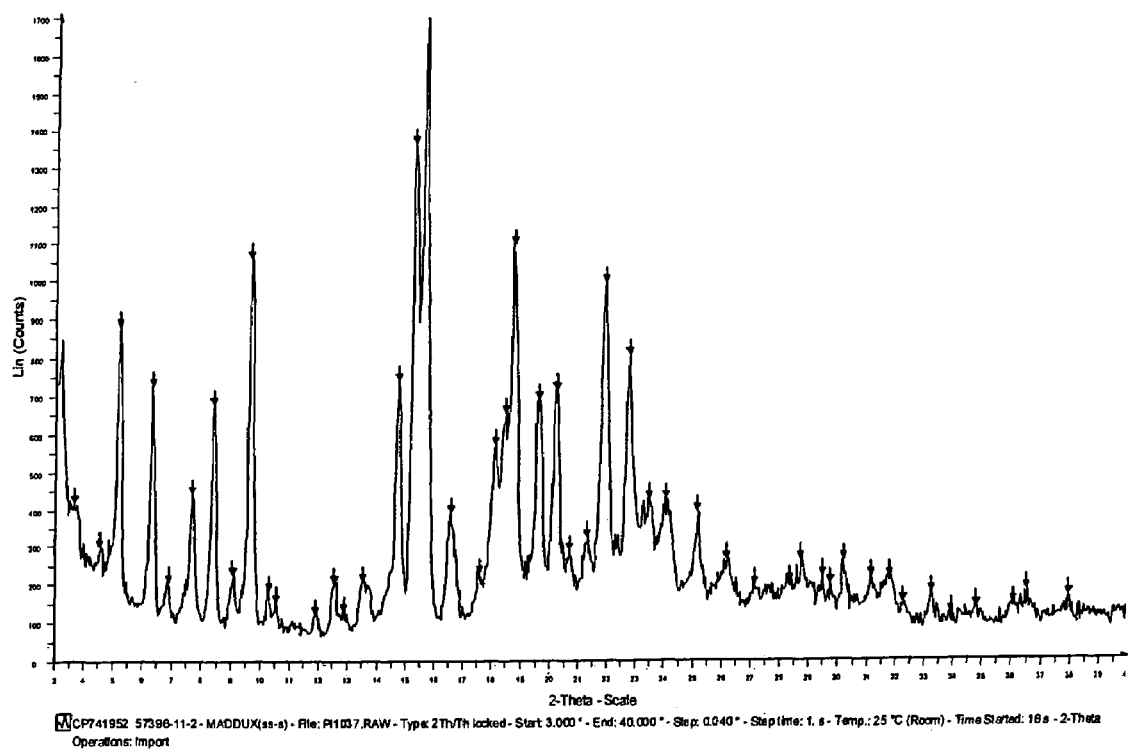

The powder diffraction patterns were collected on a Bruker D5000 powder X-ray diffractometer. The D5000 was equipped with copper radiation and Solex solid-state detector. The D5000 used theta/2 theta geometry. The slit system used to produce the line source was one 1.0 mm slit presample and two slits post sample (1.0 and 0.6 mm). The samples were scanned from 3.0 to 40.0 degrees in 2 theta. The step size was 0.04 degrees and each step was collected for 1 second.

DETAILED DESCRIPTION OF THE INVENTION

In the discussion which follows, certain common chemical abbreviations and acronyms have been employed which include: UHP (urea-hydrogen peroxide adduct), PyBroP (bromo-tris-pyrrolidino-phosphonium hexafluorophosphate), BOC (tert-butoxycarbonyl), EtOAc (ethyl acetate), NaH (sodium hydride), NaBH(OAc)$_3$ (sodium triacetoxy borohydride), HOBT (1-hydroxybenzotriazole), EDC (1-ethyl-3-(dimethylaminopropyl)-carbodiimide hydrochloride) and THF (tetrahydrofuran).

The present compounds may be envisioned as being composed of a central quinoline core and left- and right-hand appendages the individual components of which are represented below by compounds D, E and G respectively:

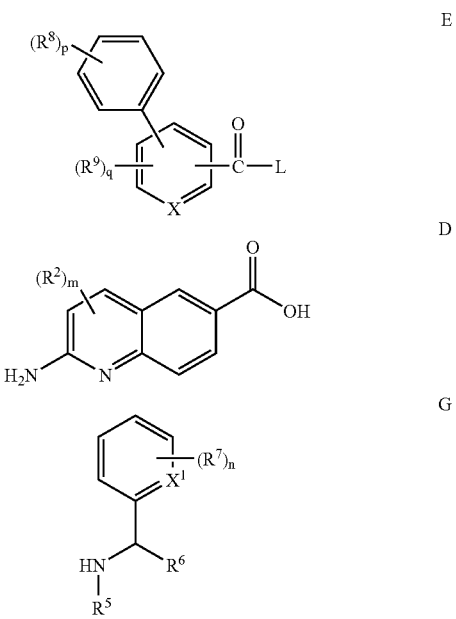

Preparation of the present compounds may proceed by combining E and D, then adding G to E-D. Alternatively, D and G may be combined to give D-G, which is then combined with E.

Scheme 1a below illustrates one means for preparing compounds of Formula (I) where —C(R$^3$)(R$^4$)— is —C(O)— and R$^1$ is R$^{1a}$. The corresponding compounds where R$^1$ is R$^{1b}$ may be similarly prepared by patterning compound (E) in the scheme below after R$^{1b}$ instead of R$^{1a}$ as described below.

Scheme 1a

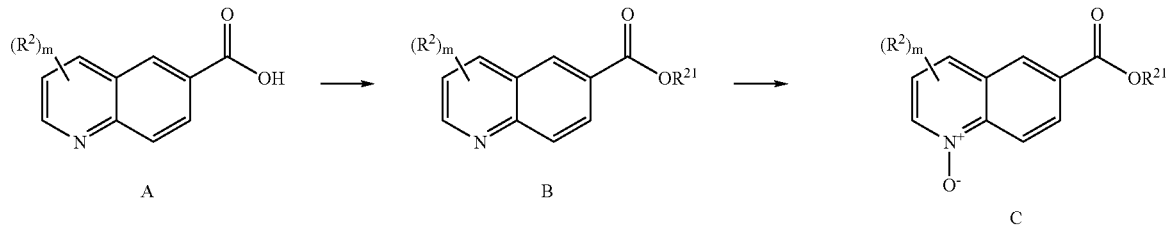

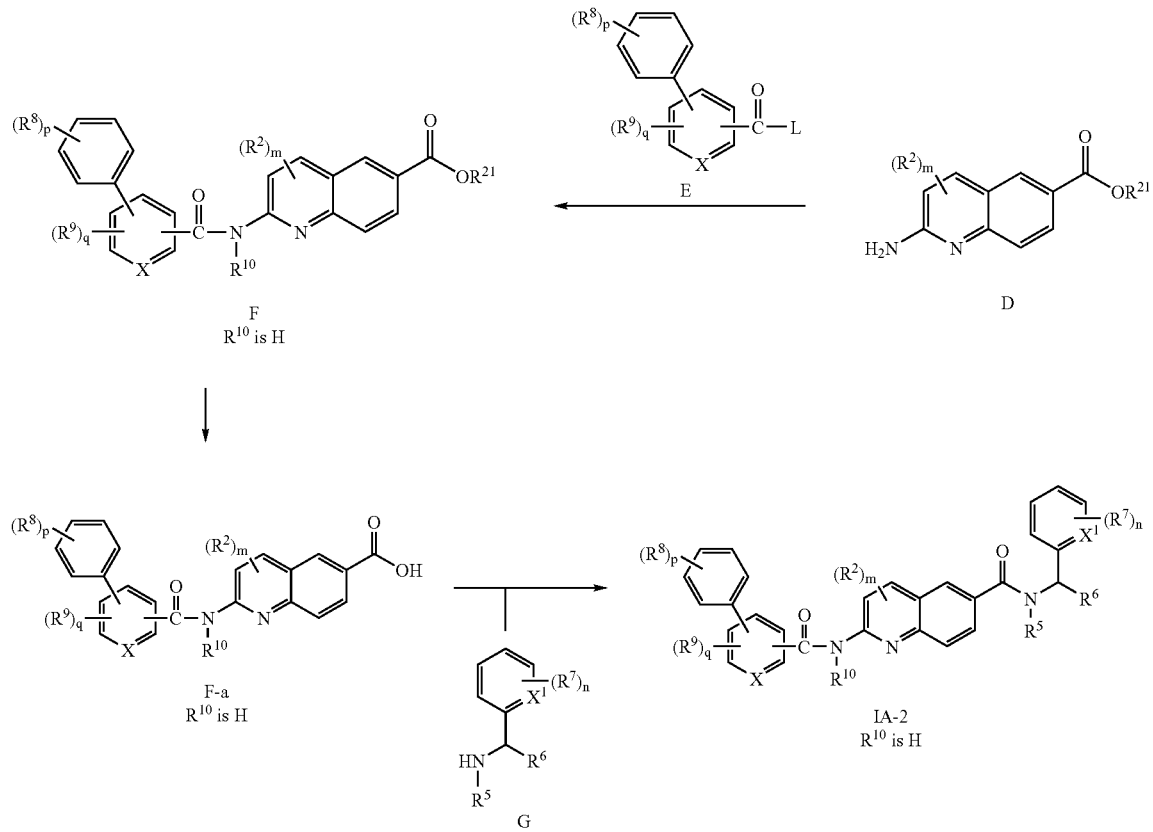

The carboxylic acid functionality in the quinolinecarboxylic acid (A) is protected using standard carboxylic acid protection procedures well known in the art, e.g., by formation of the corresponding ester, to give compound (B). For example, the benzyl ester ($R^{21}$ is benzyl in (B)) may be prepared by treating a solution of compound (A) in EtOAc at room temperature with 1,1'-carbonyldiimidazole to produce the activated, imidazolide derivative of (A, then adding benzyl alcohol to the reaction mixture.

The oxidation of compound (B) to the corresponding N-oxide, compound (C) may be conducted by procedures well known in the art. For example, the tert-butyl ester of (B) upon treatment with peroxytrifluoroacetic acid, generated from trifluoroacetic anhydride and UHP, provides the corresponding tert-butyl ester derivative of (C). Similarly, addition of the benzyl ester of (B) to a mixture of UHP and phthalic anhydride in methylene chloride under an inert atmosphere at room temperature gives the corresponding benzyl ester of (C).

The N-oxide (C) is treated with a sulfonyl chloride, preferably p-toluenesulfonyl chloride, to produce the corresponding sulfonate derivative, and the reaction mixture is then treated with a source of ammonia, e.g., aqueous ammonium hydroxide or ammonia in methanol to give the 2-aminoquinoline compound (D). Alternatively, the ammonia may be produced in situ in an organic solvent from an ammonium salt and an appropriate base. For example, where $R^{21}$ is benzyl, the compound (C)-sulfonyl chloride reaction mixture is added very slowly under an inert atmosphere to a suspension of ammonium chloride in methylene chloride and triethylamine with adequate cooling to control the resulting exotherm and contain the temperature in about the 25 to 30° C. range to give compound (D) where $R^{21}$ is benzyl.

The group "L" in compound (E) is —OH or a leaving group ("LG") such as a chlorine atom or an N-imidazole group. The activated carboxylic acid (E), in which L is LG, may be readily prepared from the corresponding carboxylic acid using materials and methods that are well known in the art. For example, the acid chloride compound (E) where X is —C($R^a$)— and $R^8$ is an optional substitutuent on the phenyl may be prepared from the corresponding carboxylic acid by treatment with, for example, oxalyl chloride or sulfonyl chloride. The corresponding compound (E) where L in an N-imidazole group may be prepared by the reaction of the corresponding free acid (E) with 1,1'-carbonyldiimidazole. The carboxylic acids of (E) where X is —C($R^a$)— are commercially available (e.g., 2-biphenylcarboxylic acid, 4'-methyl-2-biphenylcarboxylic acid and 4'-trifluoromethyl-2-biphenylcarboxylic acid), are known in the literature (e.g. European patent No. EP 0 059 983), or may be readily prepared by one of average skill in the art using materials and methods that are well known in the art. For example, a general synthesis of acids (E) where X is —C($R^a$)— involves Suzuki coupling between an arylboronic acid (e.g., 4-isopropylphenylboronic acid) and a halogenated benzoic acid ester derivative (e.g., ethyl-2-iodobenzoate), followed by hydrolysis of the ester function. Conditions for the Suzuki coupling involve heating the boronic acid and halogenated benzoic acid ester in the presence of a base (e.g., cesium carbonate, 2 equiv.) and a transition metal catalyst (e.g., tetrakistriphenylphosphinepalladium (0), 1 mol %) in a solvent such as 1,2-dimethoxyethane.

Also, the acids corresponding to those of compound (E) except that the $R^8$-bearing phenyl group is replaced with a ($C_4$-$C_7$)cycloalkyl group, e.g., 2-cyclohexylbenzoic acid and 2-cyclopentylbenzoic acid, may be prepared as described by Knochel et al (Tetrahedron 2000, 56, 4197) whereby ethyl 2-iodobenzoate is coupled with the corresponding cycloalkylzinc iodide in the presence of a nickel catalyst (Ni(acac)$_2$) to give the 2-cycloalkylbenzoic acid ethyl ester, which may then be converted to the corresponding acid by standard hydrolysis (e.g. aqueous LiOH/MeOH/THF).

The amide compound (F) where $R^{10}$ is H is formed by coupling the carboxylic acid (E) with the amino compound (D). The coupling may be achieved using a number of amide-bond forming methods and reagents well established in the chemical literature. A preferred procedure involves combination of the acid of (E) with the amino compound (D) in the presence of excess 1-(3-dimethylaminopropyl)-3-ethylcarbodiimide and excess 4-dimethylaminopyridine dissolved in methylene chloride. Another preferred method for coupling the acid of (E) with the amino compound (D) involves reaction between (D) and the acid chloride of (E). The reaction is carried out in the presence of a base (e.g., pyridine) using a solvent such as methylene chloride. Methods and reagents (e.g., oxalyl chloride) for preparing the acid chloride derived from E are well known to those of average skill in the art.

Alternatively, the coupling step and the step in which the activated carboxylic acid of (E) (L is a LG) is prepared from the acid of (E) (L is —OH) may in certain cases be conducted in the same pot. For example, addition, as a solid, of amine (D) where $R^{21}$ is benzyl to the product mixture formed by the reaction of the free acid of (E) with 1,1'-carbonyldiimidazole in THF, and heating the reaction mixture at reflux temperature gives compound (F) where $R^{10}$ is H and $R^{21}$ is benzyl.

The ester protecting group in compound (F) may be removed to give the carboxylic acid (F-a) or a salt thereof by saponification. For example, treatment of a mixture of compound F) where $R^{21}$ is benzyl in 2-propanol with an aqueous solution of potassium hydroxide, and heating the reaction mixture at reflux temperature gives the potassium salt of compound (F-a) where $R^{10}$ is H. The benzyl ester of compound (F) may also be deprotected by hydrogenation using conventional hydrogenation procedures. Alternatively, in an example where the protecting group is a tert-butyl ester, it may be hydrolyzed with strong acid such as trifluoracetic acid or a solution of hydrochloric acid.

Compounds of Formula (F) or (F-a) in which $R^{10}$ is alkyl may be prepared by alkylating compound (F) or (F-a) under standard conditions. For example, compound (F-a) where $R^{10}$ is methyl may be prepared by treating a solution of (F-a) ($R^{10}$ is H) in toluene with dimethyl sulfate in the presence of potassium carbonate, potassium hydroxide and tetrabutyl ammonium sulfate as described in the Examples section for the preparation of the intermediate 2-[methyl-(4'-trifluoromethyl-biphenyl-2-carbonyl)-amino]-quinoline-6-carboxylic acid.

The coupling of intermediates (F-a) and (G) into the final compound (IA-2) may be conducted using conventional amidation procedures well known in the art such as, for example, those disclosed in PCT patent application publication No. WO 03/002533. In one method, a base such as diisopropylethylamine is added in the cold to a solution of compounds (F-a), (G), HOBT and a coupling agent such as EDC in an organic solvent such as methylene chloride to give the final product amide (IA-2). Alternatively, the potassium salt of compound (F-a) may be converted into a mixed anhydride, for example by treatment of the potassium salt in EtOAc and TEA in the cold with a solution of isopropyl chloroformate in toluene followed by allowing the reaction mixture to warm to room temperature. To this reaction mixture is added a solution of compound (G) in EtOAc in the cold (e.g., ~–20° C.) to give compound (IA-2). On work-up it may be advantageous to crystallize the product from the reaction mixture (after solvent displacement into ethanol via azeotropic distillation of EtOAc and toluene with ethanol) in the presence of an amine base such as aqueous ammonium hydroxide to remove any residual compound (F-a) starting material.

Appropriately substituted intermediate (G) in which the carbon atom to which $R^6$ is attached is chiral or racemic may be prepared by conventional procedures well known in the art (see, for example, WO 03/002533 supra and U.S. Pat. No. 6,369,075).

Compound (G) where $R^6$ is —C(O)N($R^{14}$)($R^{15}$), n is 0, $R^5$ is H or —CH$_3$ and $X^1$ is —CH— (compound (G-1)) may be conveniently prepared from commercially available Boc-phenylglycines by treatment with HN($R^{14}$)($R^{15}$) and a coupling agent such as PyBroP in the presence of a base such as diisopropylethylamine followed by removal of the BOC protecting group as illustrated in the equation below for the conversion of (H) into (G-1). Other $R^5$ substituents may be introduced by reductive amination by treating (G-1) with an appropiate aldehyde or ketone and a reducing agent such as NaBH(OAc)$_3$

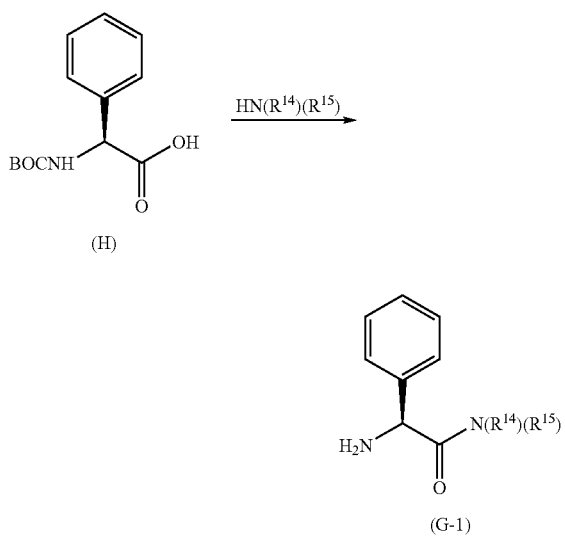

Compound (G) where $R^6$ is —CO$_2$R$^{20}$ may be prepared by esterifying appropriately substituted (H) with R$^{20}$OH and removing the BOC protecting group.

Compound (G) where $R^6$ is —CH$_2$—W—Y may be prepared as illustrated in the equations below for the compound in which W is —O—, n is 0, $R^5$ is H and $X^1$ is —CH— (compound (G-2)). Compound (J), which is commercially available, is treated with triphenylmethyl chloride in the presence of triethylamine in an organic solvent such as dichloromethane to give the amine-protected compound (J-1), which is then treated with a Y-halide in the presence of a base (e.g., NaH) in an organic solvent (e.g., THF) to give, after removal of the triphenylmethyl group by treatment with acid (e.g., 4 M HCl/dioxane), compound (G-2).

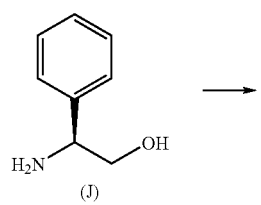
(J)

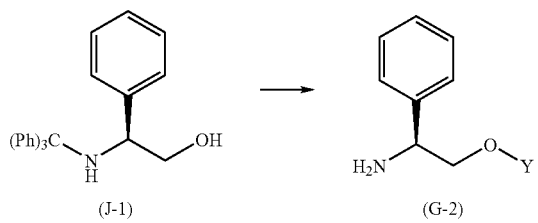
(J-1)　　　　　(G-2)

Compound (G) where $R^6$ is —CH$_2$N(R$^c$)(R13) may be prepared as illustrated in the equation below for the compound in which n is 0, $R^5$ is H and $X^1$ is —CH— (compound (G-4)). Compound (J-2b) may be prepared from compound (H) in a manner analogous to that described above for the preparation of compound (G-1) from (H). Compound (J-2b) is reduced by treatment with, for example, lithium aluminum hydride in THF to give, after removal of the BOC protecting group, the amine (G-4).

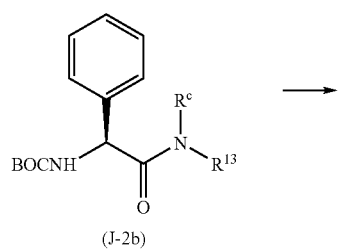
(J-2b)

-continued

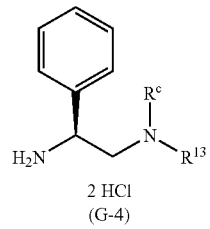
2 HCl
(G-4)

An alternative method for making certain of the compounds of Formula (I) in which $R^6$ is —CH$_2$N(R$^c$)(R$^{13}$) proceeds via the azide intermediate (G-3), which may be prepared as illustrated in the equations below. A solution of compound (J-2) and triethylamine in methylene chloride is treated with methanesulfonyl chloride in the cold to give the corresponding methanesulfonate ester (J-2a), which upon treatment with sodium azide in dimethyl sulfoxide affords the azide (G-3).

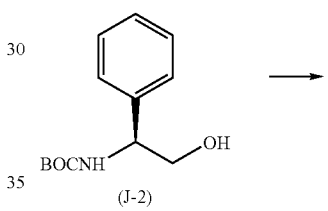
(J-2)

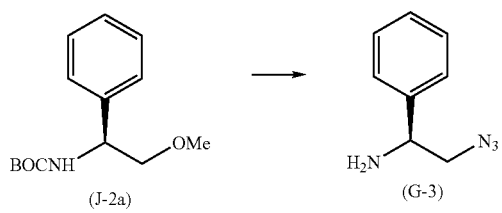
(J-2a)　　　　　(G-3)

Compound (G-3) may be coupled with the appropriately substituted quinoline-6-carboxylic acid derivative (F-a) to give the corresponding amide adduct in which $R^6$ is —CH$_2$N$_3$. Treatment with triphenyl phosphine, then with sodium hydroxide (1 N solution) gives the corresponding —CH$_2$NH$_2$ compound which may be suitably derivatized to provide compounds of Formula (I) in which $R^6$ is —CH$_2$N(R$^c$)(R$^{13}$) (see, for example, Examples 5 and 6 below).

Scheme Ib below illustrates an alternative method for preparing compounds of Formula (I) where —C(R$^3$)(R$^4$)— is —C(O)— and $R^1$ is R$^{1a}$. As above, the corresponding compounds where $R^1$ is R$^{1b}$ may be similarly prepared by patterning compound (E) in the scheme below after R$^{1b}$ instead of R$^{1a}$.

Scheme Ib

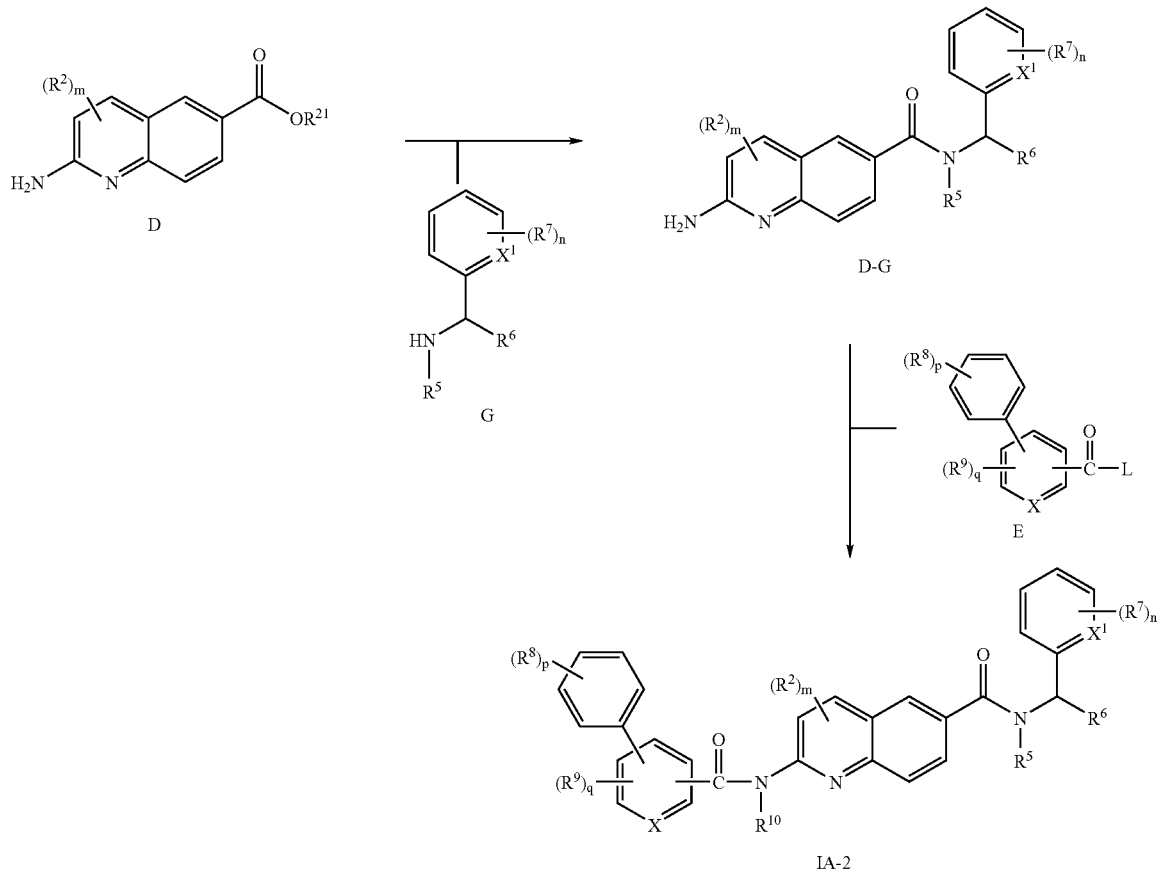

The compound (D) acid ($R^{21}$ is H) or a salt of the acid (e.g., $R^{21}$ is a cation such as $K^{(+)}$) may be coupled with compound (G), under conditions similar to those described above for the coupling of compound (F-a) with (G) in Scheme Ia, to give compound (D-G). Similarly, compound (D-G) may be then coupled with compound (E) (L is —OH or LG) under amidation conditions similar to those described above for the coupling of compound (D) with (E) in Scheme Ia, to give product (IA-2).

The compounds of Formula (I) where $R^3$ and $R^4$ are each H may be prepared as illustrated in Scheme II below.

Scheme II

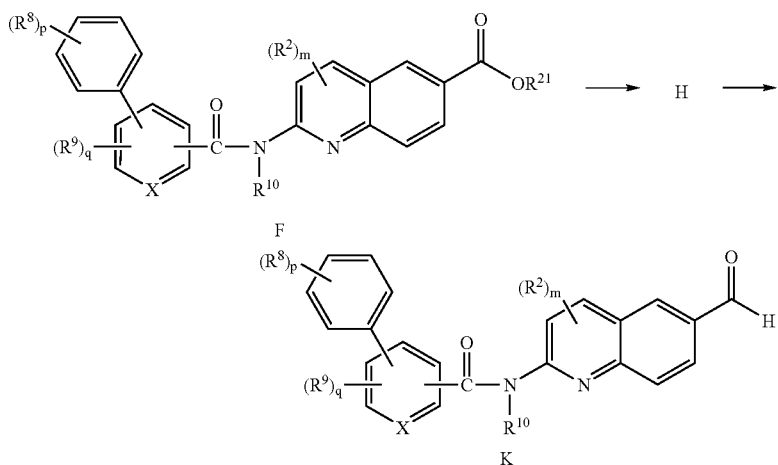

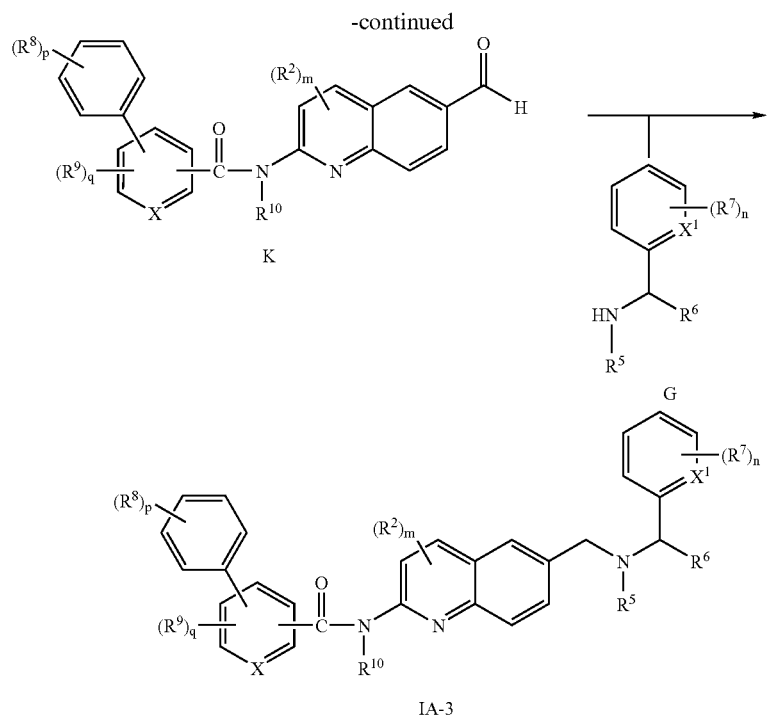

The ester functionality in compound (F) is reduced, for example with diisobutyl aluminum hydride in an organic solvent such as THF, to give the corresponding alcohol (H), which is oxidized, for example with Dess Martin periodinane in $CH_2Cl_2$, to give the corresponding aldehyde (K). The aldehyde (K) was combined with intermediate (G) in the presence of a reducing agent such as sodium triacetoxy borohydride to give the compound of Formula (I) where $R^3$ and $R^4$ are each H, compound (IA-3) in Scheme II.

Conventional methods and/or techniques of separation and purification known to one of ordinary skill in the art can be used to isolate the compounds of the present invention, as well as the various intermediates related thereto. Such techniques will be well known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds and intermediates of the invention that are basic in nature are capable of forming a wide variety of salts with various inorganic and organic acids. The salts may be prepared in situ during the final isolation and purification of a compound, or by separately reacting the compound with a suitable organic or inorganic acid and isolating the salt thus formed.

Representative pharmaceutically acceptable acid addition salts of the present compounds include hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesuionate, benzenesulfonate, p-toluenesulfonate, pamoate, palmitate, malonate, stearate, laurate, malate, borate, hexafluorophosphate, naphthylate, glucoheptonate, lactobionate and laurylsulfonate salts and the like. A preferred salt of the compounds is the hydrochloride salt.

Certain of the compounds and intermediates of the invention are acidic in nature and are capable of forming salts with bases. The salts may include cations based on the alkali and alkaline earth metals, such as sodium, lithium, potassium, calcium, magnesium, and the like, as well as ammonium, quaternary ammonium, and 1, 2 or 3 amine-derived cations including, but not limited to, ammonium, tetramethylammonium and tetraethylammonium and cations derived from methylamine, ethylamine, dimethylamine, trimethylamine, triethylamine, and the like. See, e.g., Berge, et al., *J. Pharm. Sci.*, 66, 1-19 (1977). Sodium and potassium salts are preferred.

The present invention also includes prodrugs of the compounds of Formula (I). As used herein, the term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series; in Bioreversible Carriers in Drug Design, ed. Edward B. Roche, American Pharmaceutical Association and Pergamon Press, 1987; in *Advanced Drug Delivery Reviews,* 1996, 19, 115; and in *J. Med. Chem.* 1996, 39, 10.

For example, where a compound of the present invention contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, where a compound of the present invention contains an alcohol functional group, a prodrug can be formed by replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-C6)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$-$C_6$)alkyl)$_2$ or glycosyl (the radical resulting from the removal of a hydroxyl group of the hemiacetal form of a carbohydrate).

Where a compound of the present invention contains an amine functional group, a prodrug can be formed by the replacement of a hydrogen atom in the amine group with a group such as R-carbonyl-, RO-carbonyl-, NRR'-carbonyl- where R and R' are each independently ($C_1$-$C_{10}$)alkyl, ($C_3$-$C_7$)cycloalkyl, benzyl, or R-carbonyl is a natural a-aminoacyl or natural α-aminoacyl-natural α-aminoacyl, —C(OH)C(O)OY' wherein Y' is H, ($C_1$-$C_6$)alkyl or benzyl, —C(OY$_0$)Y$_1$ wherein Y$_0$ is ($C_1$-$C_4$) alkyl and Y$_1$ is ($C_1$-$C_6$) alkyl, carboxy($C_1$-$C_6$)alkyl, amino($C_1$-$C_4$)alkyl or mono-N— or di-N,N-($C_1$-$C_6$)alkylaminoalkyl, —C(Y$_2$)Y$_3$ wherein Y$_2$ is H or methyl and Y$_3$ is mono-N— or di-N,N-($C_1$-$C_6$)alkylamino, morpholino, piperidin-1-yl or pyrrolidin-1-yl.

Many of the compounds of the present invention contain one or more asymmetric or chiral centers, and such compounds therefore exist in different stereoisomeric forms (e.g., enantiomers and diastereoisomers). It is intended that all stereoisomeric forms of the intermediates and compounds of the present invention as well as mixtures thereof, including racemic mixtures, which possess properties useful in the treatment of the conditions discussed herein or are intermediates useful in the preparation of compounds having such properties, form a part of the present invention. In addition, the present invention embraces all geometric isomers and atropisomers. For example, if an intermediate or compound of the present invention contains a double bond or a fused ring, both the cis- and trans- forms, as well as mixtures, are embraced within the scope of the invention.

Diastereomeric mixtures may be separated into their individual diastereoisomers on the basis of their physical chemical differences by methods well known to those skilled in the art, such as by chromatography and/or fractional crystallization. Enantiomers may be separated by use of a chiral HPLC column. They may also be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers.

The compounds of the present invention may exist in unsolvated as well as solvated forms with pharmaceutically acceptable solvents such as water, ethanol, and the like, and both solvated and unsolvated forms are included within the scope of the invention.

A number of the compounds of the present invention and intermediates therefor exhibit tautomerism and therefore may exist in different tautomeric forms under certain conditions. All such forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also embraces isotopically-labeled compounds which are identical to the compounds of Formula (I) or intermediates therefor but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

The compounds of the present invention inhibit MTP/Apo B secretion, and are therefore useful in treating or preventing any of the disease states or conditions in which Apo B, serum cholesterol and/or triglyceride levels are elevated. Such disease states or conditions include obesity, atherosclerosis, pancreatitis, hypercholesterolemia, hypertriglyceridemia, hyperlipidemia and diabetes. The present invention is also useful in treating or managing non-obese overweight conditions and normal weight conditions where weight control or management is desired in order to prevent an obese or overweight condition from developing, or to just maintain an optimum, healthy weight. Also, the compounds of the present invention are useful in treating or preventing the diseases and conditions that are clinical sequelae of the diseases or conditions mentioned above. Additionally, the present compounds are useful in the treatment or prevention of any condition in which it is desirable to reduce food intake.

Therefore, the present invention provides methods of treatment or prevention of such disease states or conditions in an animal which comprises administering to the animal a compound of Formula (I), preferably a therapeutically effective amount thereof. A preferred subgroup of the disease states or conditions described hereinabove is atherosclerosis, obesity, hypercholesterolemia, hypertriglyceridemia, hyperlipidemia, and diabetes as well as non-obese overweight conditions.

The present compounds will generally be administered in the form of a pharmaceutical composition. Accordingly, the present invention also provides pharmaceutical compositions comprising a therapeutically effective amount of a compound of Formula (I) in admixture with a pharmaceutically acceptable carrier or diluent, as well as methods of treatment or prevention of disease states or conditions that are modulated by MTP or Apo-B secretion inhibitors in an animal, which comprises administering to the animal such a pharmaceutical composition.

The compounds of Formula (I) and compositions containing them are also useful in in the manufacture of a medicament for the therapeutic applications described herein.

The compounds of the present invention may be administered to a patient at dosage levels in the range of about 0.1 mg to about 3,000 mg per day. The dosage for a human is from about 1 mg to about 1,000 mg per day; preferably, from about 1 mg to about 500 mg per day; more preferably, from about 1 mg to about 250 mg per day; most preferably, from about 1 mg to about 100 mg per day; generally from about 1 mg to about 50 mg per day. The specific dosage and dosage range that can be used depends on a number of factors, including the age and weight of the patient, the mode of administration, the severity of the condition or disease being treated, and the pharmacological activity of the compound being administered. The determination of dosage ranges and optimal dosages for a particular patient is well within the ordinary skill in the art.

The compounds of this invention may be used in conjunction with other pharmaceutical agents for the treatment of the disease states or conditions described herein. Therefore methods of treatment that include administering compounds of the present invention in combination with other pharmaceutical agents are also provided by the present invention.

Suitable pharmaceutical agents that may be used in combination with the compounds of the present invention include other anti-obesity agents such as cannabinoid-1 (CB-1) antagonists (such as rimonabant), 11β-hydroxy steroid dehydrogenase-1 (11β-HSD type 1) inhibitors, peptide YY (PYY) and PYY agonists (such as $PYY_{3-36}$ or analogs or derivatives thereof), MCR-4 agonists, cholecystokinin-A (CCK-A) agonists, monoamine reuptake inhibitors (such as sibutramine), sympathomimetic agents, $β_3$ adrenergic receptor agonists, dopamine receptor agonists (such as bromocriptine), melanocyte-stimulating hormone receptor analogs, 5HT2c receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y receptor antagonists (e.g., NPY Y5 receptor antagonists), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists and the like.

Lipase inhibitors are useful in the practice of the combination aspect of the present invention. Lipase inhibitors inhibit the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Lipase inhibition activity is readily determined by the use of standard assays well known in the art. See, for example, Methods Enzymol. 286: 190-231, incorporated herein by reference.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors of this lipase find utility in the treatment of obesity and associated conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92, 125 (1987).

A variety of pancreatic lipase inhibitors useful in the present invention are described hereinbelow. The pancreatic lipase inhibitors lipstatin, (2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin, (2S, 3S, 5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. Tetrahydrolipstatin may be prepared as described in U.S. Pat. Nos. 5,274,143; 5,420,305; 5,540,917; and 5,643,874. The pancreatic lipase inhibitor FL-386, 1-[4-(2-methylpropyl)cyclohexyl]-2-[(phenylsulfonyl)oxy]-ethanone, and variously substituted sulfonate derivatives related thereto are disclosed in U.S. Pat. No. 4,452,813. The pancreatic lipase inhibitor WAY-121898, which is 4-phenoxyphenyl-4-methylpiperidin-1-yl-carboxylate, and various carbamate esters and pharmaceutically acceptable salts related thereto are disclosed in U.S. Pat. Nos. 5,512,565; 5,391,571 and 5,602,151. The pancreatic lipase inhibitor valilactone and a process for preparing it by microbial cultivation of *Actinomycetes* strain MG147-CF2 are disclosed in Kitahara, et al., *J. Antibiotics,* 40 (11), 1647-1650 (1987). The pancreatic lipase inhibitors ebelactone A and ebelactone B and processes for preparing them by microbial cultivation of *Actinomycetes* strain MG7-G1 are disclosed in Umezawa, et al., *J. Antibiotics,* 33, 1594-1596 (1980). The use of ebelactones A and B in the suppression of monoglyceride formation is disclosed in Japanese Kokai 08-143457, published Jun. 4, 1996. All of the references cited above are incorporated herein by reference.

Preferred lipase inhibitors include lipstatin, tetrahydrolipstatin, valilactone, esterastin, ebelactone A, and ebelactone B,particularly tetrahydrolipstatin. The lipase inhibitor N-3-trifluoromethylphenyl-N'-3-chloro-4'-trifluoromethylphenylurea, and the various urea derivatives related thereto are disclosed in U.S. Pat. No. 4,405,644. Esteracin is disclosed in U.S. Pat. Nos. 4,189,438 and 4,242,453. The lipase inhibitor cyclo-O,O'-[(1,6-hexanediyl)-bis-(iminocarbonyl)] dioxime and the various bis(iminocarbonyl)dioximes related thereto may be prepared as described in Petersen et al., *Liebig's Annalen,* 562, 205-229 (1949). All of the references cited above are incorporated herein by reference.

Preferred NPY receptor antagonists include NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345 and 6,326,375; U.S. patent application publication Nos. 2002/0151456 and 2003/036652 and PCT patent application publication Nos. WO 03/010175; WO 03/082190 and WO 02/048152.

Other MTP/Apo B secretion inhibitors are also useful as the second anti-obesity agent in the combination aspect of this invention. Such inhibitors include, for example, imputapride (Bayer) and the compounds disclosed in U.S. Pat. Nos. 5,712,279; 5,731,340; 5,741,804; 5,968,950; 6,066,653 and 6,492,365; PCT patent application publication Nos. WO 96/40640, WO 97/43257, WO 98/23593, WO 98/27979, WO 99/33800, WO 00/05201, WO 02/28835 and WO 03/002533; and European patent application publication Nos. 0 584 446; 0 643 057; 1 099 439 and 1 099 701.

The following MTP/Apo B secretion inhibitors are particularly useful:

4'-trifluoromethyl-biphenyl-2-carboxylic acid [2-(1 H-[1,2,4,]triazol-3-ylmethyl)-1,2,3,4-tetrahydro-isoquinolin-6-yl]-amide;

4'-trifluoromethyl-biphenyl-2-carboxylic acid [2-(2-acetylamino-ethyl)-1,2,3,4-tetrahydro-isoquinolin-6-yl]-amide;

(2-{6-[(4'-trifluoromethyl-biphenyl-2-carbonyl)-amino]-3,4-dihydro-1H-isoquinolin-2-yl)-ethyl)-carbamic acid methyl ester;

4'-trifluoromethyl-biphenyl-2-carboxylic acid [2-(1H-imidazol-2-yl methyl)-1,2,3,4-tetrahydro-isoquinolin-6-yl]-amide;

4'-trifluoromethyl-biphenyl-2-carboxylic acid [2-(2,2-diphenyl-ethyl)-1,2,3,4-tetrahydro-isoquinolin-6-yl]-amide;

4'-trifluoromethyl-biphenyl-2-carboxylic acid [2-(2-ethoxy-ethyl)-1,2,3,4-tetrahydro-isoquinolin-6-yl]-amide;

(S)-1-ethyl-5-[(4'-trifluoromethyl-biphenyl-2-carbonyl)-amino]-1H-indole-2-carboxylic acid (2-[benzyl(methyl) amino]-2-oxo-1-phenylethyl}amide;

(S)-N-{2-[benzyl(methyl)amino]-2-oxo-1-phenylethyl)-1-methyl-5-[4'-(trifluoromethyl)[1,1'-biphenyl]-2-carboxamido]-1H-indole-2-carboxamide;

3-chloro-5-[(4'-trifluoromethyl-biphenyl-2-carbonyl)-amino]-1H-indole-2-carboxylic acid {2[benzyl(methyl) amino]-2-oxo-1-phenylethyl}amide;

3-chloro-1-methyl-5-[(4'-trifluoromethyl-biphenyl-2-carbonyl)-amino]-1H-indole-2-carboxylic acid {2-[benzyl(methyl)amino]-2-oxo-1-phenylethyl}amide;

3-chloro-1-methyl-5-[(4'-trifluoromethyl-biphenyl-2-carbonyl)-amino]-1H-indole-2-carboxylic acid {N-[2-(benzyl (methyl)amino)-2-oxo-1-phenylethyl]methyl}amide;

3-chloro-1-methyl-5-[methyl-(4'-trifluoromethyl-biphenyl-2-carbonyl)-amino]-1H-indole-2-carboxylic acid {2-[benzyl(methyl)amino]-2-oxo-1-phenylethyl}amide;

3-chloro-1-ethyl-5-[(4'-trifluoromethyl-biphenyl-2-carbonyl)-amino]-1H-indole-2-carboxylic acid {2-[benzyl (methyl)amino]-2-oxo-1-phenylethyl}amide;

9-[4-[4-(2,3-dihydro-1-oxo-1H-isoindol-2-yl)-1-piperidinyl]butyl]-N-propyl-9H-carboxamide (BMS-197636);

2-[1-(3,3-diphenylpropyl)-4-piperidinyl]-2,3-dihydro-1H-isoindol-1-one (BMS-200150); and 9-[4-(4-[2-(4-trifluoromethylphenyl)benzoylamino]piperidin-1-yl]butyl]-N-2,2,2-trifluoroethyl)-9H-fluorene-9-carboxamide (BMS 201038).

Preferred anti-obesity agents include orlistat (U.S. Pat. Nos. 5,274,143; 5,420,305; 5,540,917; and 5,643,874), sibutramine (U.S. Pat. No. 4,929,629), bromocriptine (U.S. Pat. Nos. 3,752,814 and 3,752,888), ephedrine, leptin, pseudoephedrine and peptide $YY_{3-36}$ or an analog or derivative thereof (U.S. patent application publication No. 2002/0141985 and PCT patent application publication No. WO 03/026591. All of the above-recited references are incorporated herein by reference.

The compounds of this invention may also be used in conjunction with other pharmaceutical agents (e.g., LDL-cholesterol lowering agents, triglyceride lowering agents) for the treatment of the disease/conditions described herein. For example, the present compounds may be used in combination with an HMG-CoA reductase inhibitor, a cholesterol synthesis inhibitor, a cholesterol absorption inhibitor, a CETP inhibitor, a PPAR modulator or other cholesterol lowering agent such as a fibrate, niacin, an ion-exchange resin, an antioxidant, an ACAT inhibitor or a bile acid sequestrant. Other pharmaceutical agents useful in the practice of the combination aspect of the invention include bile acid reuptake inhibitors, ileal bile acid transporter inhibitors, ACC inhibitors, antihypertensive agents (such as Norvasc®), antibiotics, antidiabetics (such as metformin), PPARγ activators, sulfonylureas, insulin, aldose reductase inhibitors (ARI) (e.g., zopolrestat), sorbitol dehydrogenase inhibitors (SDI)), and anti-inflammatory agents such as aspirin or, preferably, an anti-inflammatory agent that inhibits cyclooxygenase-2 (Cox-2) to a greater extent than it inhibits cyclooxygenase-1 (Cox-1) such as celecoxib (U.S. Pat. No. 5,466,823), valdecoxib (U.S. Pat. No. 5,633,272, parecoxib (U.S. Pat. No. 5,932,598), deracoxib (CAS RN 169590-41-4), etoricoxib (CAS RN 202409-33-4) or lumiracoxib (CAS RN 220991-20-8).

A slow-release form of niacin is commercially available under the brand name Niaspan. Niacin may also be combined with other therapeutic agents such as lovastatin, which is an HMG-CoA reductase inhibitor. This combination therapy is known as Advicor® (Kos Pharmaceuticals Inc.

Any HMG-CoA reductase inhibitor may be used as the second compound in the combination aspect of this invention. The term HMG-CoA reductase inhibitor refers to compounds that inhibit the bioconversion of hydroxymethylglutaryl-coenzyme A to mevalonic acid catalyzed by the enzyme HMG-CoA reductase. Assays for determining are known in the art (e.g., Meth. Enzymol. 1981; 71:455-509 and references cited therein). HMG-CoA reductase inhibitors of interest herein include those disclosed in U.S. Pat. No. 4,231,938 (compounds isolated after cultivation of a microorganism belonging to the genus *Aspergillus*, such as lovastatin), U.S. Pat. No. 4,444,784 (synthetic derivatives of the aforementioned compounds such as simvastatin), U.S. Pat. No. 4,739,073 (substituted indoles such as fluvastatin), U.S. Pat. No. 4,346,227 (ML-236B derivatives such as pravastatin), European patent application publication No. 491 226 A (pyridyldihydroxyheptenoic acids such as cerivastatin), U.S. Pat. No. 5,273,995 (6-[2-(substituted-pyrrol-1-yl)alkyl]pyran-2-ones such as atorvastatin and pharmaceutically acceptable forms thereof (i.e. Lipitor®)) Additional HMG-CoA reductase inhibitors of interest herein include rosuvastatin and pitavastatin. All of the references cited above are incorporated herein by reference.

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). CETP inhibitors useful in the combination aspect of the present invention include those disclosed in U.S. Pat. Nos. 6,140,343 and 6,197,786. CETP inhibitors disclosed in these patents include compounds such as [2R, 4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. Also of interest are the CETP inhibitors disclosed in U.S. patent application Ser. No. 60/458274, filed Mar. 28, 2003, U.S. Pat. No. 5,512,548 (polypeptide derivatives), J. Antiblot., 49(8): 815-816 (1996) (rosenonolactone derivatives) and Bioorg. Med. Chem. Lett.; 6:1951-1954 (1996) (phosphate-containing analogs of cholesteryl ester). All of the references cited above are incorporated herein by reference.

Any PPAR modulator may be used as the second compound in the combination aspect of this invention. The term PPAR modulator refers to compounds which modulate peroxisome proliferator activator receptor (PPAR) activity in mammals, particularly humans. Such modulation may be readily determined by standard assays known in the art. It is believed that such compounds, by modulating the PPAR receptor, stimulate transcription of key genes involved in fatty acid oxidation and genes involved in high density lipoprotein (HDL) assembly (for example, apolipoprotein Al gene transcription), accordingly reducing whole body fat and increasing HDL cholesterol. By virtue of their activity, these compounds also reduce plasma levels of triglycerides, VLDL cholesterol, LDL cholesterol and their associated components and increase HDL cholesterol and apolipoprotein Al. Hence, these compounds are useful for the treatment and correction of the various dyslipidemias associated with the development and incidence of atherosclerosis and cardiovascular disease, including hypoalphalipoproteinemia and hypertriglyceridemia. PPARα activators of interest herein include those disclosed in PCT patent application publication Nos. WO 02/064549 and WO 02/064130 and U.S. patent application Ser. No. 10/720,942, filed Nov. 24, 2003. All of the references cited above are incorporated herein by reference.

Any HMG-CoA synthase inhibitor may be used as the second compound in the combination aspect of this invention. The term HMG-CoA synthase inhibitor refers to compounds that inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by standard assays known in the art. (Meth Enzymol. 1975; 35:155-160: Meth. Enzymol. 1985; 110:19-26 and references cited therein). HMG-CoA synthase inhibitors of interest include those disclosed in U.S. Pat. No. 5,120,729 (beta-lactam derivatives), U.S. Pat. No. 5,064,856 (spiro-lactone derivatives prepared by culturing a microorganism (MF5253)) and U.S. Pat. No. 4,847,271 (certain oxetane compounds such as 11-(3-hydroxymethyl-4-oxo-2-oxetayl)-3,5,7-trimethyl-2,4-undeca-dienoic acid derivatives). All of the references cited above are incorporated herein by reference.

Any compound that decreases HMG-CoA reductase gene expression may be used as the second compound in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol., 1985; 110:9-19). U.S. Pat. No. 5,041,432 discloses certain 15-substituted lanosterol derivatives that decrease HMG-CoA reductase gene expression. Other oxygenated sterols that suppress synthesis of HMG-CoA reductase are discussed by E. I. Mercer (Prog. Lip. Res. 1993;32:357-416). The references cited above are incorporated herein by reference.

Squalene synthetase inhibitors are also useful in the practice of the combination aspect of the invention. Such compounds inhibit the condensation of 2 molecules of farnesylpyrophosphate to form squalene, catalyzed by the enzyme squalene synthetase. Standard assays for determining squalene synthetase inhibition are well known in the art. (Meth. Enzymol. 1969; 15: 393-454 and Meth. Enzymol. 1985; 110:359-373 and references contained therein. Squalene synthetase inhibitors of interest herein include those disclosed in U.S. Pat. No. 5,026,554 (fermentation products of the microorganism MF5465 (ATCC 74011) including zaragozic acid) as well as those included in the summary of patented squalene synthetase inhibitors which appears in Curr. Op. Ther. Patents (1993) 861-4. The references cited above are incorporated herein by reference.

Any squalene epoxidase inhibitor may be used as the second compound in the combination aspect of this invention. These compounds inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794: 466-471), squalene epoxidase inhibitors of interest herein include those disclosed in U.S. Pat. Nos. 5,011,859 and 5,064,864 (fluoro analogs of squalene), European patent application publication No. 395,768 A (substituted allylamine derivatives), PCT patent application publication No. WO 93/12069 A (amino alcohol derivatives) and U.S. Pat. No. 5,051,534 (cyclopropyloxy-squalene derivatives). All of the references cited above are incorporated herein by reference.

Squalene cyclase inhibitors are also contemplated herein as a viable pharmaceutical agent for use in the combination aspect of the invention. These compounds inhibit the bioconversion of squalene-2,3-epoxide to lanosterol, catalyzed by the enzyme squalene cyclase. Such inhibition is readily determined by standard assays well known in the art. (FEBS Lett. 1989;244:347-350.). Squalene cyclase inhibitors of interest include those disclosed in PCT patent application publication No. WO 94/10150 (1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8 (beta)-trimethyl-6(beta)-isoquinolineamine) and French patent application publication No. 2697250 (beta, beta-dimethyl-4-piperidine ethanol derivatives such as 1-(1,5,9- trimethyldecyl)-beta,beta-dimethyl-4-piperidineethanol).

The references cited above are incorporated herein by reference.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. Combined squalene epoxidase/squalene cyclase inhibiton is readily determined in standard assays for squalene cyclase inhibitors or squalene epoxidase inhibitors. Squalene epoxidase/squalene cyclase inhibitors useful in the practice of the combination aspect of the invention include those disclosed in U.S. Pat. Nos. 5,084,461 and 5,278,171 (azadecalin derivatives), European patent application publication No. 468,434 (piperidyl ether and thio-ether derivatives such as 2-(1-piperidyl)pentyl isopentyl sulfoxide and 2-(1-piperidyl)ethyl ethyl sulfide), PCT patent application publication No. WO 94/01404 (acyl-piperidines such as 1-(1-oxopentyl-5-phenylthio)-4-(2-hydroxy-1-methyl)-ethyl) piperidine) and U.S. Pat. No. 5,102,915 (cyclopropyloxy-squalene derivatives). All of the references cited above are incorporated herein by reference.

The compounds of the present invention can also be administered in combination with naturally occurring substances that act to lower plasma cholesterol levels. These naturally occurring materials are commonly called nutraceuticals and include, for example, garlic extract, *Hoodia* plant extracts and niacin.

Cholesterol absorption inhibitors may also be used in the combination aspect of the present invention. The term cholesterol absorption inhibition refers to the ability of a compound to prevent cholesterol contained within the lumen of the intestine from entering into the intestinal cells and/or passing from within the intestinal cells into the blood stream. Such cholesterol absorption inhibition activity is readily determined in standard assays (e.g., J. Lipid Res. (1993) 34: 377-395). Cholesterol absorption inhibitors of interest include those disclosed in PCT patent application publication No. WO 94/00480. A preferred cholesterol absorption inhibitor is Zetia™ (ezetimibe) (Merck/Schering-Plough). The references cited above are incorporated herein by reference.

Any ACAT inhibitor may serve as the second compound in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined by standard assays, such as the method of Heider et al. described in *Journal of Lipid Research.*, 24:1127(1983). ACAT inhibitors useful herein include those disclosed in U.S. Pat. No. 5,510,379 (carboxysulfonates) and PCT patent application publication Nos. WO 96/26948 and WO 96/10559 (both disclose urea derivatives). Preferred ACAT inhibitors include avasimibe (Pfizer), CS-505 (Sankyo) and eflucimibe (Eli Lilly and Pierre Fabre). All of the references cited above are incorporated herein by reference.

Other compounds that are marketed for hyperlipidemia, including hypercholesterolemia, and which are intended to help prevent or treat atherosclerosis and are of interest herein include bile acid sequestrants, such as Welchol®, Colestid®, LoCholest® and Questran®; and fibric acid derivatives, such as Atromid®, Lopid® and Tricor®.

Diabetes (especially Type II), insulin resistance, impaired glucose tolerance, or the like, and any of the diabetic complications such as neuropathy, nephropathy, retinopathy or cataracts may be treated by the administration of a therapeutically effective amount of a compound of Formula (I) in combination with one or more other agents (e.g., insulin) that are useful in treasting diabetes.

Any glycogen phosphorylase inhibitor may be used as the second agent in combination with a Formula (I) compound of the present invention. The term glycogen phosphorylase inhibitor refers to compounds that inhibit the bioconversion of glycogen to glucose-1-phosphate, which is catalyzed by the enzyme glycogen phosphorylase. Such glycogen phosphorylase inhibition activity is readily determined by standard assays well known in the art (e.g., J. Med. Chem. 41 (1998) 2934-2938). Glycogen phosphorylase inhibitors of interest herein include those described in PCT patent application publication Nos. WO 96/39384 and WO 96/39385. The references cited above are incorporated herein by reference.

Aldose reductase inhibitors are also useful in the practice of the combination aspect of the present invention. These compounds inhibit the bioconversion of glucose to sorbitol, which is catalyzed by the enzyme aldose reductase. Aldose reductase inhibition is readily determined by standard assays (e.g., J. Malone, *Diabetes,* 29:861-864 (1980) "Red Cell Sorbitol, an Indicator of Diabetic Control", incorporated herein by reference). A variety of aldose reductase inhibitors are known to those skilled in the art. The reference cited above are incorporated herein by reference.

Any sorbitol dehydrogenase inhibitor may be used in combination with a Formula (I) compound of the present invention. The term sorbitol dehydrogenase inhibitor refers to compounds that inhibit the bioconversion of sorbitol to fructose, which is catalyzed by the enzyme sorbitol dehydrogenase. Such sorbitol dehydrogenase inhibitor activity is readily determined by the use of standard assays well known in the art (e.g., Analyt. Biochem (2000) 280: 329-331). Sorbitol dehydrogenase inhibitors of interest include those disclosed in U.S. Pat. Nos. 5,728,704 and 5,866,578. The references cited above are incorporated herein by reference.

Any glucosidase inhibitor can be used in the combination aspect of the present invention. Such compounds inhibit the enzymatic hydrolysis of complex carbohydrates by glycoside hydrolases such as amylase or maltase into bioavailable simple sugars, for example, glucose. The rapid metabolic action of glucosidases, particularly following the intake of high levels of carbohydrates, results in a state of alimentary hyperglycemia, which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214), incorporated herein by reference.

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by use of standard assays (e.g., Methods Enzymol. (1955)1: 149, incorporated herein by reference). The inhibition of such enzymatic degradation is beneficial in reducing amounts of bioavailable sugars, including glucose and maltose, and the concomitant deleterious conditions resulting therefrom.

Preferred glucosidase inhibitors include acarbose, adiposine, voglibose, miglitol, emiglitate, camiglibose, tendamistate, trestatin, pradimicin-Q and salbostatin. The glucosidase inhibitor acarbose and various amino sugar derivatives related thereto are disclosed in U.S. Pat. Nos. 4,062,950 and 4,174,439 respectively. The glucosidase inhibitor adiposine is disclosed in U.S. Pat. No. 4,254,256. The glucosidase inhibitor voglibose, 3,4-dideoxy-4-[[2-hydroxy-1-(hydroxymethyl)ethyl]amino]-2-C-(hydroxymethyl)-D-epi-inositol, and various N-substituted pseudoaminosugars related thereto are disclosed in U.S. Pat. No. 4,701,559. The glucosidase inhibitor miglitol, (2R,3R,4R,5S)-1-(2-hydroxyethyl)-2-(hydroxymethyl)-3,4,5-piperidinetriol, and various 3,4,5-trihydroxypiperidines related thereto are disclosed in U.S. Pat. No. 4,639,436. The glucosidase inhibitor emiglitate, ethyl p-[2-[(2R,3R,4R,5S)-3,4,5-trihydroxy-2-(hydroxymethyl)piperidinolethoxy]-benzoate, various derivatives related thereto and pharmaceutically acceptable acid addition salts thereof are disclosed in U.S. Pat. No. 5,192,772. The glucosidase inhibitor MDL-25637, 2,6-dideoxy-7-O-$\beta$-D-glucopyrano-syl-2,6-imino-D-glycero-L-gluco-heptitol, various homodisaccharides related thereto and the pharmaceutically acceptable acid addition salts thereof are disclosed in U.S. Pat. No. 4,634,765. The glucosidase inhibitor camiglibose, methyl 6-deoxy-6-[(2R,3R,4R,5S)-3,4,5-trihydroxy-2-(hydroxymethyl)piperidino]-$\alpha$-D-glucopyranoside sesquihydrate, deoxy-nojirimycin derivatives related thereto, various pharmaceutically acceptable salts thereof and synthetic methods for the preparation thereof are disclosed in U.S. Pat. Nos. 5,157,116 and 5,504,078. The glycosidase inhibitor salbostatin and various pseudosaccharides related thereto are disclosed in U.S. Pat. No. 5,091,524. All of the references cited above are incorporated herein by reference.

Amylase inhibitors of interest herein are disclosed in U.S. Pat. No. 4,451,455, U.S. Pat. No. 4,623,714 (Al-3688 and the various cyclic polypeptides related thereto) and U.S. Pat. No. 4,273,765 (trestatin, which consists of a mixture of trestatin A, trestatin B and trestatin C, and the various trehalose-containing aminosugars related theret). All of the references cited above are incorporated herein by reference.

Additional anti-diabetic compounds, which may be used as the second agent in combination with a Formula (I) compound of the present invention, include, for example, the following: biguanides (e.g., metformin, pfenformin or buformin), insulin secretagogues (e.g., sulfonylureas and glinides), glitazones, non-glitazone PPAR$\gamma$ agonists, PPAR$\beta$ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-$\beta$ inhibitors and AGE breakers.

The Formula (I) compounds of the present invention may also be used in combination with antihypertensive agents Preferred antihypertensive agents useful in the present invention include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

The additional pharmaceutical agent is preferably an anti-obesity agent as described above, but otherwise will frequently be an HMG-CoA reductase inhibitor, an HMG-CoA synthase inhibitor, an inhibitor of HMG-CoA reductase gene expression, a CETP inhibitor, a PPAR modulator, a squalene synthetase inhibitor, a squaline epoxidase inhibitor, a squaline cyclase inhibitor, a combined squaline epoxidase/cyclase inhibitor, a cholesterol absorption inhibitor, an ACAT inhibitor, a pancreatic lipase inhibitor, a gastric lipase inhibitor, a calcium channel blocker, an ACE inhibitor, a beta blocker, a diuretic, niacin, a garlic extract preparation, a bile acid sequestrant, a fibric acid derivative, a glycogen phosphorylase inhibitor, an aldose reductase inhibitor,a sorbitol dehydrogenase inhibitor, a glucosidase inhibitoran amylase inhibitor or a DPP-IV inhibitor.

Preferred HMG-CoA reductase inhibitors include lovastatin, simvastatin, pravastatin, fluvastatin, atorvastatin or rivastatin; more preferably, atorvastatin, particularly atorvastatin hemicalcium.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-obesity agent,) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

According to the methods of the invention, a compound of the present invention or a combination is preferably administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see *Reminaton: The Practice of Pharmacy*, Lippincott Williams and Wilkins, Baltimore Md., 20$^{th}$ ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycedes including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i)one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, from Abitec), Migyol™ 812 (caprylic/capric triglyceride, from Condea, Cranford N.J), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 μg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel®-102) (15.8%), sodium starch (7%), sodium lauryl sulfate (2%) and magnesium stearate (1%).

The HPMCAS polymers are available in low, medium and high grades as Aqoat®-LF, Aqoat®-MF and Aqoat®-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally. An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carder. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England) or may be prepared using methods known to those of average skill in the art from readily available materials.

General Experimental Procedures

NMR spectra were recorded on a Varian Unity™ 400 or 500 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. MS peaks are reported for all examples.

Optical rotations were determined on a PerkinElmer™ 241 polarimeter (available from PerkinEimer Inc., Wellesley, Mass.) using the sodium D line (λ=589 nm) at the indicated temperature and are reported as follows $[\alpha]_D^{temp}$, concentration (c=g/100 mL), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

In the discussion which follows, certain common abbreviations and acronyms have been employed which include: h (hour(s)), PyBroP (bromo-tris-pyrrolidino-phosphonium hexafluorophosphate), BOC (tert-butoxycarbonyl), DMSO (dimethyl sulfoxide), EtOAc (ethyl acetate), HOBT (1-hydroxybenzotriazole), EDC (1-ethyl-3-(dimethylaminopropyl)-carbodiimide hydrochloride), LAH (lithium aluminum hydride), Dess-Martin Periodinane (1,1,1-Triacetoxy-1,1-dihydro-1,2-benziodoxol-3(1H)-one), DIBAL (diisobutylaluminum hydride) and THF (tetrahydrofuran).

Preparation of Key Intermediates

Preparation of Intermediate Quinoline-6-carboxylic acid tert-butyl ester

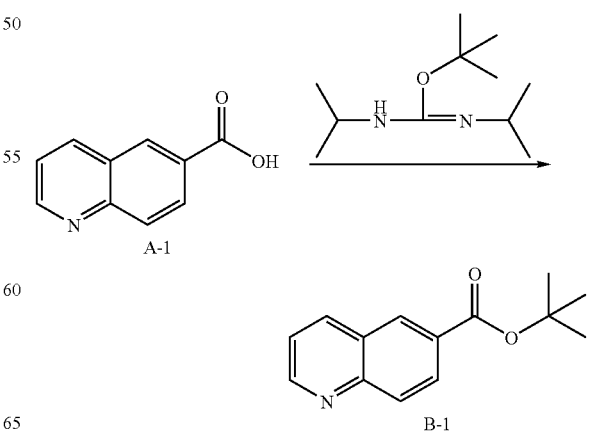

To a solution of 2-tert-butyl-1,3diisopropyl-isourea, prepared in accordance with the method described in Mathias, L. J., *Synthesis*, 1979, 561, (115 g, 575 mM, 5 equiv) in CH$_2$Cl$_2$ (200 mL) at 0° C., A-1 was added in one portion (19.9 g, 115 mM, 1 equiv). The ice-bath was removed and the mixture was allowed to warm to room temperature and was stirred at that temperature overnight (16 h). The mixture was cooled to 0° C. and a precipitate that formed was removed by filtration. The filtrate was washed with 10% aqueous citric acid, and aqueous NaHCO$_3$, dried over MgSO$_4$, filtered and concentrated to give B-1 as an oil. The oil was purified by filtration through a plug of silica gel, eluting with 20% ethyl acetate in hexanes.

$^1$H NMR (400 MHz, CD$_3$OD) δ=8.94 (dd, J=4.1, 1.7 Hz, 1H), 8.60 (d, J=1.7 Hz, 1H), 8.50 (d, J=8.3 Hz), 8.71 (d, J=1.7 Hz, 1H), 8.25 (dd, J=9.1, 2.1 Hz, 1H), 8.06 (d, J=9.1 Hz, 1H), 7.61 (dd, J=4.1, 8.3 Hz, 1H), 1.64 (s, 9H). MS 231 (m+1).

Prepartion of Intermediate
1-Oxy-quinoline-6-carboxylic acid tert-butyl ester

To a solution of quinoline-6-carboxylic acid tert-butyl ester (B-1, 22.0 g, 95.65 mM, 1 equiv) and urea-H$_2$O$_2$ complex (18.0 g, 191.3 mM, 2 equiv) in THF at 0° C. was added trifluoroacetic anhydride (27.1 mL, 191.3 mM, 2 equiv) dropwise over 20 minutes. The mixture was stirred at 0° C. for 1 h. The reaction was quenched with 1 M sodium thiosulfate (100 mL) and the mixture was stirred at room temperature for 15 minutes. A solution of 0.5 N HCl (200 mL) was added and the mixture was extracted 3 times with CH$_2$Cl$_2$. The combined CH$_2$Cl$_2$ fractions were washed with aqueous bicarbonate and water, dried (MgSO$_4$), filtered and concentrated to give a solid material. The solid was slurried in 90 mL EtOAc/hexanes (1:2) solution and stirred for 15 minutes. The product C-1 was collected by filtration and the mother liquor was concentrated. This procedure was repeated twice with the mother liquor, decreasing the volume of solvent by 0.5 each time. Total yield 23.61 g. The product was used without further purification.

$^1$H NMR (400 MHz, CDCl3) δ=8.79 (d, J=9.1 Hz), 8.65 (m, 2H), 8.27 (dd, J=9.1, 2.1 Hz, 1H), 7.89 (d, J=8.3 Hz, 1H), 7.41 (dd, J=8.3, 5.8 Hz), 1.62 (s, 9H)

Preparation of Intermediate
2-Amino-quinoline-6-carboxylic acid tert-butyl ester

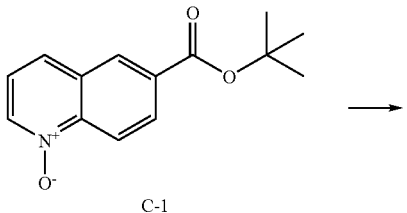

To a solution of 1-oxy-quinoline-6-carboxylic acid tert-butyl ester (C-1, 12.3 g, 50 mM, 1 equiv) in chloroform (120 mL) was added p-toluenesulfonyl chloride (12.4 g, 65 mM, 1.3 equiv). The mixture was stirred at room temperature for 30 minutes and then cooled to 0° C. Aqueous 10% NH$_4$OH (120 mL) was added in one portion and the mixture was stirred at 0° C. for 10 minutes and then allowed to warm to room temperature and stirred 3.5 h. The mixuture was poured into a separatory funnel and the layers were separated. The aqueous fraction was extracted twice with chloroform. The combined chloroform fractions were washed with water, dried (MgSO$_4$), filtered and concentrated to give a solid material. The solid was slurried in ethyl acetate (40 mL) and the product was collect by filtration to give 8.5 g of compound D-1. The mother liquor was concentrated by half and an additional crop of 2.25 g of product was collected. Total yield 10.75 g.

$^1$HNMR (400 MHz, CDCl$_3$) □=8.30 (d, 1.67 Hz, 1H), 8.19 (dd, J=8.7, 1.67 Hz, 1H), (d, J=8.7 Hz, 1H), 7.58 (d, J=8.7 Hz, 1H), 6.75 (d, J=8.7 Hz, 1H), 1.62 (s, 9H). MS 245 (M+1)

Preparation of intermediate quinoline-6-carboxylic acid benzyl ester

To a solution of quinoline-6-carboxylic acid (2.0 g, 11.6 mmol) in EtOAc (30 mL) was added carbonyldiimidazole (2.15 g, 13.3 mmol). The resulting mixture was stirred at room temperature for 2 h at which time all solids had dissolved. Benzyl alcohol (1.4 mL) was added and the reaction was stirred overnight. The mixture was then extracted successively vwth aqueous 1 N HCl (25 mL), aqueous NaHCO$_3$ and brine. Evaporation of the solvent gave a solid, which was triturated with cold 1:1 EtOAc/hexane to afford the title compound as a solid (1.9 g, 62%). $^1$H NMR (selected signals, CD$_3$OD) δ=9.00 (dd, 1H), 8.61 (d, 1H), 8.34 (d, 1H), 8.29 (dd, 1H), 8.25 (d, 1H), 5.43 (s, 2H)

Prepartion of intermediate
1-oxy-quinoline-6-carboxylic acid benzyl ester

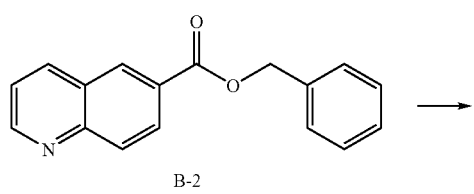

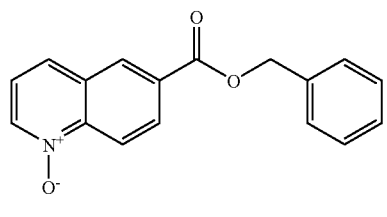

To a solution of quinoline-6-carboxylic acid benzyl ester (5 g, 18.9 mmol) and urea-H$_2$O$_2$ complex (3.0 q, 32 mmol) in CH$_2$Cl$_2$ (75 mL) was added phthalic anhydride (4 g, 26.7 mmol). The mixture was stirred at room temperature overnight. The reaction was quenched with 1 M sodium thiosulfate (25 mL) and the mixture was stirred at room temperature for 15 minutes. A solution of 0.5 N HCl (50 mL) was added. The organic layer was separated and washed with aq. NaHCO$_3$ and brine. Combined aqueous layers were extracted with EtOAc. Combined organic layers were concentrated to give a solid, which was triturated with cold 1:1 EtOAc/hexane to provide the title compound (4.8 g, 91%). $^1$H NMR (selected signals, CDCl$_3$) δ=8.79 (d, 1H), 8.63 (d, 1H), 8.58 (d, 1H), 8.35 (dd, 1H), 7.82 (d, 1H), 5.43 (s, 2H)

Preparation of Intermediate
2-Amino-quinoline-6-carboxylic acid benzyl ester

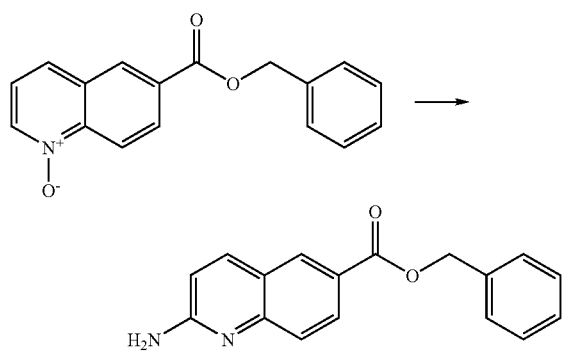

To a solution of 1-oxy-quinoline-6-carboxylic acid benzyl ester (10 g, 35.8 mmol) in CH$_2$Cl$_2$ (4 mL) was added p-toluenesulfonyl chloride (10 g, 53.6 mmol). The mixture was stirred at room temperature for 45 minutes. In a separate second flask, triethylamine (25 mL, 178 mmol) was added to a suspension of NH$_4$Cl (9.7 g, 178 mmol) in CH$_2$Cl$_2$. This mixture was stirred for 30 minutes and then added slowly to the first reaction mixture. Stirring was continued at room temperature for 1 h and then the reaction was cooled to 5° C. A solid was collected by filtration. This was slurried with water (100 mL) at room temperature. The title compound (4.8 g, 48%) was collected by filtration, washing with cold methanol. $^1$H NMR (DMSO-d$_6$): □=8.32 (d, 1H), 8.03 (d, 1H), 7.96 (dd, 1H), 7.47-7.32 (series of m, 6H), 6.86 (s, 2H), 6.78 (d, 1H), 5.34 (s, 2H).

Preparation of Intermediate 2-[(4'-Trifluoromethyl-biphenyl-2-carbonyl)-amino]-quinoline-6-carboxylic acid tert-butyl ester

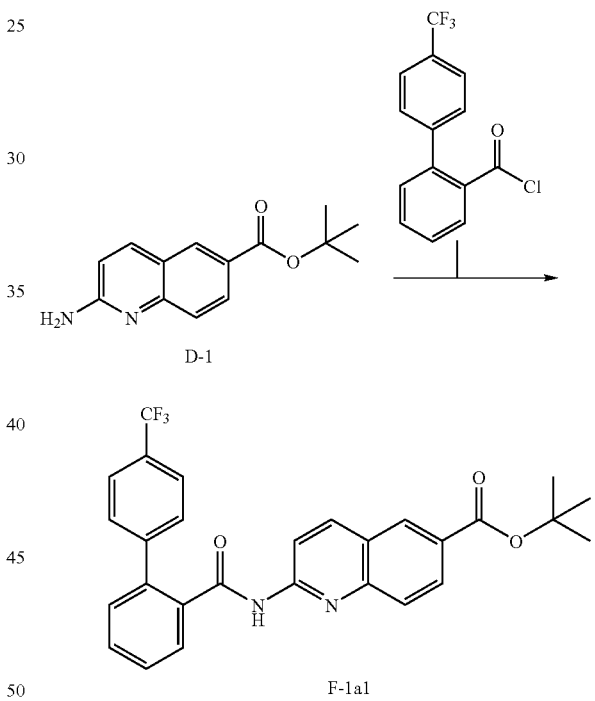

To a solution of 2-amino-quinoline-6-carboxylic acid tert-butyl ester (D-1, 4.68 g, 19.15 mM, 1.02 equiv) and pyridine (4.65 mL, 57.45 mM, 3 equiv) in CH$_2$Cl$_2$ (150 mL) was added dropwise a solution of the acid chloride (5.0 g, 18.78 mM, 1.0 equiv) in CH$_2$Cl$_2$ (40 mL). The mixture was stirred at room temperature for 2 h, transferred to a separatory funnel and washed with 1N HCl and water. The CH$_2$Cl$_2$ fraction was dried (Na$_2$SO$_4$), filtered and concentrated. The crude product was purified by column chromatography using 4:1 hexanes/ethyl acetate.

$^1$H NMR (400 MHz, CDCl$_3$) □=8.51 (d, J=1.7 Hz, 1H), 8.46 (d, J=8.7 Hz, 1H), 8.24 (d, J=9 Hz, 1H), 8.18 (d, J=8.7 Hz, 1H), 7.71 (d, J=7.9 Hz, 1H), 7.66-7.40 (m, 8H), 1.61 (s, 9H). MS 493 (M+1)

Preparation of Intermediate 2-[(4'-Trifluoromethyl-biphenyl-2-carbonylamino]-quinoline-6-carboxylic acid

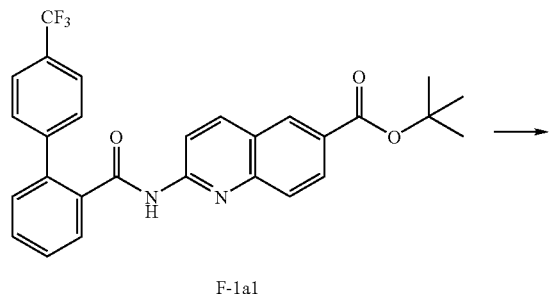

F-1a1

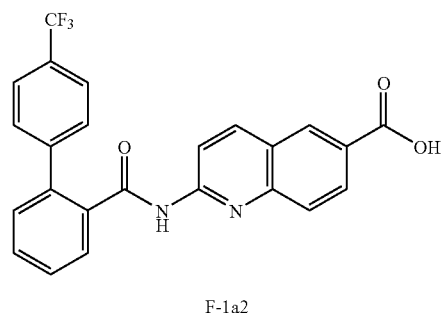

F-1a2

Intermediate 2-[(4'-trifluoromethyl-biphenyl-2-carbonyl)-amino]-quinoline-6-carboxylic acid tert-butyl ester (F-1a1, 9.0 g) was dissolved in 50 mL 4N HCl in dioxane and stirred at room temperature overnight. The solution was concentrated to provide compound F-1a2. The compound was used without further purification.

$^1$H NMR (400 MHz, d6-DMSO) □=11.49 g (s, 1H), 8.56 (d, J=2.1 Hz, 1H), 8.52 (d, J=9.1 Hz, 1H), 8.14 (dd, 1H, J=9.1, 1.9 Hz, 1H), 7.81 (d, J=8.7 Hz, 1H), 7.74-7.48 (m, 9H). MS 493 (M−1)

Preparation of Intermediate 2-[Methyl-(4'-trifluoromethyl-biphenyl-2-carbonyl)amino]-quinoline-6-carboxylic acid

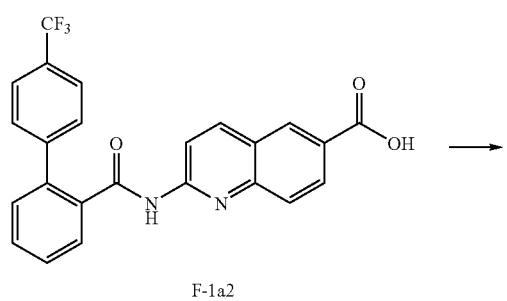

F-1a2

-continued

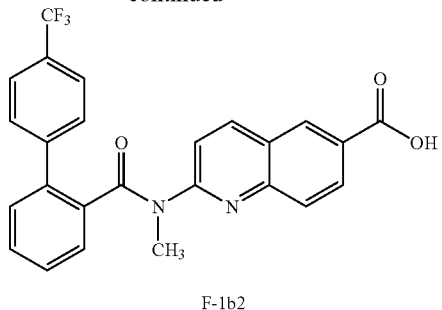

F-1b2

To a solution of 2-[(4'-trifluoromethyl-biphenyl-2-carbonyl)-amino]-quinoline-6-carboxylic acid (F-1a2, 200 mg, 0.46 mM) in toluene (3.0 mL) was added Bu$_4$NHSO$_4$ (15.6 mg, 0.046 mM) and freshly powdered K$_2$CO$_3$ (127 mg, 0.92 mM), and KOH (128 mg, 2.28 mM). The resulting suspension was stirred at room temperature for 1 h. The mixture was heated to 70° C. and (CH$_3$)$_2$SO$_4$ (95 uL, 1.01 mM) was added dropwise. The mixture was stirred at 70° C. for 2 h. LC/MS analysis revealed the residue to be a mixture of the acid F-1b2 and the corresponding methyl ester. After cooling to room temperature the mixture was concentrated and the residue was taken up in 5 mL of THF/methanol/H$_2$O (3:1:1) and the resulting mixture was stirred until the methyl ester had been completely consumed (2 h). The mixture was diluted with H$_2$O (5 mL) and the pH was adjusted to 2.0 with 1 N HCl. The mixture was extracted 3 times with EtOAc. The combined EtOAc fractions were dried (MgSO$_4$), filtered and concentrated to provide F-1b2 (180 mg) as a colorless solid.

Preparation of Intermediate 4'-tert-Butylbiphenyl-2-carboxylic acid ethyl ester

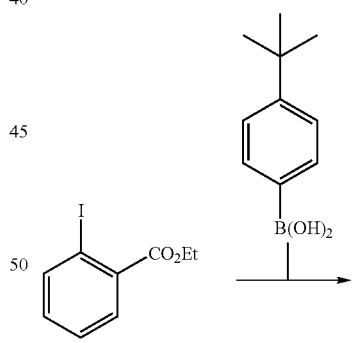

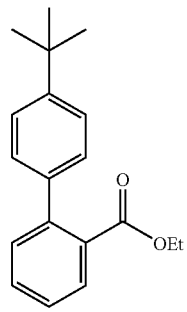

To a mixture of ethyl 2-iodobenzoate (32.3 g, 117 mmol), 4-tert-butylboronic acid (25 g, 140.4 mmol), cesium carbonate (91.22 g, 280 mmol) in dimethoxyethane (300 mL) was added tetrakistriphenylphosphine palladium (0) (1.0 g). The reaction mixture was heated to reflux for ~90 h, then cooled and taken up in water. The mixture was extracted three times with diethyl ether. The combined organic layers were washed with brine, dried over MgSO$_4$ and concentrated to afford the crude title compound as a brown oil (33 g). This was used directly in the next step without purification. $^1$H NMR (selected signals, CDCl$_3$): 8.18 (d, 1H), 7.80 (dd, 1H), 7.55 (d, 1H), 7.50 (d, 1H), 7.41 (d, 2H), 7.26 (d, 2H), 4.08 (q, 2H) 1.36 (s, 9H), 0.94 (t, 3H).

Preparation of Intermediate 4'-tert-Butylbiphenyl-2-carboxylic acid

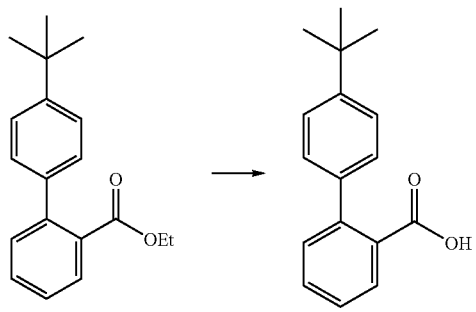

Crude 4'-tert-butylbiphenyl-2-carboxylic acid ethyl ester (33 g, ~117 mmol) was taken up in a mixture of THF (100 mL), methanol (50 mL) and water (40 mL). Lithium hydroxide monohydrate (7.36 g, 176 mmol) was added and the reaction mixture was allowed to stir at room temperature for 3 days. The mixture was extracted three times with diethyl ether. The aqueous phase was then acidified using aq. 6N HCl and extracted three times with EtOAc. The combined EtOAc layers were dried over MgSO$_4$, filtered and concentrated. The solid residue was triturated with hexane to afford the title compound as a white solid (18.7 g, 63%). $^1$H NMR (selected signals, DMSO-d$_6$): 7.66 (dd, 1H), 7.53 (m, 1H), 7.41 (d, 2H), 7.25 (d, 2H), 1.29 (s, 9 H).

Preparation of Intermediate 2-[(4'-tert-Butylbiphenyl-2-carbonyl)amino]quinoline-6-carboxylic acid benzyl ester

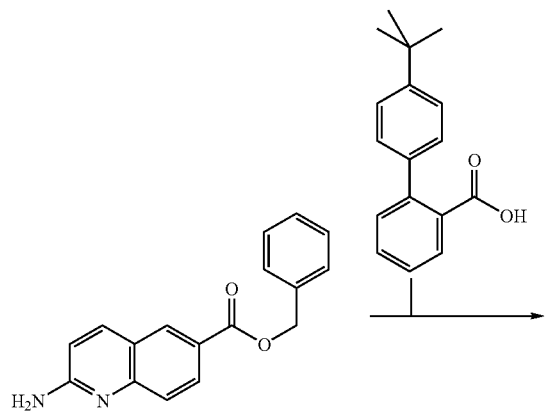

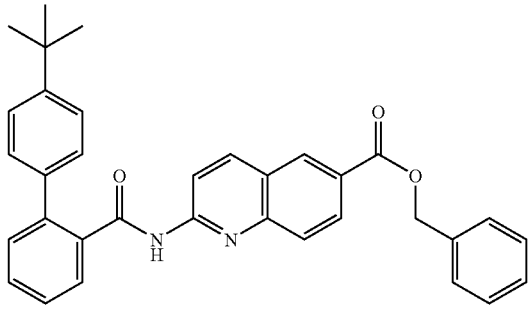

To solution of 2-aminoquinoline-6-carboxylic acid benzyl ester (25 g, 100 mmol) and 4'-tert-butylbiphenyl-2-carboxylic acid (19.5 g, 70 mmol) in CH$_2$Cl$_2$ (500 mL) was added 4-dimethylaminopyridine (9.77 g, 80 mmol) and 1-(3-dimethylaminopropyl)-3-ethylcarbodiimide hydrochloride (19.2 g, 100 mmol). The reaction mixture was stirred at room temperature for 18 h and then diluted with saturated aqueous NaHCO$_3$ solution. The aqueous phase was separated and extracted with CH$_2$Cl$_2$. Combined organic layers were washed with brine, dried over MgSO$_4$ and concentrated. The title compound (28.6 g, 79%) was isolated by column chromatography eluting with a gradient of 5% to 30% EtOAc in hexane.

Preparation of Intermediate 2-[(4'-tert-Butylbiphenyl-2-carbonyl)-amino]-quinoline-6-carboxylic acid

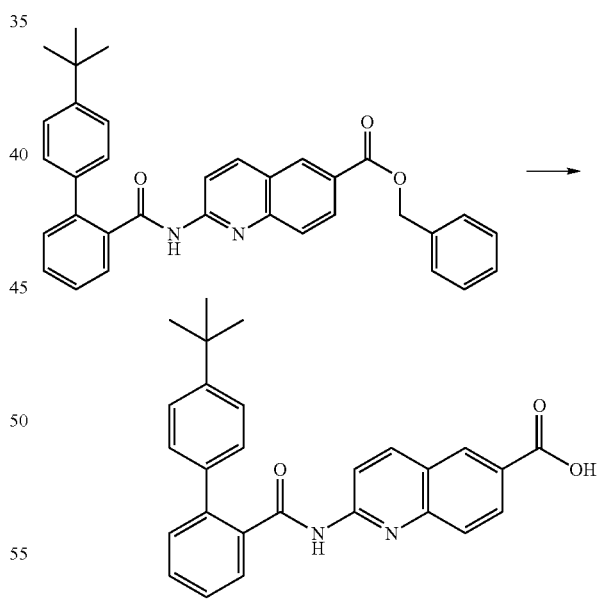

Lithium hydroxide monohydrate (3.5 g, 83.4 mmol) was added to a solution of 2-[(4'-tert-butylbiphenyl-2-carbonyl)-amino]-quinoline-6-carboxylic acid benzyl ester (28.6 g, 55.6 mmol) dissolved in methanol (220 mL), THF (110 mL) and water (83 mL). The reaction mixture was stirred at room temperature overnight and then concentrated under vacuum. The residue was taken up in water, and acidified using aqueous 6M HCl. The title compound (20.0 g, 85%) was collected by filtration, washing with Et$_2$O and drying The following intermediates were prepared from 2-aminoquinoline-6-carboxylic acid benzyl ester in an analogous manner to the preparation of the intermediate 2-[(4'-tert-butylbiphenyl-2-carbonyl)-amino]-quinoline-6-carboxylic acid benzyl ester:

2-[(4'-methylbiphenyl-2-carbonyl)-amino]-quinoline-6-carboxylic acid benzyl ester (by coupling with 4'-methylbiphenyl-2-carboxylic acid)

2-[(4'-ethylbiphenyl-2-carbonyl)-amino]-quinoline-6-carboxylic acid benzyl ester (by coupling with 4'-ethylbiphenyl-2-carboxylic acid)

2-[(4'-propylbiphenyl-2-carbonyl)-amino]-quinoline-6-carboxylic acid benzyl ester (by coupling with 4'-propylbiphenyl-2-carboxylic acid)

2-[(4'-isopropylbiphenyl-2-carbonyl)-amino]-quinoline-6-carboxylic acid benzyl ester (by coupling with 4'-isopropylbiphenyl-2-carboxylic acid)

2-[(4'-methoxybiphenyl-2-carbonyl)-amino]-quinoline-6-carboxylic acid benzyl ester (by coupling with 4'-methoxybiphenyl-2-carboxylic acid)

2-[(4'-ethoxybiphenyl-2-carbonylamino]-quinoline-6-carboxylic acid benzyl ester (by coupling with 4'-ethoxybiphenyl-2-carboxylic acid)

2-[(4'-isopropoxybiphenyl-2-carbonyl)-amino]-quinoline-6-carboxylic acid benzyl ester (by coupling with 4'-isopropoxybiphenyl-2-carboxylic acid)

2-[(4'-tert-butoxybiphenyl-2-carbonyl)-amino]-quinoline-6-carboxylic acid benzyl ester (by coupling with 4'-tert-butoxybiphenyl-2-carboxylic acid)

2-[(4'-methylthiobiphenyl-2-carbonyl)-amino]-quinoline-6-carboxylic acid benzyl ester (by coupling with 4'-methylthiobiphenyl-2-carboxylic acid)

2-[(6, 4'-dimethylbiphenyl-2-carbonyl)-amino]-quinoline-6-carboxylic acid benzyl ester (by coupling with 6, 4'-dimethylbiphenyl-2-carboxylic acid)

2-[(4'-isopropyl-6-methylbiphenyl-2-carbonyl)-amino]-quinoline-6-carboxylic acid benzyl ester (by coupling with 4'-isopropyl-6-methylbiphenyl-2-carboxylic acid)

2-[(4'-tert-butyl-6-methylbiphenyl-2-carbonyl)-amino]-quinoline-6-carboxylic acid benzyl ester (by coupling with 4'-tert-butyl-6-methylbiphenyl-2-carboxylic acid)

2-[(6-methyl-4'-trifluoromethylbiphenyl-2-carbonyl)-amino]-quinoline-6-carboxylic acid benzyl ester (by coupling with 6-methyl-4'-trifluoromethylbiphenyl-2-carboxylic acid)

2-[(6, 4'-dimethoxybiphenyl-2-carbonyl)-amino]-quinoline-6-carboxylic acid benzyl ester (by coupling with 6, 4'-dimethoxybiphenyl-2-carboxylic acid)

2-[(6-methoxy-4'-methylbiphenyl-2-carbonyl)-amino]-quinoline-6-carboxylic acid benzyl ester (by coupling with 6-methoxy-4'-methylbiphenyl-2-carboxylic acid)

2-[(4'-tert-butyl-6-methoxybiphenyl-2-carbonyl)-amino]-quinoline-6-carboxylic acid benzyl ester (by coupling with 4'-tert-butyl-6-methoxybiphenyl-2-carboxylic acid)

The following intermediates were prepared from the corresponding benzyl esters in a manner similar to the preparation of the intermediate 2-[(4'-tert-butylbiphenyl-2-carbonyl)-amino]-quinoline-6-carboxylic acid:

2-[(4'-methylbiphenyl-2-carbonyl)-amino]-quinoline-6-carboxylic acid

2-[(4'-ethylbiphenyl-2-carbonyl)-amino]-quinoline-6-carboxylic acid

2-[(4'-propylbiphenyl-2-carbonylamino]-quinoline-6-carboxylic acid

2-[(4'-isopropylbiphenyl-2-carbonyl)-amino]-quinoline-6-carboxylic acid

2-[(4'-methoxybiphenyl-2-carbonyl)-amino]-quinoline-6-carboxylic acid

2-[(4'-ethoxybiphenyl-2-carbonyl)-amino]-quinoline-6-carboxylic acid

2-[(4'-isopropoxybiphenyl-2-carbonyl)-amino]-quinoline-6-carboxylic acid

2-[(4'-tert-butoxybiphenyl-2-carbonyl)-amino]-quinoline-6-carboxylic acid

2-[(4'-methylthiobiphenyl-2-carbonyl)-amino]-quinoline-6-carboxylic acid

2-[(6, 4'-dimethylbiphenyl-2-carbonyl)-amino]-quinoline-6-carboxylic acid

2-[(4'-isopropyl-6-methylbiphenyl-2-carbonyl)-amino]-quinoline-6-carboxylic acid 2-[(4'-tert-butyl-6-methylbiphenyl-2-carbonyl)-amino]-quinoline-6-carboxylic acid 2-[(6-methyl-4'-trifluoromethylbiphenyl-2-carbonyl)-amino]-quinoline-6-carboxylic acid 2-[(6, 4'-dimethoxybiphenyl-2-carbonyl)-amino]-quinoline-6-carboxylic acid 2-[(6-methoxy-4'-methylbiphenyl-2-carbonyl)-amino]-quinoline-6-carboxylic acid 2-[(4'-tert-butyl-6-methoxybiphenyl-2-carbonyl)-amino]-quinoline-6-carboxylic acid Example 1

(S)-2-[(4'-Trifluoromethyl-biphenyl-2-carbonyl)-amino]-quinoline-6-carboxylic acid (pentylcarbamoyl-phenyl-methyl)-amide.

(a) Preparation of Intermediate (S)-2-Amino-N-pentyl-2-phenyl-acetamide hydrochloride

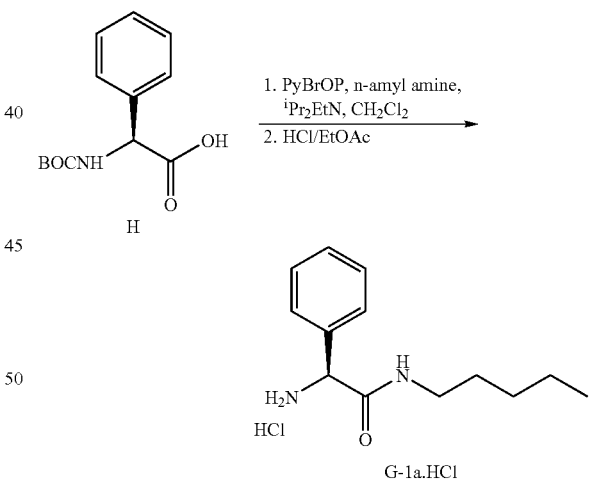

PyBrOP (2.2 g, 4.78 mM), and N-Boc-phenylglycine (H, 1.2 g, 4.78 mM) were taken up in $CH_2Cl_2$ (25 mL) and cooled to 0° C. N-Amylamine was added and the resulting mixture was treated with diisopropylethylamine (2.5 mL, 14.3 mM). The mixture was allowed to warm to room temperature and was stirred at this temperature for 2 h. The mixture was diluted with EtOAc and washed with 1 N HCl, water and brine. The organic fraction was dried ($Na_2SO_4$), filtered and concentrated. The product was purified by column chromatography eluting with 1:1 EtOAc/hexanes to give 1.19 g, of (S)-2-amino-N-pentyl-2-phenyl-acetamide hydrochloride.

The product above was taken up in 5 volumes of 4N HCl in dioxane and stirred at room temperature for 30 minutes. The solution was concentrated to a foam and dried under high vacuum overnight.

$^1$H NMR (400 MHz, CD$_3$OD) δ=7.48 (m, 5H), 4.88 (s, 1H), 3.25 (m, 1H), 3.15 (m, 1H), 1.45 (m, 2H), 1.24 (m, 2H), 1.17 (m, 2H), 0.38 (t, J=7.1 Hz, 3H)

(b) Preparation of (S)-2-[(4'-Trifluoromethyl-biphenyl-2-carbonyl)-amino]-quinoline-6-carboxylic acid (pentylcarbamoyl-phenyl-methyl)-amide.

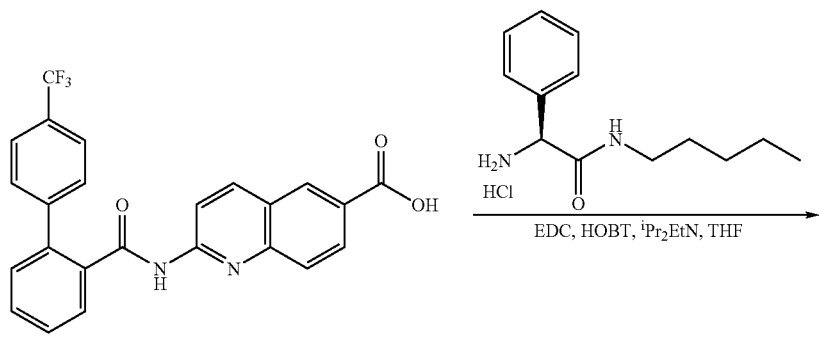

F-1a2

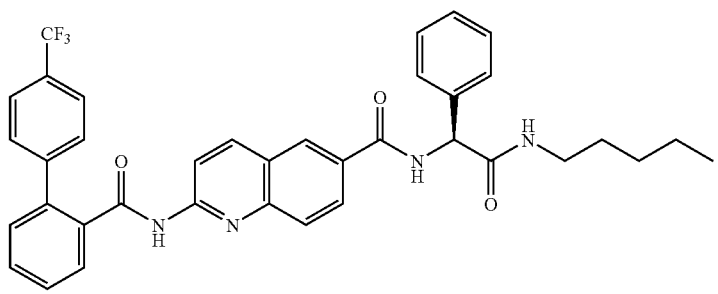

2-[(4'-Trifluoromethyl-biphenyl-2-carbonyl)-amino]-quinoline-6-carboxylic acid (F-1a2, 1.2 g, 2.53 mM), EDC (0.79 g, 6.34 mM), HOBT (0.86 g, 6.34 mM) and (S)-2-amino-N-pentyl-2-phenyl-acetamide hydrochloride (0.78 g, 3.05 mM,) were combined and dissolved in THF (12.5 mL). The mixture was treated with diisopropylethylamine (2.20 mL, 13 mM) and stirred at room temperature for 16 h. The mixture was diluted with CH$_2$Cl$_2$ and washed with water. The CH$_2$Cl$_2$ fraction was dried (Na$_2$SO$_4$), filtered and concentrated. The product was purified by flash chromatography, eluting with 30% acetone in hexanes to give 1.36 g of (S)-2-[(4'-trifluoromethyl-biphenyl-2-carbonyl)-amino]-quinoline-6-carboxylic acid (pentylcarbamoyl-phenyl-methyl)amide as an amorphous solid.

$^1$H NMR (400 MHz, CDCl$_3$) □=8.24 (d, J=[1.4 Hz, 1H), 8.21 (d, J=9.1 Hz, 1H), 8.03 (dd, J=8.7, 1.7 Hz, 1H), 7.87 (d, J=6.4 Hz, 1H), 7.80 (d, J=7.2 Hz, 1H), 7.71 (d, J=8.9 Hz, 1H), 7.65-7.33 (overlapping m, 12H), 5.77 (t, J=5.7 Hz, 1H), 5.63 (d, J=6.5 Hz, 1H), 3.25 (dt, J=7.1, 5.7 Hz, 2H), 1.44 9m, 2H), 1.25 (m, 2H), 1.17 (m, 2H), 0.83 (t, J=7.2 Hz, 3H), ESMS 639 (m+1)

(c) Preparation of Crystalline Form A of (S-2-[(4'-Trifluoromethyl-biphenyl-2-carbonyl)-amino]-quinoline-6-carboxylic acid (phenylcarbamoyl-phenyl-methyl)-amide (S)-2-[(4'-Trifluoromethyl-biphenyl-2-carbonyl)-amino]-quinoline-6-carboxylic acid (pentylcarbamoyl-phenyl-methyl)-amide (100 mg), prepared as described in Example 1(b), was dissolved with heating in a 7:1 mixture of ethanol/water (20 mL). The mixture was allowed to cool to room temperature and stirred at this temperature for 48 h. The solid was collected by filtration. Yield 86 mg.

Analysis of form A by fusion microscopy revealed a melting event at an onset temperature of 179° C.

(d) Preparation of Crystalline Form B of (S)-2-[(4'-Trifluoromethyl-biphenyl-2-carbonyl)-amino]-quinoline-6-carboxylic acid (pentylcarbamoyl-phenyl-methyl)-amide (S)-2-[(4'-Trifluoromethyl-biphenyl-2-carbonyl)-amino]-quinoline-6-carboxylic acid (pentylcarbamoyl-phenyl-methyl)-amide (100 mg), prepared as described in Example 1(b), was dissolved with heating in a 1:1 mixture of ethyl acetate and hexanes (10 mL). The mixture was allowed to cool to room temperature and stirred at this temperature for 48 h. The solid was collected by filtration. Yield 78 mg.

Analysis of form B by fusion microscopy revealed a melting event at an onset temperature of 187° C.-

Alternative preparation of (S)-2-[(4'-Trifluoromethyl-biphenyl-2-carbonyl)-amino]-quinoline-6-carboxylic acid (pentylcarbamoyl-phenyl-methyl)-amide (a) Preparation of Intermediate 1-Oxy-quinoline-6-carboxylic acid benzyl ester

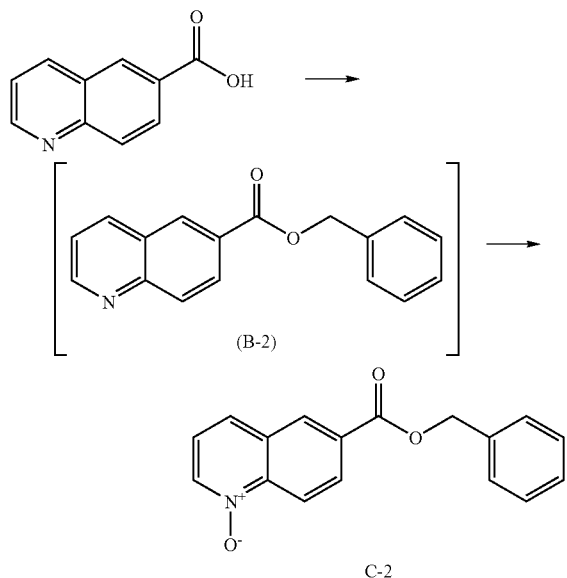

1,1'-Carbonyldiimidazole (51.56 g, 0.318 moles) was added to a slurry of 6-quinoline carboxylic acid (50 g, 0.289 moles) in 2-methyltetrahydrofuran (500 mL). The reaction mixture was then heated to 40° C. to 45° C. and held at that temperature for two to six hours. The reaction mixture was then cooled to 20° C. to 25° C., and benzyl alcohol (34.39 g, 0.318 moles) was added. The reaction mixture was then stirred for 10 to 18 hours at 20° C. to 25° C., then washed successively with 2 N HCl (300 mL), an aqueous solution of NaHCO$_3$ (300 mL), and an aqueous solution of NaCl (350 mL). A 95% yield (72.23 g, 0.274 moles) of the resulting benzyl ester product (B-2) was assumed for the reaction solution. The 2-methyltetrahydrofuran was then displaced under vacuum with 1,2-dichloroethane to final a reaction volume of 725 mL. To the reaction mixture was then added 2-methyltetrahydrofuran (1,100 mL), phthalic anhydride (105.76 g, 0.714 moles), and urea hydrogen peroxide complex (44.16 g, 0.469 moles). The resulting slurry was then stirred for 24 to 36 hours at 20° C. to 25° C. To the reaction mixture was then added aqueous sodium thiosulfate (900 mL) and 2-methyltetrahydrofuran (360 mL), and the whole was then stirred for 1 hour at 20° C. to 25° C. An aqueous solution of 2N HCl was added, the reaction mixture was stirred and organic and aqueous layers were separated. The organic layer was then washed two times with an aqueous solution of NaHCO$_3$ (1,825 mL, 725 mL) and once with an aqueous solution of NaCl (365 mL). The organic product layer was then vacuum concentrated, and the reaction solvents were exchanged for ethyl acetate to a final volume of 260 mL. To the resulting reaction slurry was added hexanes (450 mL) and the reaction mixture was cooled to 0° C. to 5° C. and stirred for 3 to 8 hours. The product (C-2) was collected by filtration (73.15 g, 95% yield).

Intermediate (B-2): $^1$H NMR (selected signals, DMSO-d$_6$) δ=9.00 (dd, 1H), 8.73 (d, 1H), 8.60 (d, 1H), 8.23 (dd, 1H), 8.11 (d, 1H), 5.41 (s, 2H)
Product: (C-2) $^1$H NMR (selected signals, DMSO-d$_6$) δ=8.79 (s, 1H), 8.69 (d, 1H), 8.61 (d, 1 H), 8.25 (d, 1H), 8.16 (d, 1H), 5.42 (s, 2H)

(b) Preparation of Intermediate 2-Amino-quinoline-6-carboxylic acid benzyl ester

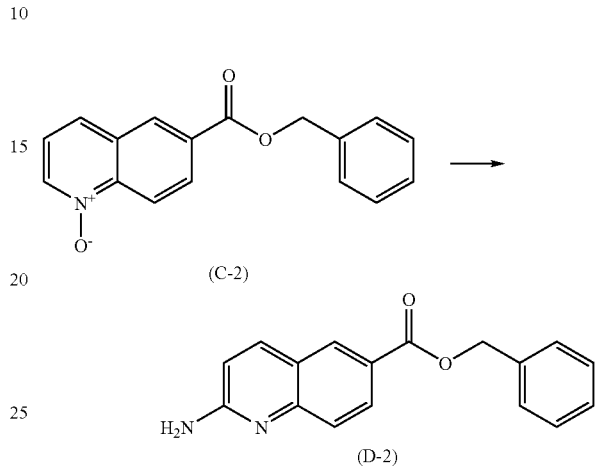

To a solution of 1-oxy-quinoline-6-carboxylic acid benzyl ester (114.29 g, 0.409 moles) in 1,2-dichloroethane (1,368 mL) was added p-toluenesulfonyl chloride (109.24 g, 0.573 moles). The reaction mixture was stirred for one to four hours at 20° C. to 25° C. In a separate reactor, triethylamine (135.04 g, 1.334 moles) was added to a slurry of ammonium chloride (65.63 g, 1.227 moles) in 1,2-dichloroethane (342 mL). The ammonium chloride slurry was then cooled to −5° C. to −10° C. The p-toluenesulfonyl chloride solution was then added over three to four hours to the ammonium chloride slurry which was maintained at −10° C. to −5° C. The reaction mixture was stirred for 8 to 16 hours at −10° C. to −5° C., and product obtained by filtration. The product was then slurried in water (1,150 mL) for 8 to 16 hours at 20° C. to 25° C. and isolated by filtration (62.33 g, 55% yield).
$^1$H NMR (DMSO-d$_6$) δ=8.32 (d, 1H), 8.03 (d, 1H), 7.97 (dd, 1H), 7.48-7.32 (series of m, 6H), 6.87 (s, 2H), 6.78 (d, 1H), 5.34 (s, 2H)

(c) Preparation of Intermediate 2-Amino-quinoline-6-carboxylic acid potassium salt

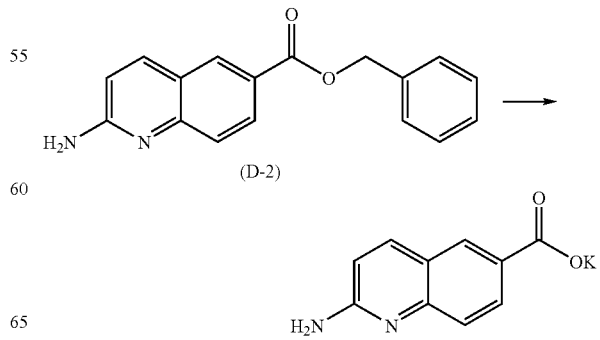

A mixture of 2-amino-quinoline-6-carboxylic acid benzyl ester (15.63 g, 0.0562 moles), 2-propanol (235 mL), water (15.6 mL) and potassium hydroxide (6.3 g, 0.112 moles) was heated to reflux, 80° C. to 85° C., for 2 to 4 hours. The reaction mixture was then cooled to 20° C. to 25° C., vacuum concentrated (volume of 160 mL) and granulated at 20° C. to 25° C. for 8 to 16 hours. The product was isolated by filtration (12.08 g, 0.0534 moles, 95% yield).

$^1$H NMR (selected signals, D$_2$O) δ=7.86 (d, 1H), 7.75 (dd, 1H), 7.66 (d, 1H), 7.20 (d, 1H), 6.50 (d, 1H)

(d) Preparation of Intermediate (S)-2-Amino-quinoline-6-carboxylic acid pentylcarbamoyl-phenyl-methyl)-amide

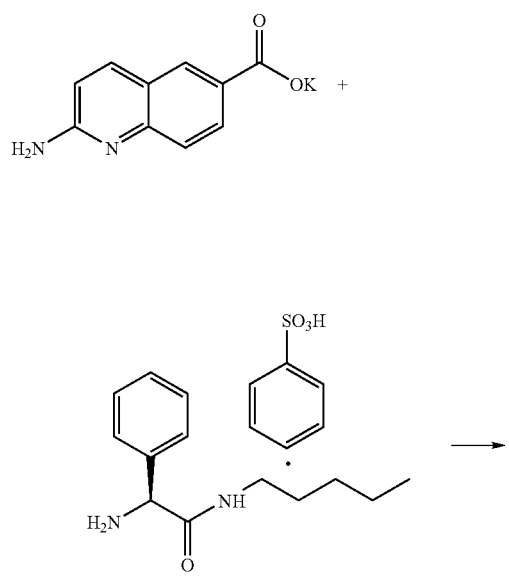

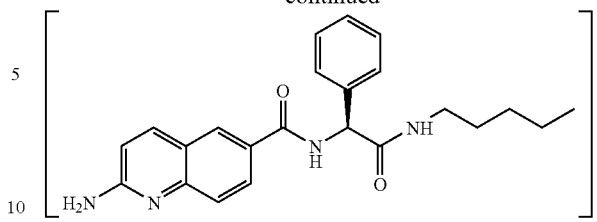

Residual water in the 2-amino-quinoline-6-carboxylic acid potassium salt (5.0 g, 0.0221 moles) was displaced with tetrahydrofuran (4×100 mL) by concentration under vacuum (final reaction volume 105 mL). 1-(3-Dimethylaminopropyl)-3-ethyl-carbodiimide hydrochloride (5.33 g, 0.0195 moles) was added to the tetrahydrofuran solution and the reaction slurry was stirred for 15 to 60 minutes at 20° C. to 25° C. To this was added (S)-2-amino-N-pentyl-2-phenyl-acetamide, benzene sulfonate (7.39 g, 0.0195 moles) and (S)-2-amino-N-pentyl-2-phenyl-acetamide (0.97 g, 0.0044 moles), and the reaction mixture was stirred for 12 to 24 hours at 20° C. to 25° C. The tetrahydrofuran was displaced with ethyl acetate (3×100 MI) by concentration under vacuum. After the final concentration, to give an oil, sufficient ethyl acetate was added to obtain a solution (final reaction mixture volume 260 mL). Aqueous sodium bicarbonate (250 mL) and activated carbon (5.09, Darco G-60) were added to the ethyl acetate solution and the whole was stirred for 2 to 3 hours at 20° C. to 25° C. The mixture was filtered to remove activated carbon and the aqueous and organic filtrate layers were separated. The organic layer was washed twice with water (2×100 mL). Residual water in the product solution was displaced at atmospheric pressure with ethyl acetate and the product was isolated as an ethyl acetate solution with a yield of 90% assumed (6.86 g, 0.0176 moles).

$^1$H NMR (selected signals, DMSO-d$_6$) δ=8.65 (d, 1H), 8.24 (dd, 1H), 7.93 (d, 1H), 7.49 (t, 1H), 7.39 (t, 1H), 7.34-7.23 (series of m, 5H).

(e) Preparation of (S)-2-[(4'-Trifluoromethyl-biphenyl-2-carbonyl)-amino]-quinoline-6-carboxylic acid (pentylcarbamoyl-phenyl-methyl)-amide

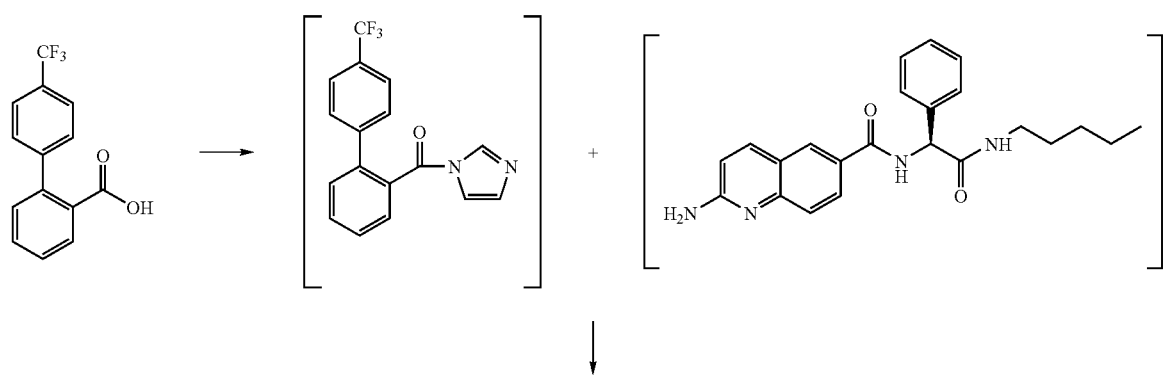

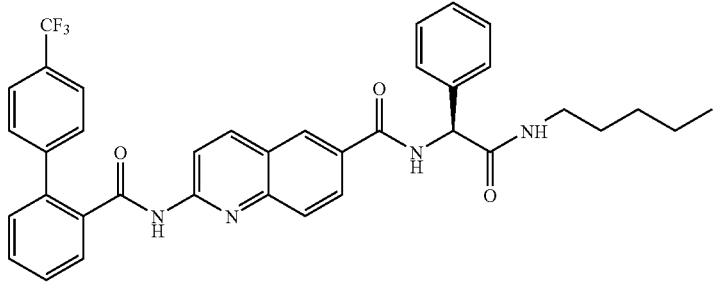

A mixture of 4'-trifluoromethyl-biphenyl-2-carboxylic acid (7.03 g, 0.0264 moles), ethyl acetate (70 mL) and 1,1'-carbonyldiimidazole (4.28 g, 0.0264 moles) was heated to 75° C. to 80° C. for 3 to 6 hours, then cooled to 20° C. to 25° C. and added to the ethyl acetate solution of the 2-aminoquinoline derivative obtained in Step (d) above. The reaction mixture was heated to 75° C. to 80° C. for 115 to 135 hours. Ethyl acetate (70 mL) was added and the whole was washed three times with water (3×210 ml). Residual water in the reaction mixture was displaced at atmospheric pressure with ethyl acetate, then the ethyl acetate was displaced with 2B ethanol (final reaction volume 100 mL). To the reaction slurry, water (10.5 mL) was added, and the mixture was stirred at 20° C. to 25° C. for 4 to 16 hours. The product was isolated by filtration (6.18 g, 55% yield).

$^1$H NMR (selected signals, DMSO-$d_6$) δ=11.32 (s, 1 H ), 8.95 (d, 1H), 8.54 (d, 1H), 8.41 (d, 1 H), 8.28 (t, 1H), 8.18-8.11 (series m, 2H), 7.77-7.25 (series of m, 13H). X-ray powder diffraction and differential scanning calorimetry showed the product to be crystalline form A The compounds in Table 1(a) were prepared using procedures analogous to those described above for the synthesis of the compound of Example 1 using appropriately substituted starting materials/intermediates which are available commercially, prepared in a manner analogous to the methods described above for other intermediates, or prepared using procedures known to those of average skill in the art.

TABLE 1(a)

| Ex. No. | Compound Name | HPLC Retention time (or selected NMR signals) | ESMS (m + 1) | Calc MW |
|---|---|---|---|---|
| 2 | (S)-2-[(4'-trifluoromethyl-biphenyl-2-carbonyl)-amino]-quinoline-6-carboxylic acid (carbamoyl-phenyl-methyl)-amide | 2.70 | 569 | 568 |
| 3 | (S)-2-[(4'-trifluoromethyl-biphenyl-2-carbonyl)-amino]-quinoline-6-carboxylic acid (methylcarbamoyl-phenyl-methyl)-amide | 2.77 | 583 | 582 |
| 4 | 2-[(4'-trifluoromethyl-biphenyl-2-carbonyl)-amino]-quinoline-6-carboxylic acid [phenyl-(2,2,2-trifluoro-ethylcarbamoyl)-methyl]-amide | 2.85 | 651 | 650 |
| 5 | (S)-2-[(4'-trifluoromethyl-biphenyl-2-carbonyl)-amino]-quinoline-6-carboxylic acid [(ethyl-methyl-carbamoyl)-phenyl-methyl]-amide | 2.52 | 611 | 610 |
| 6 | (S)-2-[(4'-trifluoromethyl-biphenyl-2-carbonyl)-amino]-quinoline-6-carboxylic acid (diethylcarbamoyl-phenyl-methyl)-amide | 2.52 | 625 | 624 |
| 7 | (S)-2-[(4'-trifluoromethyl-biphenyl-2-carbonyl)-amino]-quinoline-6-carboxylic acid (phenyl-propylcarbamoyl-methyl)-amide | 2.48 | 611 | 610 |
| 8 | (S)-2-[(4'-trifluoromethyl-biphenyl-2-carbonyl)-amino]-quinoline-6-carboxylic acid (dipropylcarbamoyl-phenyl-methyl)-amide | 3.00 | 653 | 652 |
| 9 | (S)-2-[(4'-trifluoromethyl-biphenyl-2-carbonyl)-amino]-quinoline-6-carboxylic acid (isopropylcarbamoyl-phenyl-methyl)-amide | 2.58 | 611 | 610 |
| 10 | S)-2-[(4'-trifluoromethyl-biphenyl-2-carbonyl)-amino]-quinoline-6-carboxylic acid [(ethyl-isopropyl-carbamoyl)-phenyl-methyl]-amide | | | 638 |
| 11 | 2-[(4'-trifluoromethyl-biphenyl-2-carbonyl)-amino]-quinoline-6-carboxylic acid (butylcarbamoyl-phenyl-methyl)-amide | | | 624 |
| 12 | (S)-2-[(4'-trifluoromethyl-biphenyl-2-carbonyl)-amino]-quinoline-6-carboxylic acid [(butyl-methyl-carbamoyl)-phenyl-methyl]-amide | 3.05 | 639 | 638 |

TABLE 1(a)-continued

| Ex. No. | Compound Name | HPLC Retention time (or selected NMR signals) | ESMS (m + 1) | Calc MW |
|---|---|---|---|---|
| 13 | 2-[(4'-trifluoromethyl-biphenyl-2-carbonyl)-amino]-quinoline-6-carboxylic acid [(butyl-ethyl-carbamoyl)-phenyl-methyl]-amide | | | 652 |
| 14 | 2-[(4'-trifluoromethyl-biphenyl-2-carbonyl)-amino]-quinoline-6-carboxylic acid [(butyl-ethyl-carbamoyl)-phenyl-methyl]-amide | | | 652 |
| 15 | (S)-2-[(4'-trifluoromethyl-biphenyl-2-carbonyl)-amino]-quinoline-6-carboxylic acid (isobutylcarbamoyl-phenyl-methyl)-amide | 2.87 | 625 | 624 |
| 16 | 2-[(4'-trifluoromethyl-biphenyl-2-carbonyl)-amino]-quinoline-6-carboxylic acid (pentylcarbamoyl-phenyl-methyl)-amide | 2.85 | 639 | 638 |
| 17 | (S)-2-[methyl-(4'-trifluoromethyl-biphenyl-2-carbonyl)-amino]-quinoline-6-carboxylic acid (pentylcarbamoyl-phenyl-methyl)-amide | | | 652 |
| 18 | (S)-2-[methyl-(4'-trifluoromethyl-biphenyl-2-carbonyl)-amino]-quinoline-6-carboxylic acid [(methyl-pentyl-carbamoyl)-phenyl-methyl]-amide | | | 666 |
| 19 | (S)-2-[(4'-trifluoromethyl-biphenyl-2-carbonyl)-amino]-quinoline-6-carboxylic acid [(methyl-pentyl-carbamoyl)-phenyl-methyl]-amide | 3.0 | 653 | 652 |
| 20 | (S)-2-[(4'-trifluoromethyl-biphenyl-2-carbonyl)-amino]-quinoline-6-carboxylic acid [(5-hydroxy-pentylcarbamoyl)-phenyl-methyl]-amide | 2.60 | 655 | 654 |
| 21 | (S)-2-[(4'-trifluoromethyl-biphenyl-2-carbonyl)-amino]-quinoline-6-carboxylic acid (hexylcarbamoyl-phenyl-methyl)-amide | | | 653 |
| 22 | (S)-2-[(4'-trifluoromethyl-biphenyl-2-carbonyl)-amino]-quinoline-6-carboxylic acid [(cyclohexyl-methyl-carbamoyl)-phenyl-methyl]-amide | 3.3 | 666 | 665 |
| 23 | (S)-2-[(4'-trifluoromethyl-biphenyl-2-carbonyl)-amino]-quinoline-6-carboxylic acid [(cyclohexyl-ethyl-carbamoyl)-phenyl-methyl]-amide | 3.43 | 680 | 679 |
| 24 | (S)-2-[(4'-trifluoromethyl-biphenyl-2-carbonyl)-amino]-quinoline-6-carboxylic acid [(cyclohexylmethyl-carbamoyl)-phenyl-methyl]-amide | 3.23 | 665 | 664 |
| 25 | (S)-2-[(4'-trifluoromethyl-biphenyl-2-carbonyl)-amino]-quinoline-6-carboxylic acid (benzylcarbamoyl-phenyl-methyl)-amide | 2.78 | 659 | 658 |
| 26 | (S)-2-[(4'-trifluoromethyl-biphenyl-2-carbonyl)-amino]-quinoline-6-carboxylic acid [(benzyl-methyl-carbamoyl)-phenyl-methyl]-amide | 3.22 | 673 | 672 |
| 27 | 2-[(4'-trifluoromethyl-biphenyl-2-carbonyl)-amino]-quinoline-6-carboxylic acid {[3-(2-oxo-pyrrolidin-1-yl)-propylcarbamoyl]-phenyl-methyl}-amide | 2.97 | 693 | 692 |
| 28 | (S)-2-[(4'-trifluoromethyl-biphenyl-2-carbonyl)-amino]-quinoline-6-carboxylic acid [phenyl-(pyridin-4-ylcarbamoyl)-methyl]-amide | 2.68 | 646 | 645 |
| 29 | (S)-2-[(4'-trifluoromethyl-biphenyl-2-carbonyl)-amino]-quinoline-6-carboxylic acid [phenyl-(pyridin-3-ylcarbamoyl)-methyl]-amide | 2.86 | 646 | 645 |
| 30 | (S)-2-[(4'-trifluoromethyl-biphenyl-2-carbonyl)-amino]-quinoline-6-carboxylic acid [phenyl-(2-pyridin-2-yl-ethylcarbamoyl)-methyl]-amide | 2.97 | 673 | 674 |
| 31 | (S)-2-[(4'-trifluoromethyl-biphenyl-2-carbonyl)-amino]-quinoline-6-carboxylic acid [phenyl-(2-pyridin-4-yl-ethylcarbamoyl)-methyl]-amide | 3.05 | 673 | 674 |
| 32 | (S)-2-[(4'-trifluoromethyl-biphenyl-2-carbonyl)-amino]-quinoline-6-carboxylic acid (2-oxo-1-phenyl-2-pyrrolidin-1-yl-ethyl)-amide | 2.86 | 624 | 625 |

TABLE 1(a)-continued

| Ex. No. | Compound Name | HPLC Retention time (or selected NMR signals) | ESMS (m + 1) | Calc MW |
|---|---|---|---|---|
| 33 | (S)-2-[(4'-trifluoromethyl-biphenyl-2-carbonyl)-amino]-quinoline-6-carboxylic acid (2-oxo-1-phenyl-2-piperidin-1-yl-ethyl)-amide | 3.17 | 638 | 637 |
| 34 | (S)-2-[methyl-(4'-trifluoromethyl-biphenyl-2-carbonyl)-amino]-quinoline-6-carboxylic acid (2-oxo-1-phenyl-2-piperidin-1-yl-ethyl)-amide | | | 650 |
| 35 | (S)-2-[(4'-trifluoromethyl-biphenyl-2-carbonyl)-amino]-quinoline-6-carboxylic acid (2-morpholin-4-yl-2-oxo-1-phenyl-ethyl)-amide | 2.90 | 640 | 639 |
| 36 | (S)-2-[methyl-(4'-trifluoromethyl-biphenyl-2-carbonyl)-amino]-quinoline-6-carboxylic acid [2-(4-ethyl-piperazin-1-yl)-2-oxo-1-phenyl-ethyl]-amide | | | 679 |
| 37 | (S)-2-[methyl-(4'-trifluoromethyl-biphenyl-2-carbonyl)-amino]-quinoline-6-carboxylic acid [2-oxo-1-phenyl-2-(4-propyl-piperazin-1-yl)-ethyl]-amide | | | 693 |
| 38 | (S)-[2-Phenyl-2-({2-[(4'-trifluoromethyl-biphenyl-2-carbonyl)amino]-quinoline-6-carbonyl}amino)acetylamino]-acetic acid methyl ester | 5.72(d, 1H); 4.04(m, 2H); 3.72(s, 3H) | 641 | 640.6 |
| 39 | (S)-{Methyl-[phenyl-({2-[(4'-trifluoromethylbiphenyl-2-carbonyl)amino]-quinoline-6-carbonyl}-amino)-acetyl]amino}-acetic acid methyl ester | 6.12(d, 0.8H); 5.86(d, 0.2H); 3.72(s, 2.4H); 3.54(s, 0.6H); 3.03(s, 0.6H); 2.96(2.4H) | 655 | 654.6 |
| 40 | (S)-3-[2-Phenyl-2-({2-[(4'-trifluoromethylbiphenyl-2-carbonyl)amino]-quinoline-6-carbonyl}-amino)acetylamino]-propionic acid methyl ester | 5.57(d, 1H); 3.60(s, 3H) | 655 | 654.6 |
| 41 | (S)-4-{[2-Phenyl-2-({2-[(4'-trifluoromethylbiphenyl-2-carbonyl)amino]-quinoline-6-carbonyl}-amino)-acetylamino]-methyl}-benzoic acid methyl ester | 5.69(d, 1H); 4.53(t, 2H); 3.89(s, 3H) | 717 | 716.7 |
| 42 | (S)-4-({Methyl-[phenyl-({2-[(4'-trifluoromethylbiphenyl-2-carbonyl)-amino]-quinoline-6-carbonyl}amino)-acetyl]-amino}-methyl)-benzoic acid benzyl ester | 6.07(d, 1H); 5.32(s, 2H); 2.90(s, 0.9H); 2.85(2.1H) | 807 | 806.8 |
| 43 | (S)-4-({Methyl-[phenyl-({2-[(4'-trifluoromethylbiphenyl-2-carbonyl)-amino]-quinoline-6-carbonyl}amino)-acetyl]-amino}-methyl)-benzoic acid methyl ester | 6.08(m, 1H); 3.90(s, 3H); 2.94(s, 0.9H); 2.89(2.1H) | 731 | 730.7 |
| 44 | (S)-4-[2-Phenyl-2-({2-[(4'-trifluoromethylbiphenyl-2-carbonyl)-amino]-quinoline-6-carbonyl}-amino)acetylamino]-butyric acid benzyl ester | 5.54(d, 1H); 5.06(s, 2H) | 745 | 744.8 |
| 45 | (S)-4-[2-Phenyl-2-({2-[(4'-trifluoromethylbiphenyl-2-carbonyl)amino]-quinoline-6-carbonyl}-amino)-acetylamino]-butyric acid methyl ester | | 669 | 668.7 |
| 46 | (S)-2-[(4'-Trifluoromethyl-biphenyl-2-carbonyl)amino]quinoline-6-carboxylic acid {[(4-fluorobenzyl)methyl-carbamoyl]phenylmethyl}amide | NMR: 6.13(d, 0.3H); 6.07(d, 0.7H); 2.90(s, 0.9H); 2.85(s, 2.1H); | 691 | 690.7 |

The compounds in Table (1b) were prepared using procedures analogous to those described above for the synthesis of the compound of Example 1 except that compound (F-1b2) was used in place of compound (F-1a2) as the starting material.

TABLE 1(b)

| Ex. No. | Compound Name | ESMS (M + 1) | Calc MW | $^1$H NMR |
|---|---|---|---|---|
| 47 | (S)-2-[methyl-(4'-trifluoromethyl-biphenyl-2-carbonyl)-amino]-quinoline-6-carboxylic acid [(butyl-methyl-carbamoyl)-phenyl-methyl]-amide | 654 | 653 | (500MHz, CDCl$_3$) δ=8.18(s, 1H), 8.05(t, J=6.7Hz, 1H), 7.995(dd, J=8.8, 1.8Hx, 1H), 7.76-7.72(m, 2H), 7.75-7.28(m, 11H), 7.1(m, 1H), 6.95(br s, 1H), 6.07 and 6.04 rotamers(1:1)[6.07(d, J=6.7Hz), 6.04(d, J=7.0Hz), 1H], 3.40(s, 3H), 3.3(m, 1H), 3.01 and 2.94 rotamers(2s, 3H), 2.92 and 2.85 rotamers(2s, 3H), 1.54-1.46(m, 2H), 1.33-1.24(m, 2H), 0.96-0.81(m, 3H) |
| 48 | (S)-2-[methyl-(4'-trifluoromethyl-biphenyl-2-carbonyl)-amino]-quinoline-6-carboxylic acid (benzylcarbamoyl-phenyl-methyl)-amide | 674 | 673 | (500MHz, CDCl$_3$) δ=8.1(s, 1H), 7.85-7.75(m, 2H), 7.56(m, 2H), 7.45-6.65(m, 18H), 5.835 and 5.570 rotamers(approx 4:1) [major 5.835(d, J=6.7Hz), minor 5.57(d, J=6.9Hz), 4.36(m, 2H), 3.31(s, 3H) |
| 49 | (S)-2-[methyl-(4'-trifluoromethyl-biphenyl-2-carbonyl)-amino]-quinoline-6-carboxylic acid [(ethyl-propyl-carbamoyl)-phenyl-methyl]-amide | 653 | 652 | (500MHz, CDCl$_3$) δ=8.32(s, 1H), 8.05(m, 2h), 7.60-7.25(m, 11H), 7.10(m, 1H), 6.9(br s, 1H), 6.09(d, J=7.0Hz, 1H), 3.40(s, 3H), 3.35(m, 2H), 3.23(m, 2H), 1.81(m, 2H)), 0.91(t, J=7.2Hz, 3H)), 0.82(t, J=7.3Hz, 3H) |
| 50 | (S)-2-[methyl-(4'-trifluoromethyl-biphenyl-2-carbonyl)-amino]-quinoline-6-carboxylic acid [(methyl-propyl-carbamoyl)-phenyl-methyl]-amide | 639 | 638 | (500MHz, CDCl$_3$) δ=8.09(s, 1H), 7.98-7.89(m, 2H), 7.70-7.60(m, 2H), 7.5-7.0(m, 13H), 6.00 and 5.95 rotamers(1:1.4)[.inor 6.00(d, J=7.7Hz), major 5.95(d, J=7.0Hz), 1H], 3.43(m, 1H)3.33(s, 3H), 3.25(m, 1H), 2.93 and 2.84 rotamers(2 s, 3H), 1.5(m, 2H), 0.8(m, 3H) |
| 51 | (S)-2-[methyl-(4'-trifluoromethyl-biphenyl-2-carbonyl)-amino]-quinoline-6-carboxylic acid [(ethyl-methyl-carbamoyl)-phenyl-methyl]-amide | 625 | 624 | (500MHz, CDCl$_3$) δ=8.08(s, 1H), 7.96-7.90(m, 2H), 7.76-7.66(m, 2H), 7.48-7.20(m, 11H), 7.05(d, J=7.0Hz, 1H), 6.89(br s, 1H), 6.00 and 5.96 rotamers(approx 1:1.3) [minor 6.00(d, J=7.3Hz), major 5.96(d, J=7.0Hz), 1H], 3.42 and 3.21 rotamers(2m, 2H), 3.32(s, 3H), 2.93 and 2.83 rotamers(2s, 3H), 1.18 and 0.87 rotamers([major 1.18 9t, J=7.3Hz), minor 0.87(t, J=6.0Hz), 3H] |
| 52 | (S)-2-[methyl-(4'-trifluoromethyl-biphenyl-2-carbonyl)-amino]-quinoline-6-carboxylic acid (cyclopropylcarbamoyl-phenyl-methyl)-amide | 624 | 623 | (500MHz, CDCl$_3$) δ=8.20(s, 1H), 7.85(m, 1H), 7.80(m, 1H), 7.75, 7.60(m, 2H), 7.5-7.25(m, 10H), 7.06(m, 1H), 6.9(br s, 1H), 6.42(s, 1H), 5.68(d, J=6.7Hz, 1H), 3.32(s, 3H), 2.64(m, 1H), 0.69(m, 2H), 0.38(m, 2H) |
| 53 | (S)-2-[methyl-(4'-trifluoromethyl-biphenyl-2-carbonyl)-amino]-quinoline-6-carboxylic acid (isobutylcarbamoyl-phenyl-methyl)-amide | 639 | 638 | (500MHz, CDCl$_3$) rotamers(4:1) some signals doubled δ=8.15(s, 1H), 7.92(dd, J=7.0, 1.9Hz, 1H), 7.85(d, J=6.5Hz, 1H), 7.70(d, J=8.3Hz, 1H), 7.65(d, J=6.5Hz, 1H), 7.49-7.19(m, 11H), 7.04(m, 1H), 8.86(m, 1H), 6.13 and 5.88 rotamers [major 6.13(m), 5.88(m), 1H)], 5.69 and 5.45 rotamers [major 5.69(d, J=6.5Hz), minor 5.45(d, J=6.5Hz), 1H], 3.32(s, 3H), 3.07(m, 1H), 2.95(m, 1H), 0.74(d, J=2.3Hz, 3H), 0.715(d, J=2.3Hz, 3H), 0.66(m, 1H) |

TABLE 1(b)-continued

| Ex. No. | Compound Name | ESMS (M + 1) | Calc MW | $^1$H NMR |
|---|---|---|---|---|
| 54 | (S)-2-[methyl-(4'-trifluoromethyl-biphenyl-2-carbonyl)-amino]-quinoline-6-carboxylic acid(phenyl-propylcarbamoyl-methyl)-amide | 626 | 625 | (500MHz, CDCl$_3$) δ=8.10(s, 1H), 7.92(dd, 8.8, 1.8Hz, 1H), 7.83(d, J=6.5Hz, 1H), 7.70-7.63(m, 2H), 7.49-7.25(m, 10H), 7.04(m, 1H), 6.9(m, 1H), 6.19-5.92 rotamers(5:1) [major 6.19(m), minor(5.92(m), 1H], 5.68-5.44 rotamers [major 5.65(d, j=6.5Hz), minor (5.44(d, J=7.3Hz), 1H], 3.32(s, 3H), 3.15(m, 2h), 1.37(m, 2H), 0.74(m, 3H) |
| 55 | (S)-2-[methyl-(4'-trifluoromethyl-biphenyl-2-carbonyl)-amino]-quinoline-6-carboxylic acid(2-morpholin-4-yl-2-oxo-1-phenyl-ethyl)-amide | 653 | 652 | (500MHz, CD$_3$OD) δ=8.30(s, 1H), 8.03(d, j=8.8Hz, 1H), 7.95(m, 1H), 7.70(d, j=7.5Hz, 1H), 7.54-7.37(m, 11H), 7.20(bs s, 1H), 7.05(br s, 1H), 6.79(br s, 1H), 6.14(3, 1H), 3.74-3.70(m, 2H), 3.63-3.55(n, 4H), 3.40(s, 3H), 3.32(m, 4H), 3.15(m, 1H) |
| 56 | (S)-2-[methyl-(4'-trifluoromethyl-biphenyl-2-carbonyl)-amino]-quinoline-6-carboxylic acid(2-oxo-1-phenyl-2-pyrrolidin-1-yl-ethyl)-amide | 637 | 636 | (500MHz, CD$_3$OD) δ=8.91(d, J=5.0Hz, 1H), 8.31(s, 3H), 8.04(dd, 8.8, 2.0Hz, 1H), 7.96(d, J=8.6Hz, 1H), 7.70(d, J=7.5Hz, 1H), 7.54-7.36(m, 12H), 7.20(br s, 1H), 7.05(br s, 1H), 5.93(m, 1H), 3.78(m, 1H), 3.60(m, 1H), 3.44(m, 1H), 3.40(s, 3H), 3.20(m, 1H), 2.05-1.80(m, 4H) |
| 57 | (S)-2-[methyl-(4'-trifluoromethyl-biphenyl-2-carbonyl)-amino]-quinoline-6-carboxylic acid [(cyclohexylmethyl-carbamoyl)-phenyl-methyl]-amide | 680 | 679 | (500MHz, CDCl$_3$), δ=8.10(s, 1H), 7.92(d, J=8.0Hz, 1H), 7.825(d, J=5Hz, 1H), 7.7(br s, 1H), 7.63(d, J=8.0Hz, 1H), 7.47-7.24(m, 11H), 7.05(br s, 1H), 6.90(br s, 1H), 6.02(t, j=6.0Hz, 1H), 5.65(d, J=6.3Hz, 1H), 3.32(s, 3H), 3.04(m, 2H), 1.77(m, 1H), 1.58-1.48(m, 4H), 1.38-1.30(m, 2H), 1.08-0.98(m, 2H), 0.78-0.70(m, 2H) |
| 58 | (S)-2-[methyl-(4'-trifluoromethyl-biphenyl-2-carbonyl)-amino]-quinoline-6-carboxylic acid [(benzyl-methyl-carbamoyl)-phenyl-methyl]-amide | 688 | 687 | (500MHz, CDCl$_3$) rotamers(2:1) some signals doubled δ=8.09(s, 1H), 7.93(m, 2h), 7.69(br s, 1H), 7.65(d, J=d, J=7.5Hz, 1H), 7.49-7.19(m, 14H), 7.11(m, 2H), 7.03(br s, 1H), 6.90(m, 1H), 6.08 and 6.02 rotamers [minor 6.07(d, J=7.6Hz), major 6.03(d, J=8.0Hz), 1H], 4.60 and 4.40 rotamers [major 4.6(m), minor 4.40(m), 2H], 3.32(s, 3H), 2.88 and 2.80 rotamers [minor 2.88(s), major 2.80(s), 3H] |

Example 59

Preparation of (S)-4'-Trifluoromethyl-biphenyl-2-carboxylic acid (6-{[(diethylcarbamoyl-phenyl-methyl)-amino]-methyl}-quinolin-2-yl)-amide (a) Preparation of Intermediate 4'-Trifluoromethyl-biphenyl-2-carboxylic acid (6-formyl-quinolin-2-yl)-amide

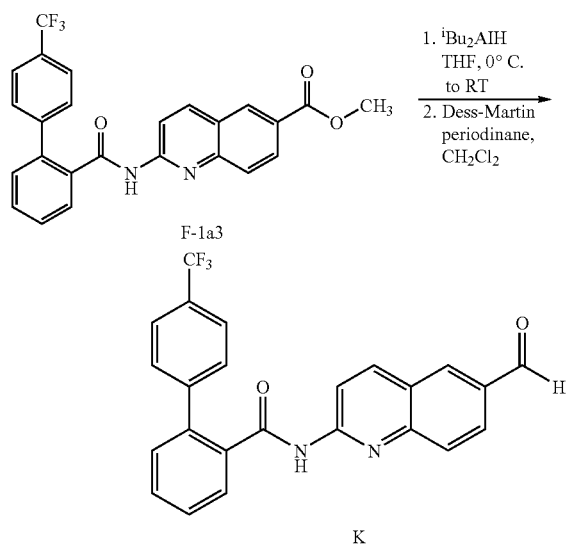

To a solution of the ester (F-1a3, 1.04 g, 2.74 mM) in THF (10 mL) at 0° C. was added dropwise a solution of DIBAL (1.0 M in THF, 8 mL). The mixture was allowed to slowly warm to room temperature and was stirred at that temperature for 12 H. The reaction was quenched with aqueous NaHCO$_3$ and the mixture was extracted 3 times with EtOAc. The combined EtOAc fractions were washed with brine and dried (Na$_2$SO$_4$). The mixture was filtered and concentrated to provide the corresponding alcohol as a white solid (0.93 g). The alcohol was used without further purification.

The alcohol product (0.772 g, 1.83 mM) from the above reaction was dissolved in CH$_2$Cl$_2$ and Dess-Martin periodinane (0.67 g, 1.83 mM). The mixture was stirred at room temperature for 12 h. The reaction was quenched with aqueous 1N Na$_2$S$_2$O$_3$ (10 mL) and aqueous NaHCO$_3$ (10 mL), and the resulting heterogeneous mixture was stirred vigorously for 15 min. The mixture was poured into a separatory funnel and the CH$_2$Cl$_2$ fraction was removed. The aqueous fraction was extracted with CH$_2$Cl$_2$. The combined CH$_2$Cl$_2$ fractions were dried (MgSO$_4$), filtered, and concentrated to provide 0.6 g of the corresponding aldehyde K. The product was used in the next step without further purification.

$^1$H NMR (500 MHz, CDCl$_3$) □=10.18 (s, 1H), 8.51 (d, J=8.8 Hz, 1H), 8.32 (d, J=8.8 Hz, 1H), 8.29 9d, J=2.1 Hz, 1H), 8.13 (dd, J=8.8, 2.1 Hz, 1H), 7.83-7.47 (overlapping m, 9H)

(b) Preparation of (S)-4'-Trifluoromethyl-biphenyl-2-carboxylic acid (6-{[(diethylcarbamoyl-phenyl-methyl)amino]-methyl}-quinolin-2-yl)-amide

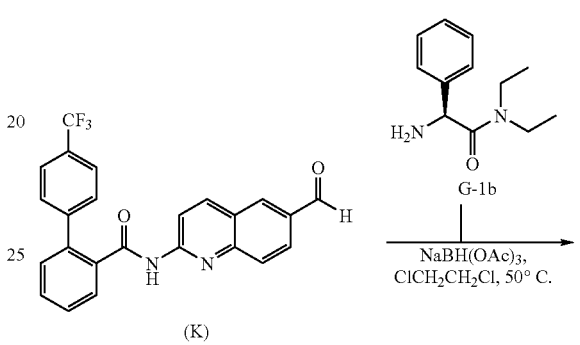

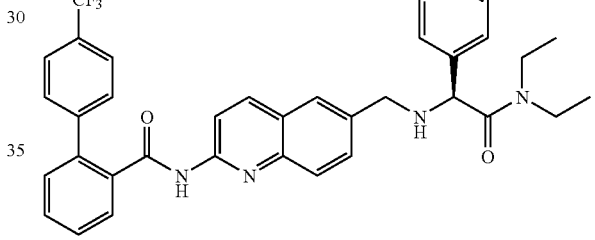

To a solution of 4'-trifluoromethyl-biphenyl-2-carboxylic acid (6-formyl-quinolin-2-yl)-amide (K, 118 mg, 0.28 mM) in dichloroethane (2.5 mL) was added the amine hydrochloride salt of G-1b (0.42 mM, 1.5 equiv) followed by triethylamine (58 uL, 0.42 mM). Sodium triacetoxy borohydride was added and the mixture was stirred at 50° C. for 16 h. After cooling to room temperature the mixture was applied directly to a small silica gel column. The product was eluted with 75% EtOAc in hexanes. HPLC retention time, 1.74 min; ESMS (M+1), 611; calc. Mw, 610

The compounds in Table 2 were prepared from appropriate starting materials using procedures analogous to those for the synthesis of the compound of Example 59.

TABLE 2

| Ex. No. | Compound Name | HPLC Retention time | ESMS (m + 1) | Calc. Mol. Wgt. |
|---|---|---|---|---|
| 60 | (S)-4'-trifluoromethyl-biphenyl-2-carboxylic acid [6-({[(benzyl-methyl-carbamoyl)-phenyl-methyl]-amino}-methyl)-quinolin-2-yl]-amide | 2.60 | 659 | 658 |
| 61 | (S)-4'-trifluoromethyl-biphenyl-2-carboxylic acid [6-({[(butyl-methyl-carbamoyl)-phenyl-methyl]-amino}-methyl)-quinolin-2-yl]-amide | 2.62 | 625 | 624 |

TABLE 2-continued

| Ex. No. | Compound Name | HPLC Retention time | ESMS (m + 1) | Calc. Mol. Wgt. |
|---|---|---|---|---|
| 62 | (S)-4'-trifluoromethyl-biphenyl-2-carboxylic acid [6-({[(methyl-pentyl-carbamoyl)-phenyl-methyl]-amino}-methyl)-quinolin-2-yl]-amide | 2.73 | 640 | 639 |
| 63 | (S)-4'-trifluoromethyl-biphenyl-2-carboxylic acid (6-{[(pentylcarbamoyl-phenyl-methyl)-amino]-methyl}-quinolin-2-yl)-amide | 2.73 | 626 | 625 |

Example 64

Preparation of (S)-4'-Trifluoromethyl-biphenyl-2-carboxylic acid (6-{[(diethylcarbamoyl-phenyl-methyl)-methyl-amino]-methyl}-quinolin-2-yl)-amide

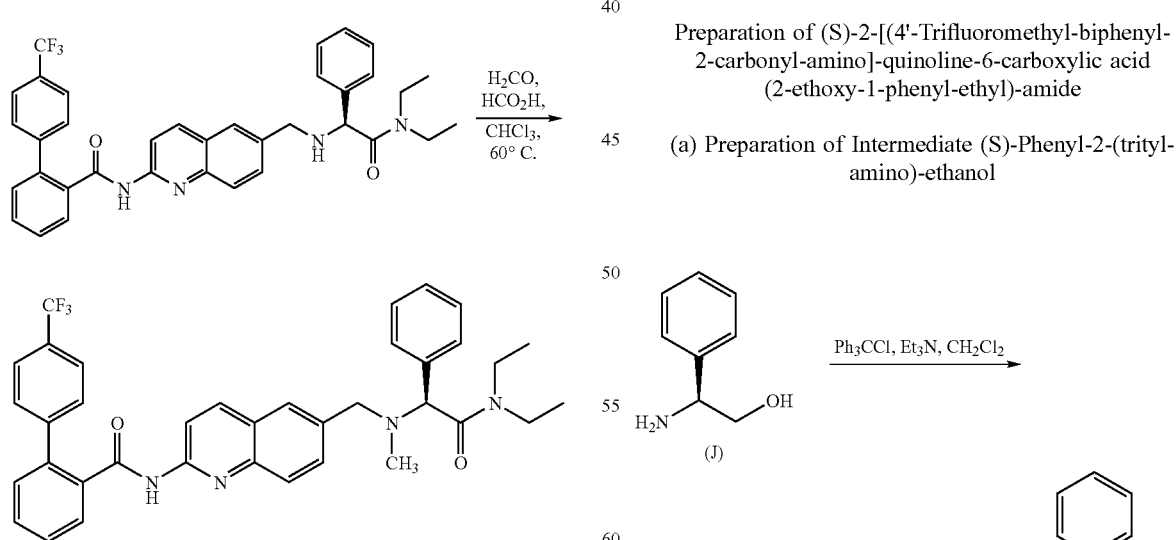

To a solution of the amine (0.1 mM) in CHCl₃ (2 mL) was added formic acid (0.15 mM) and aqueous formaldehyde (0.3 mM) and the mixture was heated to 60° C. for 12 h. After cooling to room temperature the mixture was diluted with ethyl acetate and washed with aqueous NaHCO₃ and brine, dried (MgSO₄), filtered and concentrated to provide the title compound. HPLC retention time, 2.46 min; ESMS (m+1), 625; calc. Mw, 624.

The compounds in Table 3 were prepared from appropriate starting materials using procedures analogous to those for the synthesis of the compound of Example 55.

TABLE 3

| Ex. No. | Compound Name | HPLC Retention time | ESMS (m + 1) | Calc. Mol. Wgt. |
|---|---|---|---|---|
| 65 | (S)-4'-trifluoromethyl-biphenyl-2-carboxylic acid [6-({[(butyl-methyl-carbamoyl)-phenyl-methyl]-methyl-amino}-methyl)-quinolin-2-yl]-amide | 2.62 | 639 | 638 |
| 66 | 4'-trifluoromethyl-biphenyl-2-carboxylic acid [6-({[(benzyl-methyl-carbamoyl)phenylmethyl]-methyl-amino}-methyl)-quinolin-2-yl]-amide | 2.79 | 673 | 672 |
| 67 | (S)-4'-trifluoromethyl-biphenyl-2-carboxylic acid [6-({methyl-[(methyl-pentyl-carbamoyl)-phenyl-methyl]-amino}-methyl)-quinolin-2-yl]-amide | 2.67 | 653 | 653 |
| 68 | (S)-4'-trifluoromethyl-biphenyl-2-carboxylic acid (6-{[methyl-(pentylcarbamoyl-phenyl-methyl)-amino]-methyl}-quinolin-2-yl)-amide | 2.80 | 639 | 638 |

Example 69

Preparation of (S)-2-[(4'-Trifluoromethyl-biphenyl-2-carbonyl-amino]-quinoline-6-carboxylic acid (2-ethoxy-1-phenyl-ethyl)-amide (a) Preparation of Intermediate (S)-Phenyl-2-(tritylamino)-ethanol

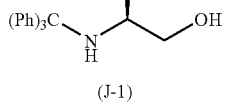

To a mixture of (S)-(+)-phenylglycinol (J, 1.0 g, 7.3 mM) and triphenylmethyl chloride (2.03 g, 7.29 mM) in dichloromethane (25 mL) was added triethylamine (0.74 g, 7.29 mM). The resulting mixture was stirred at room temperature for 12 h. The mixture was diluted with ethyl acetate (75 mL) and washed with water and brine. The ethyl acetate fraction was dried (MgSO$_4$), filtered and concentrated. The solid was used without further purification.

$^1$H NMR (500 MHz, CDCl$_3$) δ=7.53-7.51 (m, 5H), 7.28-7.15 9m, 15H), 3.81 (s, 1H), 3.23 (m, 1H), 2.80 (m,1H)

(b) Preparation of Intermediate
(S)-2-Ethoxy-1-phenyl-ethylamine hydrochloride (S)-Phenyl-2-(trityl-amino)-ethanol (J-1, 0.1 g, 0.26 mM), was dissolved in THF (3 mL). Sodium hydride (25 mg, 1.05 mM) was added and the mixture was stirred at room temperature for 15 minutes. The ethyl bromide (0.52 mM) was added and the mixture was heated to 50° C. for 4 h. The reaction was quenched with water and the mixture was diluted with ethyl acetate. The ethyl acetate fraction was dried (MgSO$_4$) filtered and concentrated. The residue was purified by flash chromatography (silica gel), eluting with EtOAc/hexanes.

The product from the above reaction was treated with 4M HCl/dioxane (2 mL). After stirring for 30 minutes at room temperature the mixture was concentrated and dried under high vacuum to provide the title compound.

(c) Preparation of (S)-2-[(4-Trifluoromethyl-biphenyl-2-carbonyl)-amino]-quinoline-6-carboxylic 2-ethoxy-1-phenyl-ethyl)-amide

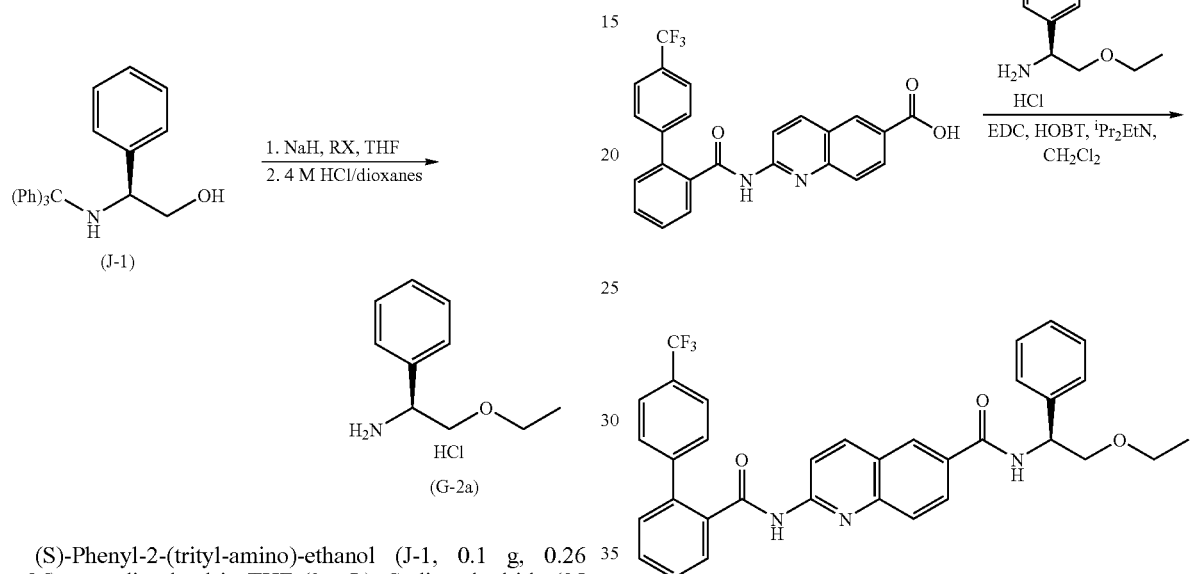

This compound was prepared in a manner analogous to that described in Example 1(b). HPLC retention time 2.21 min; ESMS (m+1), 584; calc. Mw, 583

The compounds in Table 4 were prepared from appropriate starting materials using procedures analogous to those described in Example (1b).

TABLE 4

| Ex. No. | Compound Name | HPLC Retention time | ESMS (m + 1) | Calc. Mol. Wgt. |
|---|---|---|---|---|
| 70 | (S)-2-[(4'-trifluoromethyl-biphenyl-2-carbonyl)-amino]-quinoline-6-carboxylic acid (2-methoxy-1-phenyl-ethyl)-amide | 2.10 | 571 | 570 |
| 71 | (S)-2-[(4'-trifluoromethyl-biphenyl-2-carbonyl)-amino]-quinoline-6-carboxylic acid (2-butoxy-1-phenyl-ethyl)-amide | 2.58 | 612 | 611 |
| 72 | (S)-2-[(4'-trifluoromethyl-biphenyl-2-carbonyl)-amino]-quinoline-6-carboxylic acid (2-benzyloxy-1-phenyl-ethyl)-amide | 2.35 | 646 | 645 |
| 73 | (S)-2-[(4'-trifluoromethyl-biphenyl-2-carbonyl)-amino]-quinoline-6-carboxylic acid [1-phenyl-2-(4-trifluoromethyl-benzyloxy)-ethyl]-amide | 2.41 | 714 | 715 |
| 74 | (S)-2-[(4'-trifluoromethyl-biphenyl-2-carbonyl)-amino]-quinoline-6-carboxylic acid [2-(2-chloro-benzyloxy)-1-phenyl-ethyl]-amide | 2.41 | 680 | 679 |
| 75 | (S)-2-[(4'-trifluoromethyl-biphenyl-2-carbonyl)-amino]-quinoline-6-carboxylic acid [2-(2-methyl-benzyloxy)-1-phenyl-ethyl]-amide | 2.38 | 660 | 659 |

TABLE 4-continued

| Ex. No. | Compound Name | HPLC Retention time | ESMS (m + 1) | Calc. Mol. Wgt. |
|---|---|---|---|---|
| 76 | (S)-2-[(4'-trifluoromethyl-biphenyl-2-carbonyl)-amino]-quinoline-6-carboxylic acid [2-(3-chloro-benzyloxy)-1-phenyl-ethyl]-amide | 3.45 | 680 | 681 |
| 77 | (S)-2-[(4'-trifluoromethyl-biphenyl-2-carbonyl)-amino]-quinoline-6-carboxylic acid [2-(3-methyl-benzyloxy)-1-phenyl-ethyl]-amide | 2.40 | 660 | 659 |
| 78 | 2-[(4'-trifluoromethyl-biphenyl-2-carbonyl)-amino]-quinoline-6-carboxylic acid [1-phenyl-2-(3-trifluoromethyl-phenoxy)-ethyl]-amide | 2.46 | 700 | 699 |

Example 79

Preparation of (S)-2-[(4'-Trifluoromethyl-biphenyl-2-carbonyl)-amino]-quinoline-6-carboxylic acid (1-phenyl-2-propionylamino-ethyl)-amide (a) Preparation of Intermediate (S)-Methanesulfonic acid 2-tert-butoxycarbonylamino-2-phenyl-ethyl ester

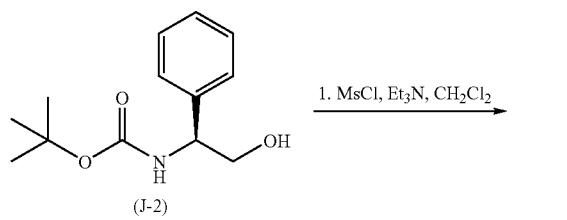

(J-2)

Intermediate (J-2a) was prepared in accordance with the procedure described in Giuseppe A. M. Giardina et al., *J. Med. Chem.* 1999, 42, 1053-1065.

(b) Preparation of Intermediate (S)-2-Azido-1-phenyl-ethylamine hydrochloride

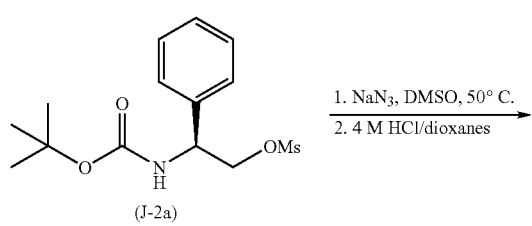

(J-2a)

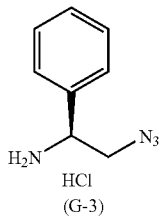

(G-3)

(S)-Methanesulfonic acid 2-tert-butoxycarbonylamino-2-phenyl-ethyl ester, (J-2a, 1.1 g, 3.48 mM) was dissolved in DMSO (25 mL) and treated with sodium azide (0.45 g, 7.0 mM). The mixture was heated to 50° C. for 24 h. After cooling to room temperature, the mixture was poured into cold water (75 mL). The solid was collected by filtration and dried under high vacuum for 24 h. The solid was stirred in 4 N HCL/dioxane for 30 min and then concentrated. The solid was used without further purification.

(c) Preparation of Intermediate (S)-2-[(4'-Trifluoromethyl-biphenyl-2-carbonyl)-amino]-quinoline-6-carboxylic acid (2-azido-1-phenyl-ethyl) amide

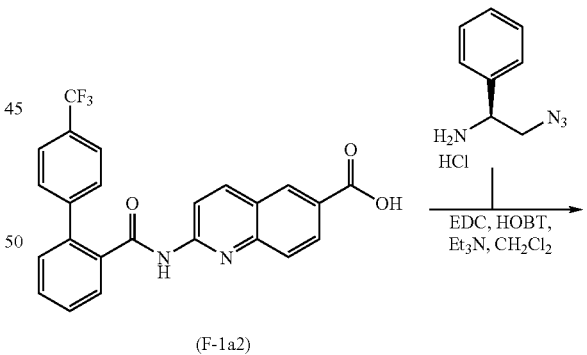

2-[(4'-Trifluoromethyl-biphenyl-2-carbonyl)-amino]-quinoline-6-carboxylic acid, (F-1a2, 0.78 g, 1.79 mM), (S)-2-azido-1-phenyl-ethylamine hydrochloride (0.36 g, 1.79 mM), EDC (0.41 g, 2.15 mM) and HOBT (10 mg, 0.075 mM), were dissolved in CH$_2$Cl$_2$ (15 mL) and treated with triethylamine (0.75 mL, 5.4 mM). The mixture was stirred at room temperature for 16 h, then was diluted with EtOAc (75 mL) and washed with 0.5 N HCl (20 mL), aqueous NaHCO$_3$ (20 mL), and brine. The EtOAc fraction was dried (MgSO$_4$), filtered and concentrated. ESMS (m+1), 581; calc. Mw, 580.

(d) Preparation of Intermediate (S)-2-[(4'-Trifluoromethyl-biphenyl-2-carbonyl)-amino]-quinoline-6-carboxylic acid (2-amino-1-phenyl-ethyl)-amide

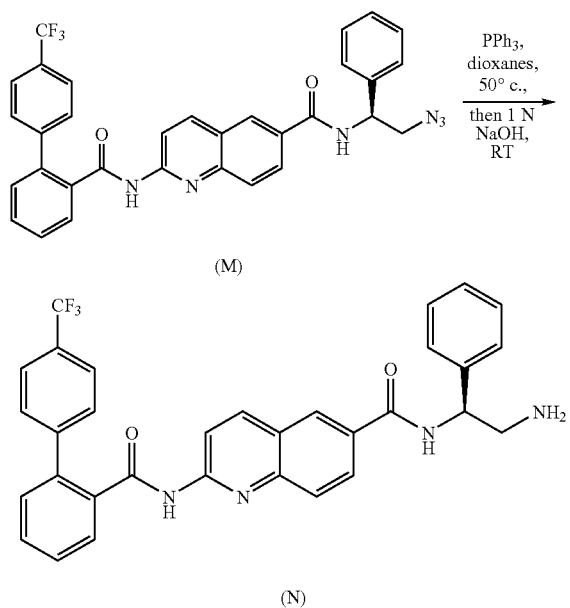

(S)-2-[(4'-Trifluoromethyl-biphenyl-2-carbonyl)-amino]-quinoline-6-carboxylic acid (2-azido-1-phenyl-ethyl) amide (M, 0.722 mg, 1.22 mM) was dissolved in dioxane (10 mL). Triphenyl phosphine (0.35 g, 1.34 mM) was added and the mixture was stirred at 50° C. for 4 h. The mixture was removed from the heat and treated with an aqueous solution of NaOH (1N, 5 mL). The resulting mixture was stirred at room temperature for 2 h. The mixture was treated with 1N HCl (10 mL) and stirred for 12 h. The precipitate was collected by filtration and washed with ether. The solid was dried under high vacuum to provide (S)-2-[(4'-trfluoromethyl-biphenyl-2-carbonyl)-amino]-quinoline-6-carboxylic acid (2-amino-1-phenyl-ethyl)-amide. ESMS (m+1), 555; calc. Mw, 554

(e) Preparation of (S)-2-[(4'-Trifluoromethyl-biphenyl-2-carbonyl)-amino]-quinoline-6-carboxylic acid (1-phenyl-2-propionylamino-ethyl)-amide

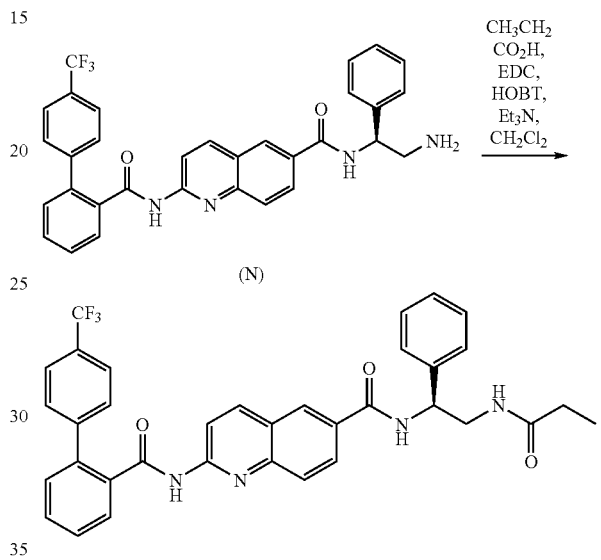

(S)-2-[(4'-Trifluoromethyl-biphenyl-2-carbonyl)-amino]-quinoline-6-carboxylic acid (2-amino-1-phenyl-ethyl)-amide (N, 30 mg, 0.05 mM), proprionic acid (0.075 mM), EDC (14 mg, 0.075 mM), HOBT (11 mg, 0.075 mM), and triethylamine (0.03 mL, 0.21 mM) were taken up in CH$_2$Cl$_2$ (1 mL) and stirred at room temperature for 16 h. The mixture was concentrated and the residue was purified by flash chromatography (silica gel) eluting with EtOAc/hexanes. HPLC retention time, 2.87 min; ESMS (m+1), 611; calc. Mw, 610

The compounds in Table 5 were prepared from appropriate starting materials using procedures analogous to those for the synthesis of the compound of Example 79.

TABLE 5

| Ex. No. | Compound Name | HPLC Retention time | ESMS (m + 1) | Calc. Mol. Wgt. |
|---|---|---|---|---|
| 80 | (S)-2-[(4'-trifluoromethyl-biphenyl-2-carbonyl)-amino]-quinoline-6-carboxylic acid (2-acetylamino-1-phenyl-ethyl)-amide | 2.70 | 597 | 596 |
| 81 | (S)-2-[(4'-trifluoromethyl-biphenyl-2-carbonyl)-amino]-quinoline-6-carboxylic acid (1-phenyl-2-propionylamino-ethyl)-amide | 2.87 | 611 | 610 |
| 82 | (S)-2-[(4'-trifluoromethyl-biphenyl-2-carbonyl)-amino]-quinoline-6-carboxylic acid (2-butyrylamino-1-phenyl-ethyl)-amide | 2.92 | 626 | 624 |
| 83 | (S)-2-[(4'-trifluoromethyl-biphenyl-2-carbonyl)-amino]-quinoline-6-carboxylic acid (2-pentanoylamino-1-phenyl-ethyl)-amide | 3.03 | 639 | 638 |

TABLE 5-continued

| Ex. No. | Compound Name | HPLC Retention time | ESMS (m + 1) | Calc. Mol. Wgt. |
|---|---|---|---|---|
| 84 | (S)-2-[(4'-trifluoromethyl-biphenyl-2-carbonyl)-amino]-quinoline-6-carboxylic acid (2-benzoylamino-1-phenyl-ethyl)-amide | 3.10 | 659 | 3.1 |
| 85 | (S)-2-[(4'-trifluoromethyl-biphenyl-2-carbonyl)-amino]-quinoline-6-carboxylic acid (2-methanesulfonylamino-1-phenyl-ethyl)-amide | 2.91 | 634 | 633 |
| 86 | (S)-2-[(4'-trifluoromethyl-biphenyl-2-carbonyl)-amino]-quinoline-6-carboxylic acid [1-phenyl-2-(toluene-4-sulfonylamino)-ethyl]-amide | 3.17 | 710 | 709 |
| 87 | (S)-2-[(4'-trifluoromethyl-biphenyl-2-carbonyl)-amino]-quinoline-6-carboxylic acid [1-phenyl-2-(propane-1-sulfonylamino)-ethyl]-amide | 3.08 | 662 | 661 |
| 88 | (S)-2-[(4'-trifluoromethyl-biphenyl-2-carbonyl)-amino]-quinoline-6-carboxylic acid (2-benzenesulfonylamino-1-phenyl-ethyl)-amide | 3.17 | 696 | 695 |
| 89 | (S)-2-[(4'-trifluoromethyl-biphenyl-2-carbonyl)-amino]-quinoline-6-carboxylic acid [2-(butane-1-sulfonylamino)-1-phenyl-ethyl]-amide | 3.17 | 676 | 675 |
| 90 | (S)-2-[(4'-trifluoromethyl-biphenyl-2-carbonyl)-amino]-quinoline-6-carboxylic acid (2-ethanesulfonylamino-1-phenyl-ethyl)-amide | 2.99 | 648 | 647 |

Example 91

Preparation of (S)-2-[(4'-Trifluoromethyl-biphenyl-2-carbonyl)amino]-quinoline-6-carboxylic acid (2-benzylamino-1-phenyl-ethyl)-amide

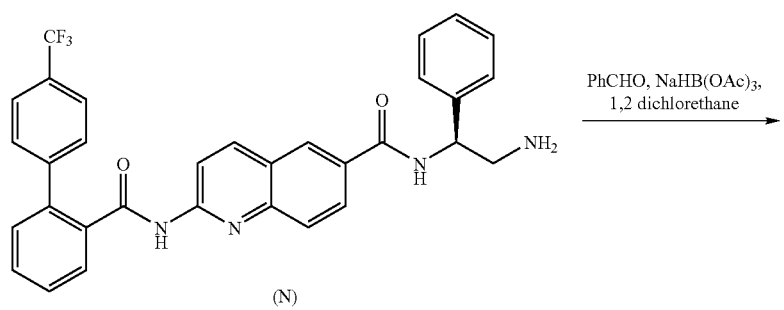

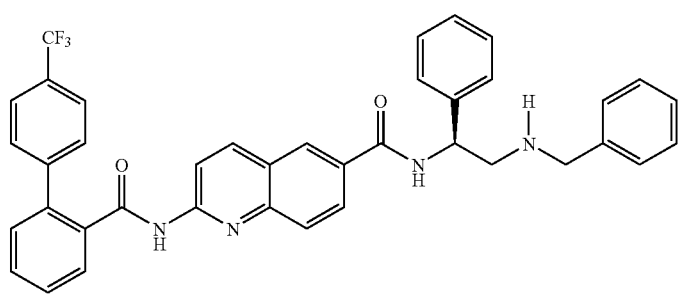

(S)-2-[(4'-Trifluoromethyl-biphenyl-2-carbonyl)-amino]-quinoline-6-carboxylic acid (2-amino-1-phenyl-ethyl)-amide (N, 30 mg, 0.05 mM) was dissolved in 1,2-dichloroethane. Benzaldehyde (0.15 mM) was added followed by sodium triacetoxy borohydride (110 mg, 0.51 mM). The mixture was stirred at room temperature for 16 h. The solution was concentrated, and the residue was purified by flash chromatography (silica gel) eluting with EtOAc/hexanes. HPLC retention time, 2.75 min; ESMS, 645; calc. Mw, 644

The compounds in Table 6 were prepared from appropriate starting materials using procedures analogous to those for the synthesis of the compound of Example 91.

TABLE 6

| Ex. No. | Compound Name | HPLC Retention time | ESMS (m + 1) | Calc. Mol. Wgt. |
|---|---|---|---|---|
| 92 | (S)-2-[(4'-trifluoromethyl-biphenyl-2-carbonyl)-amino]-quinoline-6-carboxylic acid (2-dipropylamino-1-phenyl-ethyl)-amide | 2.77 | 639 | 638 |
| 93 | (S)-2-[(4'-trifluoromethyl-biphenyl-2-carbonyl)-amino]-quinoline-6-carboxylic acid (2-dibutylamino-1-phenyl-ethyl)-amide | 2.96 | 667 | 666 |

Example 94

Preparation of (S)-2-[(4'-Trifluoromethyl-biphenyl-2-carbonyl)-amino]-quinoline-6-carboxylic acid [2-(benzyl-methyl-amino)-1-phenyl-ethyl]-amide (a). Preparation of Intermediate (S)-N²-Benzyl-N²-methyl-1-phenyl-ethane-1,2-diamine.

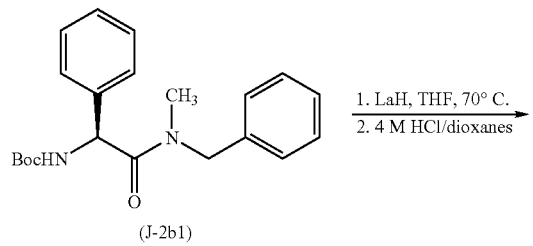

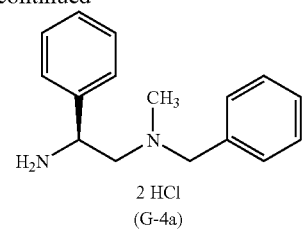

(S)-[(Benzyl-methyl-carbamoyl)-phenyl-methyl]-carbamic acid tert-butyl ester (J-2b1) may be prepared as described in Example 44(e) of PCT patent application publication No. WO 03/002533.

To a solution of (S)-[(benzyl-methyl-carbamoyl)-phenyl-methyl]-carbamic acid tert-butyl ester (J-2b1, 1.0 mM) in THF was added LAH (0.15 g, 4 mM) in portions. The mixture was stirred at room temperature for 2 h. The mixture was slowly poured into an aqueous solution of NaOH (0.5 N, 50 mL). The resulting mixture was extracted 3 times with ethyl acetate (25 mL). The combined ethyl acetate fractions were washed with brine, dried (MgSO₄), filtered and concentrated. The product was treated with 4M HCl in dioxane (4 mL). After stirring for 30 minutes at room temperature the mixture was concentrated and the residue was dried under high vacuum for 16 h. The resulting solid was used without further purification.

(b) Preparation of (S)-2-[(4'-Trifluoromethyl-biphenyl-2-carbonyl-amino]-quinoline-6-carboxylic acid [2-(benzyl-methyl-amino]-1-phenyl-ethyl]-amide

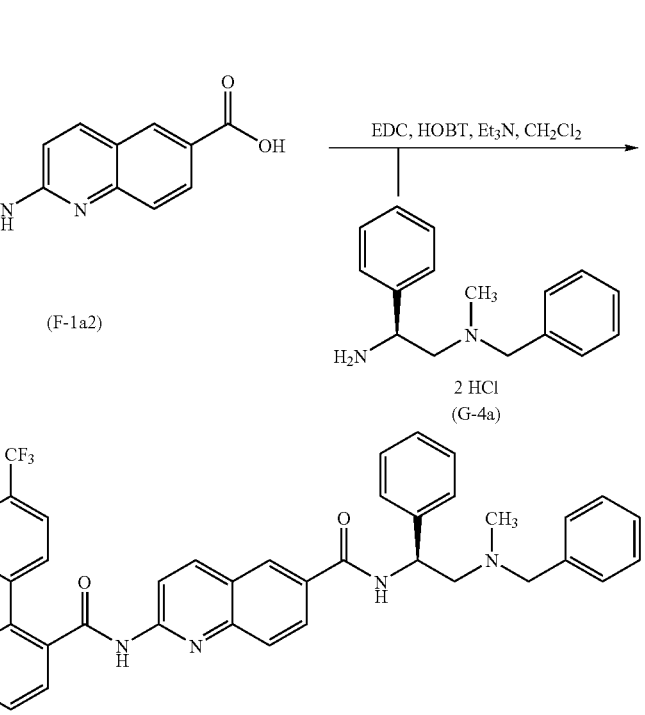

The title compound was prepared in a manner analogous to that described in Example 1(b). HPLC retention time, 2.65 min; ESMS (m+1), 660; calc. Mw, 659

The compounds in Table 7 were prepared from appropriate starting materials using procedures analogous to those described in Example (1b).

TABLE 7

| Ex. No. | Compound Name | HPLC Retention time | ESMS (m + 1) | Calc. Mol. Wgt. |
|---|---|---|---|---|
| 95 | (s)-2-[(4'-Trifluoromethyl-biphenyl-2-carbonyl)-amino]-quinoline-6-carboxylic acid [2-(ethyl-propyl-amino)-1-phenyl-ethyl]-amide | 2.56 | 625 | 624 |
| 96 | (s)-2-[(4'-Trifluoromethyl-biphenyl-2-carbonyl)-amino]-quinoline-6-carboxylic acid [2-(butyl-ethyl-amino)-1-phenyl-ethyl]-amide | 2.52 | 639 | 638 |
| 97 | (s)-2-[(4'-Trifluoromethyl-biphenyl-2-carbonyl)-amino]-quinoline-6-carboxylic acid [2-(methyl-pentyl-amino)-1-phenyl-ethyl]-amide | 2.71 | 639 | 638 |

Example 98

Preparation of (R)-2-[(4'-Trifluoromethyl-biphenyl-2-carbonyl)-amino]-quinoline-6-carboxylic acid (1-p-tolyl-ethyl)-amide

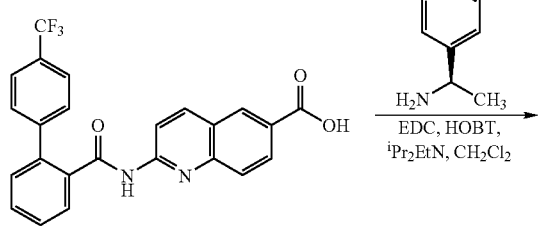

-continued

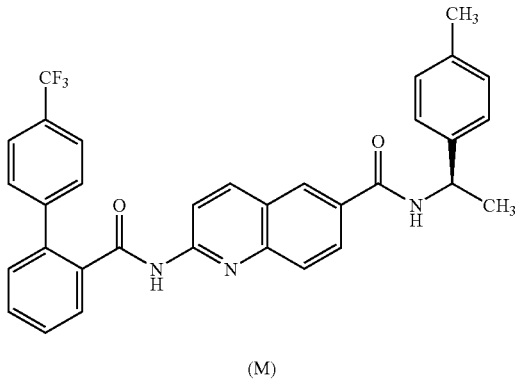

(M)

This compound was prepared in a manner analogous to that described in Example (1b). HPLC retention time, 3.23 min; ESMS (m+1), 554; calc Mw, 553

The compounds in Tables 8(a) and 8(b) were prepared from appropriate srarting materials using procedures analogous to those described in Example (1b)

TABLE 8(a)

| Ex. No. | Compound Name | HPLC Retention time | ESMS (m + 1) | Calc. Mol. Wgt. |
|---|---|---|---|---|
| 99 | (R)-2-[(4'-trifluoromethyl-biphenyl-2-carbonyl)-amino]-quinoline-6-carboxylic acid [1-(4-methoxy-phenyl)-ethyl]-amide | 3.10 | 570 | 569 |
| 100 | (R)-2-[(4'-trifluoromethyl-biphenyl-2-carbonyl)-amino]-quinoline-6-carboxylic acid [1-(3-methoxy-phenyl)-ethyl]-amide | 3.09 | 570 | 569 |
| 101 | (R)-2-[(4'-trifluoromethyl-biphenyl-2-carbonyl)-amino]-quinoline-6-carboxylic acid (1-phenyl-propyl)-amide | 2.78 | 554 | 553 |
| 102 | 2-[(4'-trifluoromethyl-biphenyl-2-carbonyl)-amino]-quinoline-6-carboxylic acid [1-(4-trifluoromethyl-phenyl)-propyl]-amide | 2.40 | 622 | 621 |
| 103 | 2-[(4'-trifluoromethyl-biphenyl-2-carbonyl)-amino]-quinoline-6-carboxylic acid [1-(3-trifluoromethyl-phenyl)-propyl]-amide | 2.33 | 622 | 621 |

TABLE 8(a)-continued

| Ex. No. | Compound Name | HPLC Retention time | ESMS (m + 1) | Calc. Mol. Wgt. |
|---|---|---|---|---|
| 104 | 2-[(4'-trifluoromethyl-biphenyl-2-carbonyl)-amino]-quinoline-6-carboxylic acid [1-(4-chloro-phenyl)-pentyl]-amide | 3.47 | 616 | 615 |
| 105 | 2-[(4'-trifluoromethyl-biphenyl-2-carbonyl)-amino]-quinoline-6-carboxylic acid (1-phenyl-hexyl)-amide | 3.23 | 596 | 595 |
| 106 | 2-[(4'-trifluoromethyl-biphenyl-2-carbonyl)-amino]-quinoline-6-carboxylic acid (1-phenyl-decyl)-amide | 3.53 | 652 | 651 |
| 107 | 2-[(4'-Isopropyl-biphenyl-2-carbonyl)-amino]-quinoline-6-carboxylic acid (1-phenyl-propyl)-amide | | | 527 |

TABLE 8(b)

| Ex. No. | Compound Name | ESMS (m + 1) | $^1$H NMR |
|---|---|---|---|
| 108 | (S)-2-[(4'-trifluoromethyl-biphenyl-2-carbonyl)-amino]-quinoline-6-carboxylic acid (phenyl-pyridin-2-yl-methyl)-amide | 603 | $^1$H NMR(400MHz, CD$_3$Cl): ☐6.35(d, 1H), 7.05-7.65(c, 15H), 7.97(m, 1H), 8.02(d, 1H), 8.18(d, 1H), 8.29(d, 1H), 8.42(c, 1H), 8.58(d, 1H), 8.69(d, 1H). |
| 109 | 2-[(4'-trifluoromethyl-biphenyl-2-carbonyl)-amino]-quinoline-6-carboxylic acid (1-pyridin-2-yl-propyl)-amide | 556 | 1H NMR(400MHz, CD$_3$Cl): ☐0.88(t, 3H), 2.00(m, 2H), 5.25(m, 1H), 7.2-7.7(c, 10H), 7.80(d, 1H), 8.02(m, 2H), 8.22(d, 1H), 8.28(d, 1H), 8.43(c, 1H), 8.58(d, 1H), 8.71(s, 1H). |
| 110 | 2-[(4'-trifluoromethyl-biphenyl-2-carbonyl)-amino]-quinoline-6-carboxylic acid (1-pyridin-2-yl-ethyl)-amide | 541 | 1H NMR(400MHz, CD$_3$Cl): ☐1.58(d, 3H), 5.38(c, 1H), 7.2-7.7(c, 10H), 7.94(d, 2H), 8.02(m, 1H), 8.21(d, 1H), 8.28(d, 1H), 8.4(c, 1H), 8.56(d, 1H), 8.72(c, 1H). |
| 111 | (S)-2-[(4'-isopropyl-biphenyl-2-carbonyl)-amino]-quinoline-6-carboxylic acid (phenyl-pyridin-2-yl-methyl)-amide | 578 | 1H NMR(400MHz, CD$_3$Cl): ☐1.16(d, 6H), 2.84(m, 1H), 6.36(d, 1H), 7.2-7.47(c, 11H), 7.53(m, 1H), 7.66(m, 2H), 7.79(m, 1H), 8.06(m, 1H), 8.15(s, 1H), 8.22(d, 1H), 8.31(d, 1H), 8.48(d, 1H), 8.63(d, 2H). |
| 112 | (S)-2-[(4'-tert-butyl-biphenyl-2-carbonyl)-amino]-quinoline-6-carboxylic acid (phenyl-pyridin-2-yl-methyl)-amide | 592 | 1H NMR(400MHz, CD$_3$Cl): d 1.23(s, 9H), 2.84(m, 1H), 6.36(d, 1H), 7.2-7.47(c, 11H), 7.53(m, 1H), 7.66(m, 2H), 7.79(m, 1H), 8.06(m, 1H), 8.15(s, 1H), 8.22(d, 1H), 8.31(d, 1H), 8.48(d, 1H), 8.63(d, 2H) |

Example 113

Preparation of (S)-Phenyl-({2-[(4'-trifluoromethyl-biphenyl-2-carbonyl)-amino]-quinoline-6-carbonyl}-amino)-acetic acid methyl ester

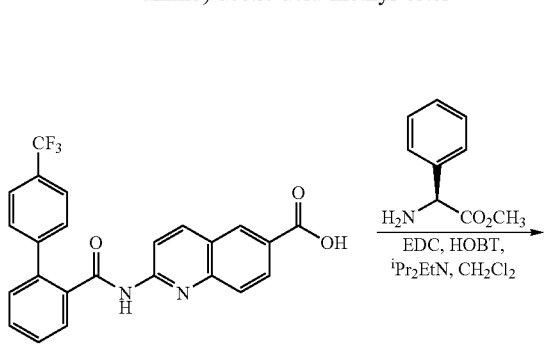

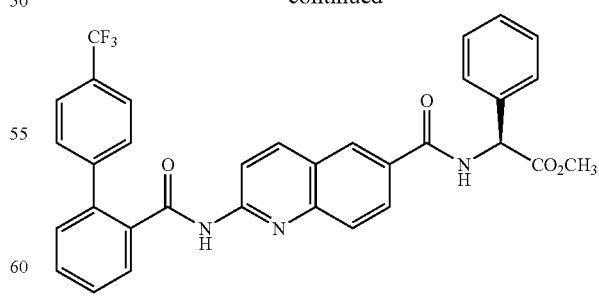

This compound was prepared in a manner analogous to that described in Example (1b). The intermediate phenylglycine methyl ester is commercially available. HPLC retention time, 2.86 min; ESMS (m+1), 584; calc. Mw, 583

Example 114

(S)-2-[(4'-tert-Butylphenyl-2-carbonyl)amino]quinoline-6-carboxylic acid {[(4-fluorobenzyl)methylcarbamoyl]phenylmethyl}amide a) Preparation of Intermediate N-(4-Fluorobenzyl)formamide

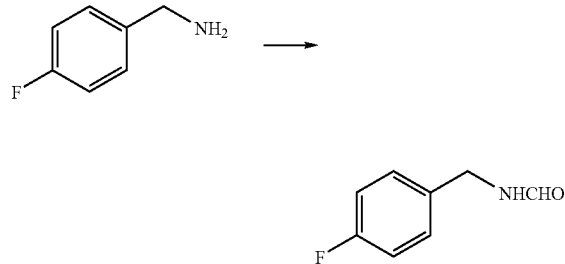

A solution of 4-fluorobenzylamine (20 g, 160 mmol) in ethyl formate was heated at reflux for 4 h. After cooling, the solvent was evaporated to afford a yellow solid. Trituration with cold EtOAc afforded the title compound as a white solid (17.46 g, 71%). $^1$H NMR (CDCl$_3$): □8.24 (s, 1H), 7.25 (m, 2H), 7.00 (m, 2H), 5.91 (br s, 1H), 4.42 (d, 2H).

b) Preparation of Intermediate (4-Fluorobenzyl)methylamine

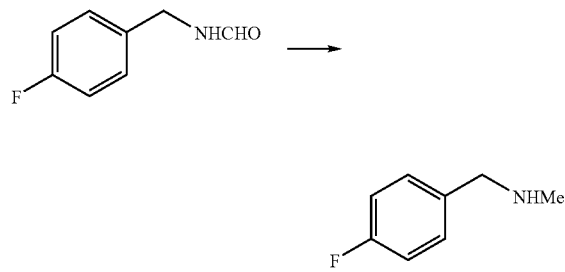

A solution of N-(4-fluorobenzyl)formamide (17.46 g, 114 mol) in THF (100 mL) was cooled in an ice bath (0° C.). Lithium alumininum hydride (7.2 g, 190 mmol) was then added carefully in portions with stirring. The cooling bath was removed and the reaction mixture was stirred at room temperature for about 64 h. The reaction was diluted with diethyl ether and again cooled in an ice bath. It was then quenched by careful dropwise addition of aq. 1N NaOH solution followed by saturated aq. Na$_2$SO$_4$ solution. The resulting mixture was filtered, washing the collected solids with diethyl ether. The filtrate was concentrated to afford the title compound as a clear oil (15.2 g, 96%). $^1$H NMR (CDCl$_3$): □7.28 (m, 2H). 7.02 (t, 2H), 3.73 (s, 2H), 2.46 (s, 3H).

c) Preparation Intermediate of (S)-{[(4-Fluorobenzyl)methylcarbamoyl]phenylmethyl}carbamic acid tert-butyl ester

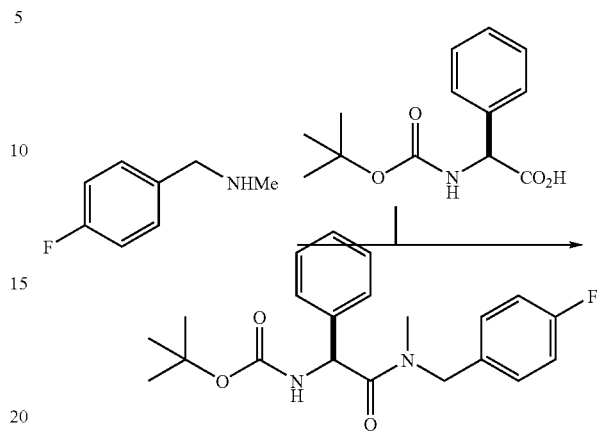

A solution of N-Boc-L-phenylglycine (H, 17.2 g, 68.5 mmol) and (4-fluorobenzyl)methylamine (10.47 g, 75.3 mmol) in CH$_2$Cl$_2$ (550 mL) was cooled to 0° C. Disopropylethylamine (35.8 mL, 205 mmol) and PyBroP (38.3 g, 82.1 mmol) were then added sequentially. The cooling bath was removed and the reaction mixture was stirred at room temperature overnight. The solvent was evaporated and the title compound (24.5 g, 96%) was isolated by chromatography on silica gel eluting with a gradient of 40% to 60% ethyl acetate in hexane. $^1$H NMR (selected signals, CDCl$_3$): □6.02 (d, 0.3H), 5.56 (d, 0.7H), 2.83 (s, 0.9H), 2.78 (s, 2.1H), 1.40 (s, 6.3 H, 1.39 (s, 2.7H).

d) Preparation of Intermediate (S)-2-Amino-N-(4-fluorobenzyl)-N-methyl-2-phenylacetamide hydrochloride

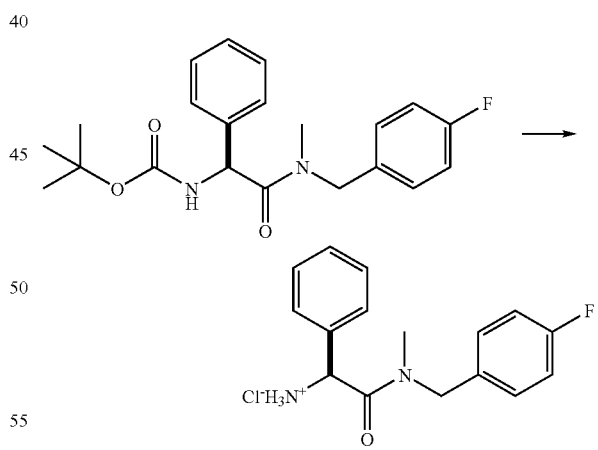

A solution of HCl in dioxane (4M, 100 mL) was cooled in an ice bath and added to (S)-{[(4-fluorobenzyl)methylcarbamoyl]phenylmethyl}carbamic acid tert-butyl ester (9.49 g, 25.5 mmol). The reaction mixture was then stirred for 5 h, allowing the temperature to rise to room temperature over this period. Volatiles, including HCl and solvent, were evaporated to afford the title compound as a white solid (7.9 g, 100%). $^1$H NMR (selected signals, CDCl$_3$): □8.94 (br s, 3H), 5.94 (br s, 0.3H), 5.82 (br s, 0.7H), 2.66 (s, 0.9H), 2.64 (s, 2.1H).

a) Preparation of (S)-2-[(4'-tert-Butylbiphenyl-2-carbonyl)amino]quinoline-6-carboxylic acid {[(4-fluorobenzyl)methylcarbamoyl]phenylmethyl}amide

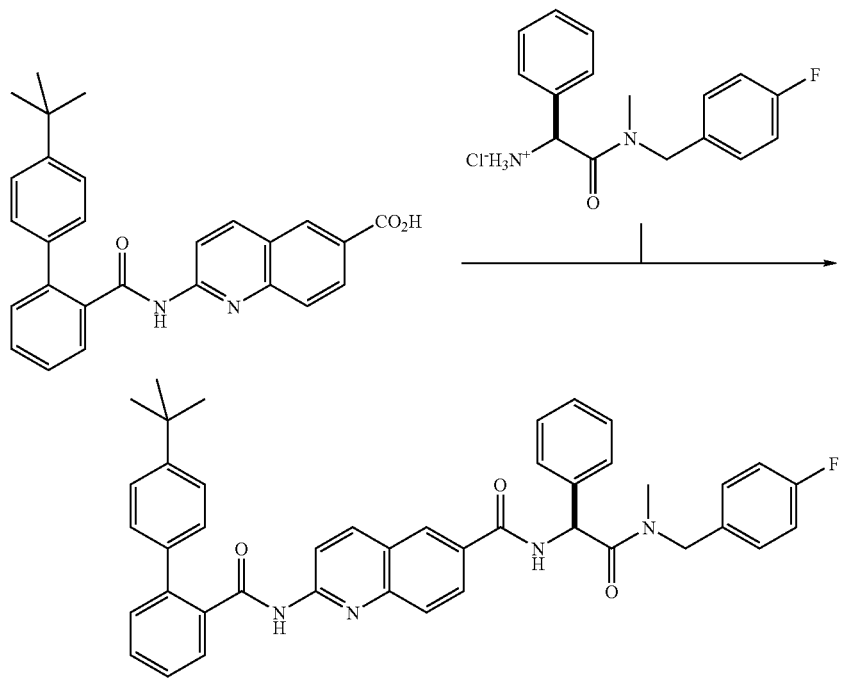

To a solution of 2-[(4'-tert-butylbiphenyl-2-carbonyl)amino]-quinoline-6-carboxylic acid (11.0 g, 26 mmol) and (S)-2-amino-N-(4-fluorobenzyl)-N-methyl-2-phenylacetamide hydrochloride (12.04 g, 39 mmol) in $CH_2Cl_2$ (50 mL) at room temperature was added triethylamine (5.4 mL, 39 mmol) and N,N-dimethylaminopropylethylcarbodiimide hydrochloride (7.48 g, 39 mmol). The reaction mixture was stirred at room temperature overnight. Volatiles, including solvent, were evaporated under vacuum. The title compound, a white amorphous solid (14.4 g. 82%), was isolated by chromatography on silica gel eluting with a gradient of 40% to 60% ethyl acetate in hexane. $^1$H NMR (selected signals, $CDCl_3$): □6.15 (d, 0.3H), 6.09 (d, 0.7H), 2.91 (s, 0.9H), 2.86 (s, 2.1H), 1.23 (s, 9H). MS m/z 679 (M+1).

The compounds in Table 9(a) were prepared using procedures analogous to those described above for the synthesis of the compound of Example 114 using appropriately substituted starting materials/intermediates which are available commercially, prepared in a manner analogous to the methods described above for other intermediates, or prepared using procedures known to those of average skill in the art.

TABLE 9(a)

| Ex. No. | Compound Name | Select $^1$H NMR signals ($CDCl_3$) | ESMS (m + 1) |
|---|---|---|---|
| 115 | (R)-2-[(4'-Benzyloxybiphenyl-2-carbonyl)amino]quinoline-6-carboxylic acid (1-phenyl-ethyl)amide | 5.01(s, 2H); 5.4(m, 1H); 1.65(d, 3H) | 578 |
| 116 | (S)-2-[(4'-Benzyloxybiphenyl-2-carbonyl)amino]quinoline-6-carboxylic acid (phenyl-pyridin-2-ylmethyl)amide | 5.0(s, 2H) | 641 |
| 117 | (S)-2-[(4'-Benzyloxybiphenyl-2-carbonyl)amino]quinoline-6-carboxylic acid (isopropyl-carbamoylphenylmethyl)amide | 5.01(s, 2H), 4.13(m, 1H); 1.18(d, 3H), 1.07(d, 3H) | 649 |
| 118 | (S)-3-[2-({2-[(4'-Benzyloxybiphenyl-2-carbonyl)amino]quinoline-6-carbonyl}amino)-2-phenyl-acetylamino]propionic acid benzyl ester | 5.06(s, 2H), 5.00(m, 2H); 3.55(m, 1H); 3.50(m, 1H); 2.57(m, 2H) | 769 |
| 119 | (R)-2-[(4'-Isopropylbiphenyl-2-carbonyl)amino]quinoline-6-carboxylic acid (1-phenyl-ethyl)amide | 2.84(m, 1H); 1.62(d, 3H); 1.14(d, 6H) | 514 |
| 120 | (S)-2-[(4'-Isopropylbiphenyl-2-carbonyl)amino]quinoline-6-carboxylic acid (phenyl-pyridin-2-yl-methyl)amide | 2.84(m, 1H); 1.16(d, 6H) | 577 |

TABLE 9(a)-continued

| Ex. No. | Compound Name | Select ¹H NMR signals (CDCl₃) | ESMS (m + 1) |
|---|---|---|---|
| 121 | (S)-2-[(4'-Isopropylbiphenyl-2-carbonyl)amino]quinoline-6-carboxylic acid (carbamoylphenylmethyl)amide | | 543 |
| 122 | (S)-2-[(4'-Isopropylbiphenyl-2-carbonyl)amino]quinoline-6-carboxylic acid (isopropyl-carbamoylphenylmethyl)amide | 5.03(s, 2H); 2.83(m, 1H); 1.13(d, 6H) | 705 |
| 123 | (S)-2-[(4'-Isopropylbiphenyl-2-carbonyl)amino]quinoline-6-carboxylic acid (tert-butyl-carbamoylphenylmethyl)amide | 5.51(d, 1H); 2.84(m, 1H); 1.31(s, 9H); 1.15(d, 6H) | 599 |
| 124 | (S)-2-[(4'-Isopropylbiphenyl-2-carbonyl)amino]quinoline-6-carboxylic acid [(benzylmethylcarbamoyl)phenylmethyl]amide | 6.13(d, 0.3H); 6.09(d, 0.7H); 2.89(s, 0.9H); 2.85(s, 2.1H); 1.13(d, 6H) | 647 |
| 125 | (S)-2-[(4'-Isopropylbiphenyl-2-carbonyl)amino]quinoline-6-carboxylic acid {[(4-fluoro-benzyl)methylcarbamoyl]phenylmethyl}-amide | 6.15(d, 0.3H); 6.10(d, 0.7H); 2.93(s, 0.9H); 2.88(s, 2.1H); 1.18(d, 6H) | 665 |
| 126 | PF-00929034: 3-[2-({2-[(4'-Isopropylbiphenyl-2-carbonyl)amino]quinoline-6-carbonyl}amino)-2-phenyl-acetylamino]propionic acid benzyl ester | 5.55(d, 1H); 5.04(s, 2H); 1.13(d, 6H) | 705 |
| 127 | (S)-2-[(4'-Methylbiphenyl-2-carbonyl)-amino]quinoline-6-carboxylic acid (phenylpyridin-2-ylmethyl)amide | 6.36(d, 1H); 2.31(s, 3H) | 549 |
| 128 | (S)-2-[(4'-Methylbiphenyl-2-carbonyl)-amino]quinoline-6-carboxylic acid {[(4-fluorobenzyl)-methylcarbamoyl]phenylmethyl}amide | 6.13(d, 0.3H); 6.08(d, 0.7H); 2.90(s, 0.9H); 2.86(s, 2.1H); 2.30(s, 3H) | 637 |
| 129 | (S)-2-[(4'-Methylbiphenyl-2-carbonyl)-amino]quinoline-6-carboxylic acid [(4-fluorobenzyl-carbamoyl)phenylmethyl]amide | 6.00(d, 1H); 4.24(m, 2H); 2.24(s, 3H) | 623 |
| 130 | (S)-2-[(4'-Methylbiphenyl-2-carbonyl)-amino]quinoline-6-carboxylic acid [(methylpyridin-2-yl-methylcarbamoyl)phenylmethyl]amide | 6.12(d, 1H); 2.24(s, 3H); 2.98(s, 2.1H); 2.94(s, 0.9H) | 620 |
| 131 | (S)-2-[(4'-Isopropylbiphenyl-2-carbonyl)amino]quinoline-6-carboxylic acid [(4-fluorobenzylcarbamoyl)phenylmethyl]amide | 5.65(d, 1H); 4.42(s, H); 2.85(m, 1H); 1.15(d, 6H) | 651 |
| 132 | (S)-2-[(4'-Isopropylbiphenyl-2-carbonyl)amino]quinoline-6-carboxylic acid [(methyl-pyridin-2-ylmethylcarbamoyl)phenylmethyl]amide | 6.12(m, 1H); 3.00(s, 3H); 2.83(m, 1H); 1.14(d, 6H) | 648 |
| 133 | (S)-2-[(4'-Isopropylbiphenyl-2-carbonyl)amino]quinoline-6-carboxylic acid {phenyl-[(pyridin-2-ylmethyl)carbamoyl]methyl}amide | 5.96(d, 1H); 4.32(m, 2H); 2.72(m, 1H); 1.03(m, 6H) | 634 |
| 134 | (S)-2-[(4'-tert-Butylbiphenyl-2-carbonyl)amino]quinoline-6-carboxylic acid{[(4-fluoro-benzyl)methylcarbamoyl]phenylmethyl}amide | 6.15(d, 0.3H); 6.09(d, 0.7H); 2.91(s, 0.9H); 2.86(s, 2.1H); 1.23(s, 9H) | 679 |
| 135 | (S)-2-[(4'-tert-Butylbiphenyl-2-carbonyl)amino]quinoline-6-carboxylicacid[(4-fluoro-banzylcarbamoyl)phenylmethyl]amide | 5.65(d, 1H); 4.43(m, 2H); 1.23(s, 9H) | 665 |
| 136 | (S)-2-[(4'-tert-Butylbiphenyl-2-carbonyl)amino]quinoline-6-carboxylic acid[(methylpyridin-2-ylmethylcarbamoyl)phenylmethyl]-amide | 6.11(m, 1H); 3.01(0.9H); 2.99(2.1H); 1.21(s, 9H) | 662 |
| 137 | (S)-2-[(4'-tert-Butylbiphenyl-2-carbonyl)amino]quinoline-6-carboxylic acid{phenyl-[(pyridin-2-ylmethyl)carbamoyl]methyl}amide | 5.93(d, 1H); 4.36(m, 2H); 1.12(s, 9H) | 648 |
| 138 | (R)-2-[(4'-tert-Butylbiphenyl-2-carbonyl)amino]quinoline-6-carboxylic acid (1-phenyl-ethyl)amide | 6.40(d, 1H); 5.38(m, 1H); 1.64(d, H); 1.23(s, 9H) | 528 |
| 139 | (S)-2-[(4'-tert-Butylbiphenyl-2-carbonyl)amino]quinoline-6-carboxylic acid (phenyl-pyridin-2-ylmethyl)amide | 6.35(d, 1H); 1.23(s, 9H) | 591 |
| 140 | (S)-2-[(4'-Ethylbiphenyl-2-carbonyl)-amino]quinoline-6-carboxylic acid {[(4-fluorobenzyl)-methylcarbamoyl]phenylmethyl}amide | 6.13(d, 0.3H); 6.08(d, 0.7H); 2.88(s, 0.9H); 2.85(s, 2.1H); 2.58(q, 2H); 1.14(t, 3H) | 651 |

TABLE 9(a)-continued

| Ex. No. | Compound Name | Select $^1$H NMR signals (CDCl$_3$) | ESMS (m + 1) |
|---|---|---|---|
| 141 | (S)-2-[(4'-Ethylbiphenyl-2-carbonyl)-amino]quinoline-6-carboxylic acid [(4-fluorobenzyl-carbamoyl)phenylmethyl]amide | 5.74(d, 1H); 4.39(d, 2H); 2.58(q, 2H); 1.14(t, 3H) | 637 |
| 142 | (S)-2-[(4'-Ethylbiphenyl-2-carbonyl)-amino]quinoline-6-carboxylic acid [(methylpyridin-2-yl-methylcarbamoyl)phenylmethyl]amide | 6.11(m, 1H); 3.03(s, 0.9H); 3.00(s, 2.1H); 2.59(q, 2H); 1.15(t, 3H) | 634 |
| 143 | (S)-2-[(4'-Ethylbiphenyl-2-carbonyl)-amino]quinoline-6-carboxylic acid {phenyl[(pyridin-2-ylmethylcarbamoyl]methyl}amide | 5.76(d, 1H); 4.63(d, 1H); 4.47(d, 1H); 2.58(q, 2H); 1.14(t, 3H) | 620 |
| 144 | (S)-2-[(4'-Ethylbiphenyl-2-carbonyl)-amino]quinoline-6-carboxylic acid (phenylpyridin-2-yl-methyl)amide | 6.35(d, 1H); 2.60(q, 2H); 1.15(t, 3H) | 563 |
| 145 | 2-[(4'-Ethylbiphenyl-2-carbonyl)-amino]quinoline-6-carboxylic acid benzhydrylamide | 6.48(d, 1H); 2.60(q, 2H); 1.15(t, 3H) | 562 |
| 146 | (S)-2-[(4'-Propylbiphenyl-2-carbonyl)-amino]quinoline-6-carboxylic acid {[(4-fluorobenzyl)-methylcarbamoyl]phenylmethyl}amide | 6.13(d, 0.3H); 6.08(d, 0.7H); 2.90(s, 0.9H); 2.85(s, 2.1H); 2.52(t, 2H); 1.52(m, 2H); 0.76(t, 3H) | 665 |
| 147 | (S)-2-[(4'-Propylbiphenyl-2-carbonyl)-amino]quinoline-6-carboxylic acid [(4-fluorobenzylcarbamoyl)phenylmethyl]amide | 5.92(d, 1H); 4.30(m, 2H); 2.50(t, 2H); 1.52(m, 2H); 0.77(t, 3H) | 651 |
| 148 | (S)-2-[(4'-Propylbiphenyl-2-carbonyl)-amino]quinoline-6-carboxylic acid [(methylpyridin-2-yl-methylcarbamoyl)phenylmethyl]amide | 6.12(m, 1H); 3.03(s, 0.9H); 3.00(s, 2.1H); 2.53(t, 2H); 1.53(m, 2H); 0.76(t, 3H) | 648 |
| 149 | (S)-2-[(4'-Propylbiphenyl-2-carbonyl)-amino]quinoline-6-carboxylic acid (phenylpyridin-2-yl-methyl)amide | 6.36(d, 1H); 2.54(t, 2H); 1.53(m, 2H); 0.78(t, 3H) | 577 |
| 150 | (S)-2-[(4'-Methoxybiphenyl-2-carbonyl)-amino]quinoline-6-carboxylic acid {[(4-fluorobenzyl)-methylcarbamoyl]phenylmethyl}amide | 6.14(d, 0.3H); 6.08(d, 0.7H); 3.74(s, 3H); 2.90(s, 0.9H); 2.86(s, 2.1H) | 653 |
| 151 | (S)-2-[(4'-Methoxybiphenyl-2-carbonyl)-amino]quinoline-6-carboxylic acid [(4-fluorobenzylcarbamoyl)phenylmethyl]amide | 5.70(d, 1H); 4.41(d, 2H); 3.74(s, 3H) | 639 |
| 152 | (S)-2-[(4'-Methoxybiphenyl-2-carbonyl)-amino]quinoline-6-carboxylic acid [(methylpyridin-2-yl-methylcarbamoyl)phenylmethyl]amide | 6.12(m, 1H); 3.75(s, 3H); 3.03(s, 0.9H); 3.00(s, 2.1H) | 636 |
| 153 | (S)-2-[(4'-Methoxybiphenyl-2-carbonyl)-amino]quinoline-6-carboxylic acid (phenylpyridin-2-yl-methyl)amide | 6.35(d, 1H); 3.75(s, 3H) | 565 |
| 154 | (S)-2-[(4'-Benzyloxybiphenyl-2-carbonyl)amino]quinoline-6-carboxylic acid [(4-fluorobenzylcarbamoyl)phenylmethyl]amide | 5.67(d, 1H); 5.00(s, 2H); 4.43(m, 2H) | 715 |
| 155 | (S)-2-[(4'-Ethoxybiphenyl-2-carbonyl)-amino]quinoline-6-carboxylic acid {[(4-fluorobenzyl)-methylcarbamoyl]phenylmethyl}amide | 6.14(d, 0.3H); 6.08(d, 0.7H); 3.83(m, 2H); 2.81(s, 2.1H); 2.72(0.9H); 1.22(t, 3H) | 667 |
| 156 | (S)-2-[(4'-Ethoxybiphenyl-2-carbonyl)-amino]quinoline-6-carboxylic acid [(4-fluorobenzylcarbamoyl)phenylmethyl]amide | 5.65(d, 1H); 4.44(m, 2H); 3.98(q, 2H); 1.34(t, 3H) | 653 |
| 157 | (S)-2-[(4'-Ethoxybiphenyl-2-carbonyl)-amino]quinoline-6-carboxylic acid [(methylpyridin-2-yl-methylcarbamoyl)phenylmethyl]amide | 612(m, 1H); 3.93(m, 2H); 2.99(s, 2.1H); 2.97(s, 0.9H); 1.29(t, 3H) | 650 |

TABLE 9(a)-continued

| Ex. No. | Compound Name | Select ¹H NMR signals (CDCl₃) | ESMS (m + 1) |
|---|---|---|---|
| 158 | (S)-2-[(4'-Ethoxybiphenyl-2-carbonyl)-amino]quinoline-6-carboxylic acid (phenylpyridin-2-yl-methyl)amide | 6.36(d, 1H); 3.94(q, 2H); 1.32(t, 3H) | 579 |
| 159 | 2-[(4'-Ethoxybiphenyl-2-carbonyl)-amino]quinoline-6-carboxylic acid benzhydrylamide | 6.49(d, 1H); 3.97(q, 2H); 1.34(t, 3H) | 578 |
| 160 | (S)-2-[(4'-Isopropoxybiphenyl-2-carbonyl)amino]quinoline-6-carboxylic acid {[(4-fluorobenzyl)methylcarbamoyl]phenylmethyl}amide | 6.14(d, 0.3); 6.08(0.7H); 4.48(m, 1H); 2.83(s, 2.1H); 2.77(s, 0.9H); 1.23(d, 6H) | 681 |
| 161 | (S)-2-[(4'-Isopropoxybiphenyl-2-carbonyl)amino]quinoline-6-carboxylic acid [(4-fluorobenzylcarbamoyl)phenylmethyl]amide | 5.84(d, 1H); 4.47(m, 1H); 4.35(m, 2H); 1.24(d, 6H) | 667 |
| 162 | (S)-2-[(4'-Isopropoxybiphenyl-2-carbonyl)amino]quinoline-6-carboxylic acid [(methyl-pyridin-2-ylmethylcarbamoyl)phenylmethyl]amide | 6.13(m, 1H); 4.40(m, 1H) | 664 |
| 163 | (S)-2-[(4'-Isopropoxybiphenyl-2-carbonyl)amino]quinoline-6-carboxylic acid {[methyl(4-trifluoromethylbenzyl)carbamoyl]phenylmethyl}amide | 6.12(m, 1H); 4.48(m, 1H); 2.94(s, 0.9H); 2.91(s, 2.1H); 1.22(d, 6H) | 731 |
| 164 | (S)-2-[(4'-Isopropoxybiphenyl-2-carbonyl)amino]quinoline-6-carboxylic acid [phenyl(4-trifluoromethylbenzylcarbamoyl)methyl]amide | 5.84(d, 1H); 1.23(d, 6H) | 717 |
| 165 | (S)-2-[(4'-Isopropoxybiphenyl-2-carbonyl)amino]quinoline-6-carboxylic acid {[(5-chloro-pyridin-2-ylmethyl)methylcarbamoyl]-phenylmethyl}-amide | 6.09(m, 1H); 4.71(m, 2H); 4.48(m, 1H); 3.01(s, 0.9H); 3.00(s, 2.1H); 1.24(m, 6H) | 699 |
| 166 | (S)-2-[(4'-Isopropoxybiphenyl-2-carbonyl)amino]quinoline-6-carboxylic acid {[(5-chloro-pyridin-2-ylmethyl)carbamoyl]phenylmethyl} amide | 5.75(d, 1H); 1.23(d, 6H) | 685 |
| 167 | (S)-2-[(4'-Isopropoxybiphenyl-2-carbonyl)amino]quinoline-6-carboxylic acid {[methyl(5-trifluoromethylpyridin-2-ylmethyl)carbamoyl]phenyl-methyl}amide | 6.13(d, 0.7H); 6.06(0.3H); 4.46(m, 1H); 3.04(s, 3H); 1.22(d, 6H) | 732 |
| 168 | (S)-2-[(4'-Isopropoxybiphenyl-2-carbonyl)amino]quinoline-6-carboxylic acid {phenyl[(5-trifluoromethylpyridin-2-ylmethyl)carbamoyl]methyl}-amide | 5.77(d, 1H); 4.72(dd, 1H); 4.60(dd, 1H); 4.48(m, 1H); 1.23(d, 6H) | 718 |
| 169 | (S)-2-[(4'-Isopropoxybiphenyl-2-carbonyl)amino]quinoline-6-carboxylic acid (phenyl-pyridin-2-ylmethyl)amide | 6.35(d, 1H); 4.45(m, 1H); 1.23(d, 6H) | 593 |
| 170 | 2-[(4'-Isopropoxybiphenyl-2-carbonyl-amino]quinoline-6-carboxylic acid benzhydrylamide | 6.50(d, 1H); 4.49(m, 1H); 1.23(d, 6H) | 592 |
| 171 | (S)-2-[(4'-tert-Butoxybiphenyl-2-carbonyl)aminoquinoline-6-carboxylic acid {[(4-fluoro-benzyl)methylcarbamoyl]phenylmethyl}amide | 6.13(d, 0.3H); 6.09(d, 0.7H); 2.90(s, 0.9H); 2.86(s, 2.1H); 1.13(s, 9H) | 695 |
| 172 | (S)-2-[(4'-tert-Butoxybiphenyl-2-carbonyl)amino]quinoline-6-carboxylic acid[(4-fluoro-benzylcarbamoyl)phenylmethyl]amide | 5.88(d, 1H); 4.36(m, 2H); 1.14(s, 9H) | 681 |
| 173 | (S)-2-[(4'-tert-Butoxybiphenyl-2-carbonyl)amino]quinoline-6-carboxylicacid[(methyl-pyridin-2-ylmethylcarbamoyl)phenylmethyl]amide | 6.11(d, 1H); 3.04(S, 0.9H); 2.99(s, 2.1H); 1.11(s, 9H) | 678 |
| 174 | (S)-2-[(4'-tert-Butoxy-biphenyl-2-carbonyl)amino]quinoline-6-carboxylic acid (phenyl-pyridin-2-yl-methyl)amide | 6.37(d, 1H); 1.14(s, 9H) | 607 |
| 175 | 2-[(4'-tert-Butoxybiphenyl-2-carbonyl)-amino]quinoline-6-carboxylic acid benzhydrylamide | 6.50(d, 1H); 1.15(s, 9H) | 606 |
| 176 | (S)-2-[(4'-Methylsulfanylbiphenyl-2-carbonyl)amino]quinoline-6-carboxylic acid{[(4-fluoro-benzyl)methylcarbamoyl]phenylmethyl}amide | 6.14(d, 0.3H); 6.09(d, 0.7H); 2.91(s, 0.9H); 2.86(s, 2.1H); 2.41(s, 3H) | 669 |
| 177 | (S)-2-[(4'-tert-Butylbiphenyl-2-carbonyl)amino]quinoline-6-carboxylic acid(methyl-carbamoylphenylmethyl)amide | 5.58(d, 1H); 2.86(s, 3H); 1.23(s, 9H) | 571 |

TABLE 9(a)-continued

| Ex. No. | Compound Name | Select $^1$H NMR signals (CDCl$_3$) | ESMS (m + 1) |
|---|---|---|---|
| 178 | (R)-2-(2-Cyclopentylbenzoylamino)-quinoline-6-carboxylic acid (1-phenylethyl)amide | 6.41(d, 1H); 5.35(m, 1H); 3.41(m, 1H); 1.61(d, 3H) | 464 |
| 179 | (S)-2-(2-Cyclopentylbenzoylamino)-quinoline-6-carboxylic acid (carbamoylphenylmethyl)-amide | (CD$_3$OD) 8.43(m, 2H); 5.71(s, 1H); 3.38(m, 1H) | 493 |
| 180 | (S)-2-(2-Cyclopentylbenzoylamino)-quinoline-6-carboxylic acid (isopropylcarbamoyl-phenylmethyl)amide | 5.65(d, 1H); 5.59(d, 1H); 4.00(m, 1H); 3.38(m, 1H); 1.07(d, 3H); 0.98(d, 3H) | 535 |
| 181 | (R)-2-(2-Cyclohexylbenzoylamino)-quinoline-6-carboxylic acid (1-phenylethyl)amide | 6.48(d, 1H); 5.40(m, 1H); 3.04(m, 1H); 1.65(d, 3H) | 478 |
| 182 | (S)-2-(2-Cyclohexylbenzoylamino)-quinoline-6-carboxylic acid (carbamoylphenylmethyl)-amide | 5.75(d, 1H); 3.01(m, 1H) | 507 |
| 183 | (S)-2-(2-Cyclohexylbenzoylamino)-quinoline-6-carboxylic acid (isopropylcarbamoyl-phenylmethyl)amide | 5.61(d, 1H); 4.15(m, 1H); 3.07(m, 1H); 1.20(d, 3H); 1.09(d, 3H) | 549 |
| 184 | (S)-2-(2-Cyclohexylbenzoylamino)-quinoline-6-carboxylic acid (tert-butylcarbamoyl-phenylmethyl)amide | 569(d, 1H), 3.07(m, 1H); 1.31(s, 9H) | 563 |
| 185 | (S)-2-(2-Cyclohexylbenzoylamino)-quinoline-6-carboxylic acid [(ethylmethylcarbamoyl)-phenylmethyl]amide | 6.10(d, 0.5H); 6.06(d, 0.5H); 3.06(m, 1H); 3.01(s, 1.5H); 2.93(s, 1.5H); 1.15(t, 1.5H); 0.97(t, 1.5) | 549 |
| 186 | (S)-2-(2-Cyclohexylbenzoylamino)-quinoline-6-carboxylic acid [(benzylmethylcarbamoyl)-phenylmethyl]amide | 6.18(d, 0.3H); 6.14(d, 0.7H); 3.07(m, 1H); 2.95(s, 0.9H); 2.89(s, 2.1H) | 611 |
| 187 | 3-(2-{[2-(2-Cyclohexylbenzoylamino)-quinoline-6-carbonyl]amino}-2-phenylacetylamino)-propionic acid benzyl ester | 5.56(d, 1H); 5.05(s, 2H); 3.55(m, 2H); 3.04(m, 1H); 2.56(m, 2H) | 669 |
| 188 | (S)-2-(2-Cyclohexylbenzoylamino)-quinoline-6-carboxylic acid (phenylpyridin-2-yl-methyl)amide | 6.40(d, 1H); 3.08(m, 1H) | 541 |
| 189 | (S)-2-[(4'-tert-Butyl-6-methoxy-biphenyl-2-carbonyl)-amino]-quinoline-6-carboxylic acid(phenyl-pyridin-2-yl-methyl)-amide | 6.36(d, 2H); 3.81(s, 3H); s, 9H) | 622 |
| 190 | (S)-2-[(4'-tert-Butyl-6-methoxy-biphenyl-2-carbonyl)-amino]-quinoline-6-carboxylicacid{[(4-fuoro-benzyl)-methyl-carbamoyl]-phenyl-methyl}-amide | 3.81(s, 3H); 2.90(s, 0.9H); 2.86(s, 1.9H); 1.15(s, 9H) | 710 |
| 191 | (S)-2-[(4'-tert-Butyl-6-methoxy-biphenyl-2-carbonyl)-amino]-quinoline-6-carboxylic acid[(methyl-pyridin-2-ylmethyl-carbamoyl)-phenyl-methyl]-amide | 3.40(s, 3H); 3.03(s, 0.9H); 1.15(s, 9H) | 692 |
| 192 | (S)-2-[(4'-tert-Butyl-6-methoxy-biphenyl-2-carbonyl)-amino]-quinoline-6-carboxylic acid{phenyl-[(pyridin-2-ylmethyl)-carbamoyl]-methyl}-amide | 4.47(m, 2H), 3.83(s, 3H); 1.16(s, 9H) | 678 |
| 193 | (6)-2-[(4'-tert-Butyl-6-methoxy-biphenyl-2-carbonyl)-amino]-quinoline-6-carboxylic acid[(4-fluoro-benzylcarbamoyl)-phenyl-methyl]-amide | 4.42(m, 2H); 3.81(s, 3H); 1.16(3, 9H) | 695 |
| 194 | (S)-2-[(6-Methoxy-4'-methyl-biphenyl-2-carbonyl)-amino]-quinoline-6-carboxylic acid{[(4-fluoro-benzyl)-methyl-carbamoyl]-phenyl-methyl}-amide | 3.77(s, 3H); 2.88(s, 0.9H); 2.86 9s, 1.9H); 2.26(s, 3H) | 667 |
| 195 | (S)-2-[(6-Methyl-4'-trifluoromethyl-biphenyl-2-carbonyl)-amino]-quinoline-6-carboxylic acid[(methyl-pyridin-2-ylmethyl-carbamoyl)-phenyl-methyl]-amide | 6.11(m, 1H); 3.02(s, 1.2H); 3.00(s, 2.8H) | 688 |
| 196 | (S)-2-[(6-Methyl-4'-trifluoromethyl-biphenyl-2-carbonyl)-amino]-quinoline-6-carboxylic acid(phenyl-pyridin-2-yl-methyl)-amide | 6.36(d, 1H); 2.03(s, 3H) | 617 |
| 197 | (R)-2-[(6-Methyl-4'-trifluoromethyl-biphenyl-2-carbonyl)-amino]-quinoline-6-carboxylic acid (1-phenyl-ethyl)-amide | 5.34 dq, 1H); 2.15(s, 3H) | 554 |
| 198 | (S)-2-[(6-Methyl-4'-trifluoromethyl-biphenyl-2-carbonyl)-amino]-quinoline-6-carboxylic acid{[(4-fluoro-benzyl)-methyl- | 6.10(m, 1H); 4.75(m, 2H); | 705 |

TABLE 9(a)-continued

| Ex. No. | Compound Name | Select ¹H NMR signals (CDCl₃) | ESMS (m + 1) |
|---|---|---|---|
|  | carbamoyl]-phenyl-methyl}-amide | 2.90(s, 1.1H); 2.86(s, 2.9H) |  |
| 199 | (R)-2-[(4'-tert-Butyl-6-methyl-biphenyl-2-carbonyl)-amino]-quinoline-6-carboxylic acid(phenyl-pyridin-2-yl-methyl)-amide | 6.35(d, 1H); 2.21(s, 3H); 1.78(s, 9H) | 605 |
| 200 | (R)-2-[(4'-Isopropyl-6-methyl-biphenyl-2-carbonyl)-amino]-quinoline-6-carboxylic acid(phenyl-pyridin-2-yl-methyl)-amide | 6.37(d, 1H); 2.20(s, 3H); 1.10(d, 6H) | 591 |
| 201 | (R)-2-[(6,4'-Dimethyl-biphenyl-2-carbonyl)-amino-quinoline-6-carboxylic acid (phenyl-pyridin-2-yl-methyl)-amide | 6.35(d, 1H); 2.30(s, 3H); 2.18(s, 3H) | 563 |
| 202 | (S)2-[(4'-tert-Butyl-6-methyl-biphenyl-2-carbonyl)-amino]-quinoline-6-carboxylic acid[(methyl-pyridin-2-ylmethyl-carbamoyl)-phenyl-methyl]-amide | 6.12(m, 1H); 4.76(m, 2H); 3.01(s, 1.2H); 2.99(s, 1.8H), 2.19(s, 3H), 1.16(s, 9H) | 676 |
| 203 | (S)-2-[(4'-Isopropyl-6-methyl-biphenyl-2-carbonyl)-amino]-quinoline-6-carboxylic acid[(methyl-pyridin-2-ylmethyl-carbamoyl)-phenyl-methyl]-amide | 6.12(m, 1H); 4.74(m, 2H); 3.02(s, 0.9H); 2.99(s, 2.1H), 2.20(s, 3H), 1.08(d, 6H) | 663 |
| 204 | (S)-2-[(6,4'-Dimethyl-biphenyl-2-carbonyl)-amino]-quinoline-6-carboxylic acid[(methyl-pyridin-2-ylmethyl-carbamoyl)-phenyl-methyl]-amide | 6.14(m, 1H); 4.78(m, 2H); 3.01(s, 1H); 3.00(s, 2H), 2.28(s, 3H), 2.17(s, 3H) | 634 |
| 205 | (S)-2-[(4'-tert-Butyl-6-methyl-biphenyl-2-carbonyl)-amino]-quinoline-6-carboxylic acid{[(4-fluoro-benzyl)-methyl-carbamoyl]-phenyl-methyl}-amide | 6.13(d, 0.25H); 6.08(d, 0.75H); 2.90(s, 0.75H); 2.85(s, 2.5H) | 693 |
| 206 | (S)-2-[(4'-Isopropyl-6-methyl-biphenyl-2-carbonyl)-amino]-quinoline-6-carboxylic acid{[(4-fluoro-benzyl)-methyl-carbamoyl]-phenyl-methyl}-amide | 6.14(d, 0.25H); 6.08(d, 0.75H); 4.6(s, 2H); 2.87(s, 0.75H), 2.85(s, 2.25H), 2.18(s, 3H) | 679 |
| 207 | (S)-2-[(6,4'-Dimethyl-biphenyl-2-carbonyl)-amino]-quinoline-6-carboxylic acid {[(4-fluoro-benzyl)-methyl-carbamoyl]-phenyl-methyl}-amide | 6.05(m, 1H); 4.5(m, 2H); 2.90(s, 1H); 2.86(s, 2H) | 651 |
| 208 | (R)-2-[(4'-tert-Butyl-6-methyl-biphenyl-2-carbonyl)-amino]-quinoline-6-carboxylic acid(1-phenyl-propyl)-amide | 5.11(dt, 1H); 2.21(s, 3H); 1.17(s, 9H) | 556 |
| 209 | 'PF-02406189::(R)-2-[(4'-tert-Butyl-6-methyl-biphenyl-2-carbonyl)-amino]-quinoline-6-carboxylic acid(1-phenyl-ethyl)-amide | 5.37(m, 1H); 2.21(s, 3H); 1.63(d, 3H); 1.17(s, 9H) | 542 |
| 210 | 'PF-02406190:(S)-2-[(4'-tert-Butyl-6-methyl-biphenyl-2-carbonyl)-amino]-quinoline-6-carboxylic acid [(4-fluoro-benzylcarbamoyl)-phenyl-methyl]-amide | 5.82(d, 1H); 4.36(d, 2H); 2.20(s, 1H); 1.17(s, 9H) | 679 |
| 211 | (S)-2-[(6,4'-Dimethyl-biphenyl-2-carbonyl)-amino]-quinoline-6-carboxylic acid{phenyl-[(pyridin-2-ylmethyl)-carbamoyl]-methyl}-amide | 5.78(d, 1H), 4.69(dd, 1H); 4.52(dd, 1.2H); 2.29(s, 3H), 2.17(s, 3H) | 620 |
| 212 | (S)-2-[(6,4'-Dimethyl-biphenyl-2-carbonyl)-amino]-quinoline-6-carboxylic acid[(4-fluoro-benzylcarbamoyl)-phenyl-methyl]-amide | 5.79(d, 1H); 4.36(d, 2H); 2.28(s, 3H), 2.16(s, 3H) | 637 |
| 213 | (S)-2-[(4'-Isopropyl-6-methyl-biphenyl-2-carbonyl)-amino]-quinoline-6-carboxylic acid[(4-fluoro-benzylcarbamoyl)-phenyl-methyl]-amide | 5.71(d, 1H); 4.41(d, 2H); 2.20(s, 3H); 1.11(d, 6H) | 623 |
| 214 | (S)-2-[(4'-Isopropyl-6-methyl-biphenyl-2-carbonyl)-amino]-quinoline-6-carboxylic acid{phenyl-[(pyridin-2-ylmethyl)-carbamoyl]-methyl}-amide | 5.77(d, 1H); 4.65(dd, 1H); 4.50(dd, 1H); 2.21(s, 3H), 1.16(s, 6H) | 648 |
| 215 | (S)-2-[(4'-tert-Butyl-6-methyl-biphenyl-2-carbonyl)-amino]-quinoline-6-carboxylic acid{phenyl-[(pyridin-2-ylmethyl)-carbamoyl]-methyl}-amide | 5.78(d, 1H); 4.66(dd, 1H); 4.50(dd, 1H); 2.21(s, 3H), 1.17(s, 9H) | 662 |

Solid Amorphous Dispersion Formulations

MTPI Dispersion Examples

Formulation Example 1

The following process was used to form a spray-dried solid amorphous dispersion containing 25 wt % the compound of Example 1 ("Compound 1") and 75 wt % HPMCAS-HG (hydroxypropyl methylcellulose acetate succinate, AQOAT-HG, available from Shin Etsu, Tokyo, Japan). First, a spray solution was formed containing 1.25 wt % of Compound 1, 3.75 wt % HPMCAS-HG, and 95 wt % acetone as follows. Compound 1 and acetone were combined in a container and mixed for about 2 hours, allowing the compound to dissolve. Next, HPMCAS-HG was added directly to this mixture, and the mixture stirred for an additional 2 hours. This mixture was then passed through a filter with a screen size of 200 μm, thus forming the spray solution.

The spray solution was pumped using a high-pressure pump to a spray drier (a Niro type XP Portable Spray-Drier with a Liquid-Feed Process Vessel ("PSD-1")), equipped with a pressure nozzle (Spraying Systems Pressure Nozzle and Body) (SK 72-16). The PSD-1 was equipped with a 9-inch chamber extension. The chamber extension was added to the spray drier to increase the vertical length of the drier. The spray drier was also equipped with a 316 stainless steel circular diffuser plate with $\frac{1}{16}$-inch drilled holes, having a 1% open area. This small open area directed the flow of the drying gas to minimize product recirculation within the spray drier. The nozzle sat flush with the diffuser plate during operation. The spray solution was delivered to the nozzle at about 190 g/min at a pressure of 140 psig. The pump was followed by a pulsation dampener to minimize pulsation at the nozzle. Drying gas (e.g., nitrogen) was delivered to the diffuser plate at a flow rate of 1800 g/min, and an inlet temperature of 105° C. The evaporated solvent and wet drying gas exited the spray drier at a temperature of 45° C. The spray-dried solid amorphous dispersion formed by this process was collected in a cyclone, then post-dried using a Gruenberg single-pass convection tray drier operating at 40° C. for 4 hours. The properties of the dispersion after secondary drying were as follows:

Formulation Table 1

| Bulk Properties (After Secondary Drying) | Value |
|---|---|
| Bulk Specific Volume (cc/g) | 4.9 |
| Tapped Specific Volume (cc/g) | 2.9 |
| Hausner Ratio | 1.7 |
| Mean Particle Diameter (μm) | 35 |
| $D_{10}$, $D_{50}$, $D_{90}$ (μm) | 12, 31, 62 |
| Span $(D_{90}-D_{10})/D_{50}$ | 1.6 |
| Residual Acetone (Before Secondary Drying) | 2.1% |

* 10 vol % of the particles have a diameter that is smaller than $D_{10}$; 50 vol % of the particles have a diameter that is smaller than $D_{50}$, and 90 vol % of the particles have a diameter that is smaller than $D_{90}$.

Formulation Example 2

A solid amorphous dispersion of 25 wt % of the compound of Example 1 ("Compound 1") and 75 wt % HPMCAS-HG was also prepared using a "mini" spray-drier. A spray solution was prepared by dissolving 25 mg Compound 1 and 75 mg HPMCAS in 20 g of acetone. The mini spray-drier consisted of an atomizer in the top cap of a vertically oriented 11-cm diameter stainless steel pipe. The atomizer was a two-fluid nozzle (Spraying Systems Co. 1650 fluid cap and 64 air cap), where the atomizing gas was nitrogen delivered to the nozzle at 70° C. and a flow rate of 15 gm/min, and the solution to be spray dried was delivered to the nozzle at room temperature and a flow rate of 1.3 mL/min using a syringe pump. Filter paper with a supporting screen was clamped to the bottom end of the pipe to collect the solid spray-dried material and allow the nitrogen and evaporated solvent to escape.

Formulation Example 3

The following process was used to form a spray-dried solid amorphous dispersion containing 25 wt % of the compound of Example 135 ("Compound 135") and 75 wt % HPMCAS-HG. First, a spray solution was formed containing 9.89 g Compound 135, 29.67 g HPMCAS-HG, and 525.58 g acetone. The spray solution was added to a tank and pressurized using compressed nitrogen to pass the solution through a pressure-swirl atomizer (Schlick #2 pressure nozzle) located in a spray-drying chamber.

The spray-drying chamber consisted of three sections: a top section, a straight-side section, and a cone section. The top section had a diameter of 10.875 inches (27.6 cm), and was equipped with a drying-gas inlet and a spray-solution inlet. The top section also contained an upper perforated plate and a lower perforated plate for dispersing the drying gas within the spray-drying chamber. The upper perforated plate extended across the diameter of the top section and formed an upper chamber in the top section of the spray-drying chamber. The upper perforated plate contained 0.0625-inch (0.16 cm) diameter holes at a uniform spacing of 0.5 inches (1.27-cm). The lower perforated plate extended across the diameter of the top section of the spray-drying chamber and formed a lower chamber of the top section of the spray-drying chamber. The lower perforated plate contained 0.0625-inch (0.16 cm) diameter holes at a uniform spacing of 0.25 inches (0.64-cm). The drying gas entered the upper chamber in the top section through the drying-gas inlet and then passed through the holes in the upper perforated plate. The drying gas then entered the lower chamber and passed through the holes in the lower perforated plate. The drying gas then entered the straight side section of the spray-drying chamber.

The spray solution was fed to the spray-drying chamber through the spray-solution inlet. The pressure-swirl atomizer was mounted flush with the bottom of the lower perforated plate. The spray solution was then sprayed into the straight-side section of the spray-drying chamber. The straight-side section had a diameter of 10.5 inches (26.7 cm) and a length of 31.75 inches (80.6 cm). The flow rate of drying gas and spray solution were selected such that the atomized spray solution was sufficiently dry by the time it reached the walls of the straight-side section that it did not stick to the walls.

The so-formed solid particles were collected in the cone section of the spray-drying chamber. The cone section had an angle of 58 degrees. The diameter of the cone section at the top was 10.5 inches (26.7 cm), and the distance from the top of the cone section to the bottom was 8.625 inches (21.9 cm). At the bottom of the cone section was a 1-inch (2.54-cm) diameter outlet port.

The spray-dried particles, evaporated solvent, and drying gas were removed from the spray-drying chamber through the outlet port and sent to a cyclone separator where the spray-dried particles were collected. The evaporated solvent and drying gas were then sent to a filter for removal of any remaining particles before discharge.

To form the spray-dried dispersion, the spray solution was delivered to the nozzle at a pressure of about 140 psi and at a flow rate of about 37 g/min. Drying gas (nitrogen) entered the spray-drying chamber at a flow of about 425 g/min and an inlet temperature of about 111° C. The evaporated solvent and drying gas exited the spray drier at a temperature of 45° C. The resulting solid amorphous dispersion was collected in a cyclone.

Formulation Example 4

A solid amorphous dispersion of 25 wt % of the compound of Example 135 ("Compound 135") and 75 wt % HPMCAS-HG was also prepared using a "mini" spray-drier using the procedures described for the dispersion of Formulation Example 2 with the following exceptions. The spray solution was prepared by dissolving 20 mg Compound 135 and 60 mg HPMCAS in 8 g of acetone. The atomizing gas was nitrogen delivered to the nozzle at 70° C. and a flow rate of about 8 gm/min, and the solution to be spray dried was delivered to the nozzle at room temperature and a flow rate of 0.65 mL/min using a syringe pump. Filter paper with a supporting screen was clamped to the bottom end of the pipe to collect the solid spray-dried material and allow the nitrogen and evaporated solvent to escape.

Formulation Example 5

A spray-dried solid amorphous dispersion containing 25 wt % of the compound of Example 114 ("Compound 114") and 75 wt % HPMCAS-HG was formed using the procedures outlined in Fromulation Example 3 with the following exceptions. The spray solution was formed containing 10.897 g Compound 114, 32.7 g HPMCAS, and 579.26 g acetone. The spray solution was added to a tank and pressurized using compressed nitrogen to pass the solution through a pressure-swirl atomizer (Schlick #2 pressure nozzle) located in the spray-drying chamber, as described above for Formulation Example 3.

To form the spray-dried solid amorphous, the spray solution was delivered to the nozzle at a pressure of about 150 psi, and at a flow rate of about 38 g/min. Drying gas (nitrogen) entered the spray-drying chamber at a flow of about 425 g/min and an inlet temperature of about 115° C. The evaporated solvent and drying gas exited the spray drier at a temperature of 45° C. The resulting solid amorphous dispersion was collected in a cyclone.

Formulation Example 6

A solid amorphous dispersion of 25 wt % the compound of Example 114 ("Compound 114") and 75 wt % HPMCAS-HG was also prepared using a "mini" spray-drier using the procedures outlined for Example 2 with the following exceptions. A spray solution was prepared by dissolving 20 mg Compound 114 and 60 mg HPMCAS in 8 g of acetone. The atomizing gas was nitrogen delivered to the nozzle at 70° C. and a flow rate of about 8 gm/min, and the solution to be spray dried was delivered to the nozzle at room temperature and a flow rate of 0.65 mL/min using a syringe pump. Filter paper with a supporting screen was clamped to the bottom end of the pipe to collect the solid spray-dried material and allow the nitrogen and evaporated solvent to escape.

Biological Assays

The utility of the compounds of the present invention as pharmaceutically active agents in the treatment of metabolic diseases (such as are detailed herein) in animals, particularly mammals (e.g. humans), is demonstrated by the activity of the compounds of the present invention in conventional assays and the in vitro and in vivo assays described below. Such assays also provide a means whereby the activities of the compounds of the present invention can be compared with the activities of other known compounds. The results of these comparisons are useful for determining dosage levels. All of the compounds listed in the Examples section above were tested in either the Apo-B secretion inhibition assay or the MTP (canine) inhibition assay described below, and the $IC_{50}$ values for these compounds were found to be less than 200 nM under the conditions of those assays.

Food Intake

Healthy, young adult (1 to 3 years of age) male and female beagles (Marshall Farms, North Rose, New York, N.Y. 14516) weighing 13-19 kg at the start of the treatment period are employed as test subjects.

The test compound is provided as a powder. The dosing solution, administered by oral gavage, is provided employing a Miglyol®/cremaphor/water 20/5/75 solution as the test vehicle. Miglyol® IS available from Condea Vista Co., Cranford, N.J. The dosing solution is prepared at 0.5 to 2 mg/mL activity so that 0.5 mL is delivered per kg of body weight at dosages of 0.25 to 1 mg/kg. Following a seven-day acclimation period, a four- to seven-day evaluation study is effected.

The study consists of three groups of animals containing 2 male and 2 female dogs each. Each group of four animals is randomly assigned to receive 0.25, 0.5 or 1 mg/kg test compound. On Days 0 to 3 or 6, each dog receives the dosing solution administered as a single dose at Time 0 on each dosing day via a feeding tube. This is followed by a 10 mL water rinse to ensure total delivery of dosing solution. Each test animal is permitted ad libitum access to water and IAMS Mini-Chunkso (The Iams Company, P.O. Box 14597, Dayton, Ohio) dry food each day during the study and approximately 0.5 to 1 hour post-dose.

Reduction in food intake is quantitated by weighing individual food bowls each day prior to feeding and at the end of each 24-hour consumption period during the acclimation period and again during the treatment period. The difference between the weight of the full bowl prior to feeding and the weight of the bowl and amount of food remaining at the end of the 24-hour consumption period represents the reduction in food intake attributable to the test compound.

APO B Secretion Inhibition

The ability of the compounds of the present invention to inhibit the secretion of apo B can be determined using the following cell-based assay, which measures the secretion of apo B in HepG2 cells.

HepG2 cells (ATCC, HB-8065, Manassas, Va.) are grown in Dulbecco's Modified Eagles Medium plus 10% fetal bovine serum (Growth medium; Gibco, Grand Island, N.Y.)

in 96-well culture plates in a humidified atmosphere containing 5% carbon dioxide until they are approximately 70% confluent. Test compounds are dissolved at 10 mM in dimethyl sulfoxide (DMSO). From this stock, the initial dose concentration is prepared in 70% EtOH and subsequent sedal dilutions made in 70% EtOH with DMSO at a concentration equivalent to the initial dilution. Dilutions of test compounds are prepared at 100× the desired final concentration and are added in triplicate to separate wells of a 96-well culture plate containing HepG2 cells. Forty hours later, growth medium is collected and assayed by specific enzyme-linked immunosorbent assay (ELISA) for Apo B. Inhibitors are identified as compounds that decrease Apo B secretion into the medium. The ELISA assay for Apo B is performed as follows: Polyclonal antibody against human Apo B (Chemicon, Temecula, Calif.) is diluted 1:1000 in carbonate-bicarbonate buffer (Pierce, Rockford, Ill.) and 100 µL are added to each well of a 96-well plate (NUNC Maxisorb, Rochester, N.Y.). After 5 hours incubation at room temperature, the antibody solution is removed and wells are washed four times with phosphate buffered saline (PBS)/0.05% Tween® 20 (Tween® 20 is available from Cayman Chemical Co., Ann Arbor Mich.). Non-specific sites on the plastic are blocked by incubating wells for 1 to 1.5 hours in a solution of 0.5% (w/v) bovine serum albumin (BSA), 0.1% Tween® 20 made in PBS. One hundred microliters (100 µL) of a 1:20 dilution of growth medium from the HepG2 cells (made in 0.004% Tween® 20/1% BSA in PBS) are added to each well and incubated for 3 hours at room temperature. Wells are aspirated and washed four times (0.05% Tween® 20 in PBS) prior to adding 100 µL of a 1/1000 dilution (~5 ug/mL) of the secondary antibody, mouse anti-human Apo B (Chemicon, Temecula, Calif.). After 2 hours incubation at room temperature, this solution is aspirated and the wells are again washed 4 times as above. One hundred microliters (100 µL) of a 1:10,000 dilution (in PBS/1% BSA/0.1% Tween® 20) of peroxidase-conjugated affinpure goat anti-mouse IgG (H+L) (Jackson ImmunoResearch Laboratories, Bar Harbor, Me.)) are then added to each well and incubated for 1 hour at room temperature. After aspirating, the wells are washed 4 times as above and 50 µl of 1-step Ultra TMB (tetramethylbenzidine) ELISA reagent (Pierce, Rockford, Ill.) are added to each well and incubated for 5 minutes. The reaction is stopped by the addition of 50 µL of 2M $H_2SO_4$ and absorbance of each well is read at 450 nm. Percent inhibition is calculated using absorbance from vehicle-treated supernatants minus the absorbance from media alone as the total or 100% value. The percent inhibition at each concentration of test compound is imported into GraphPad Prism software and $IC_{50}$ values are determined.

MTP (Canine) Inhibition

This assay determines the ability of a compound to inhibit triglyceride transfer catalyzed by canine MTP. This assay is based on measuring the transfer rate of $^{14}C$ from a donor liposome to an acceptor liposome (which is labeled with $^3H$).

(A). Canine Hepatic Microsome Isolation:

Canine microsomes are first isolated from canine liver by thawing frozen liver on ice and rinsing several times with 0.25 M sucrose. A 50% liver homogenate (w/v) is made in 0.25 M sucrose. The homogenate is diluted 1:1 with 0.25 M sucrose, and centrifuged at 10,000 g at 4° C. for 20 minutes. The supernatant is saved. The pellet is re-suspended in a minimal volume of 0.25 M sucrose and re-centrifuged at 10,000 g for 20 minutes at 4° C. The supernatants are combined and centrifuged at 105,000 g for 75 minutes at 4° C. The supernatant is discarded and the resulting microsomal pellet is saved. The microsomal pellet is re-suspended in a minimum volume of 0.25 M sucrose and diluted to 3 mL per gram liver weight in 0.15M Tris-HCl, pH=8.0. The resulting suspension is divided into 12 tubes and centrifuged at 105,000 g for 75 minutes. The resulting microsomal pellets are stored at −80° C. until needed.

MTP is isolated by thawing the microsomal pellet tube and suspending it in 12 mL/tube of cold 50 mM Tris-HCl, 50 mM KCl, 2 mM MgCl pH=7.4, and slowly adding 1.2 mL of a 0.54% deoxycholate pH=7.4 solution. After a 30-minute incubation on ice with gentle mixing, the solution is centrifuged at 105,000 g for 75 minutes at 4° C. The supernatant containing soluble MTP, is dialyzed for 2-3 days with 5 changes of assay buffer (15.0 mM Tris-HCl, 40 mM NaCl, 1 mM EDTA, 0.02% NaN3 pH=7.4).

(B). MTP Activity Assay Reagents:

Donor liposomes are created by adding 447 µM egg phosphatidylcholine (68 µl/20 mLs), 83 µM bovine heart cardiolipin (169 µl/20 mLs) and 0.91 µM [$^{14}C$]triolein (110 Ci/mol) (20 µl/20 mLs). The lipids are available in chloroform and are first dried under nitrogen and then hydrated in assay buffer to the volume needed. To create liposomes, lipids are sonicated for ~7 minutes. Lipids are centrifuged at 105,000 g for 2 hours and liposomes are harvested by removing the top ~80% of supernatant into separate tube.

Acceptor liposomes are created by adding 1.33 mM egg phosphatidylcholine (404 µl/40 mLs), 2.6 µM triolein (100 µl/40 mLs) and 0.5 nM [$^3H$]egg phosphatidylcholine (50 Ci/mol) (10 µl/40 mLs). The lipids are available in chloroform and are first dried under nitrogen and then hydrated in assay buffer to the volume needed. To create liposomes, lipids are sonicated for ~20 minutes. Lipids are centrifuged at 105,000 g for 2 hours and are harvested by removing the top ~80% of supernatant into separate tube.

(C). MTP In Vitro Lipid Transfer Inhibition Assay:

Appropriately diluted drug or control samples in 100 µl assay buffer containing 5% BSA are added to reaction tubes containing assay buffer, 50 µl donor liposomes, 100 µl acceptor liposomes, and partially purified liver MTP. The tubes are vortexed and incubated on a tube shaker for 1 hour at 37° C. to allow lipid transfer reaction to occur. Donor liposomes are precipitated by adding 300 µl of a 50% (w/v) DEAE cellulose suspension in assay buffer to each tube. The tubes are centrifuged at ~1000 rpm to pellet resin. 400 µl of supernatant is transferred into a scintillation vial with scintillation fluid and DPM counts for both [$^3H$] and [$^{14}C$] are determined. Triolein transfer is calculated by comparing the amount of [$^{14}C$] and [$^3H$] remaining in the supernatant to [$^{14}C$] and [$^3H$] in the original donor and acceptor liposomes, respectively. % Triolein Transfer=([$^{14}C$]supernatant/[$^{14}C$] donor)×([$^3H$]acceptor/[$^3H$]supernatant)×100 $IC_{50}$ values are obtained using standard methods and first order kinetic calculations.

Fat Absorption Inhibition

Healthy female CF1 mice (Charles River) weighing 18-20 grams upon arrival are employed as test subjects. The mice are housed in groups of 10 in standard caging, and are allowed to acclimate for one week prior to testing. Mice are fasted overnight in a separate procedure room prior to testing. Each treatment group typically consists of 5 mice.

The test compounds are preferably provided as a powder in a glass vial. The dosing solution (0.10 ml/25 g body weight) administered by oral gavage consists of an emulsion of Miglyol® 812 (20%), Cremaphor® (5%) and water (75%). An appropriate volume of Miglyol® (available from Condea Vista Co., Cranford, N.J.) is first added to the test compound, and the vial is vortexed for approximately 1 minute. The appropriate volume of Cremaphor is then added, and the vial is again vortexed as before. The appropriate volume of water is added, and an emulsion is formed by vortexing and briefly sonicating.

Hamster liquid diet (Bioserve F0739) (dose volume 0.5 ml/25 g body weight) is prepared by adding (for every 10 mL needed) 2.5 grams liquid diet powder, 10 mL water and 5 microcuries glycerol-$^3$H-trioleate (Amersham TRA191) to a laboratory blender. The mixture is then blended at high speed for approximately 1 minute. The liquid diet is stored at 4° C. until needed. Sample tubes are weighed (Falcon 15 ml polypropylene conical). Three milliliters of 2.5N KOH is added to each tube.

Following overnight fasting, each mouse is dosed (see above volumes) with test compound followed immediately by liquid diet. Positive (a known potent MTP inhibitor) and negative control groups (vehicle) are included in each assay. One scintillation vial is sham-dosed every 30 mice in order to determine the activity of the initial bolus.

At two hours post dose the mice are euthanized by carbon dioxide inhalation, the abdominal cavity opened, and the small intestines removed and placed in the KOH conical tube. Each tube is then weighed. Tubes containing intestines are then placed in a 75° C. water bath for 1.5-2 hours. Following saponification, the tubes are vortexed and 200 µL saponate placed in a 20 mL liquid scintillation vial. Samples are decolorized (for 30 minutes) by adding 200 µL of 30% (w/w) hydrogen peroxide. Each sample is neutralized by the addition of 200 µL of 3N HCL. Ten milliliters of Ready Safe® (Beckman) liquid scintillation fluid are added and the samples are counted on a Beckman Coulter LS 6500 scintillation system.

The calculations are carried out as follows:

weight of saponate=weight of tube (KOH+intestine)−weight of empty tube saponate fraction=0.22/saponate weight (density of the saponate=1.1 g/mL; therefore the weight of the aliquot is equal to 0.22 g)

total DPM for the entire intestine=DPM of sample/saponate fraction

The initial bolus DPM is calculated by averaging the counts from the sham-dosed scintillation vials.

The fraction of bolus recovered from the intestine (percent recovery)=total DPM/bolus count.

Percent recovery from each test group=average of percent recovery from each mouse.

Interpretation of results:

To compare efficacy of test compounds, an $ED_{25}$ for intestinal fat absorption is calculated. The (average) percent triglyceride recovery (percent unabsorbed and remaining in the intestine) of the vehicle control group is adjusted to equal 0%, and the (average) percent recovery of the compound control group is adjusted to equal 100%. The same calculations are applied to the percent recovery values obtained for test compounds and an adjusted percent recovery is obtained (% recovery of the test sample−% recovery of vehicle control group/(% recovery of positive control group−% recovery of vehicle control group)). An $ED_{25}$ is then calculated by plotting a graph of compound concentration vs. adjusted percent recovery.

Serum Triglyceride Lowering

Healthy female CF1 mice (Charles River) weighing 18-20 grams upon arrival are employed as test subjects. The mice are housed in groups of 10 in standard caging, and were allowed to acclimate for one week prior to testing. Mice are fasted overnight in a separate procedure room prior to testing. Each treatment group typically consists of 10 mice.

The test compound is preferably provided as a powder in a glass vial. The dosing solution (0.250 mL/25 g body weight) administered by oral gavage consists of an emulsion of Miglyol® 812 (40%), Cremaphor® (10%) and water (50%). An appropriate volume of Miglyol® (available from Condea Vista Co., Cranford, N.J.) is first added to the test compound, and the vial vortexed for approximately 1 minute. Next, the appropriate volume of Cremaphor is added, and the vial again vortexed as previously. The appropriate volume of water is then added and an emulsion is formed by vortexing and briefly sonicating.

Following overnight fasting, each mouse is dosed (see above volumes) with test compound. At 1-hour post dose the mice are euthanized by carbon dioxide inhalation and blood collected for triglyceride quantitation.

Serum triglyceride values are quantitated using a colorimetric endpoint assay (Wako Triglyceride E kit # 432-4021) on a Spectra Max 250 plate reader with Softmax Pro software. All samples are run in duplicate.

For comparison of triglyceride values, the percent change from control is calculated. The average triglyceride value of the test compound group is divided by the average triglyceride value of the vehicle group, multiplied by 100 and then subtracted from 100%. The $ED_{25}$ value is then calculated by plotting a graph of compound concentration versus percent change from control.

The relative values of the $ED_{25}$ for triglyceride lowering and the $ED_{25}$ for inhibition of intestinal fat absorption are used as a means to compare selectivity of the test compounds.

The invention claimed is:

1. The compound of the formula

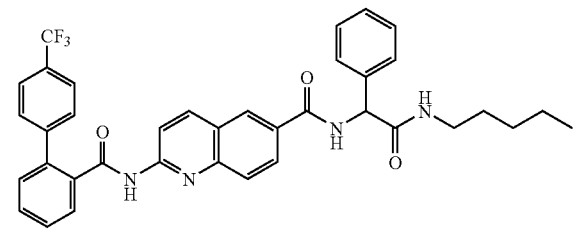

or a pharmaceutically acceptable salt thereof.

2. The compound (S)-2-[(4'-trifluoromethyl-biphenyl-2-carbonyl)-amino]-quinoline-6-carboxylic acid (pentylcarbamoyl-phenyl-methyl)-amide or a pharmaceutically acceptable salt thereof.

3. A pharmaceutical composition which comprises a compound of claim 2 or a pharmaceutically acceptable salt thereof; and a pharmaceutically acceptable excipient, diluent or carrier.

4. The pharmaceutical composition of claim 3 which comprises a therapeutically effective amount of said compound or pharmaceutically acceptable salt thereof; and a pharmaceutically acceptable excipient, diluent or carrier.

5. The composition of claim 3 further comprising at least one additional pharmaceutical agent where said additional pharmaceutical agent is an antihypertensive agent, an anti-inflammatory agent, a lipid-lowering agent, a cholesterol-lowering agent, an antidiabetes agent or an anti-obesity agent.

6. Crystalline Form A of (S)-2-[(4'-trifluoromethyl-biphenyl-2-carbonyl)-amino]-quinoline-6-carboxylic acid (pentylcarbamoyl-phenyl-methyl)-amide having an X-ray powder diffraction pattern having peaks at 2-theta values substantially the same as the 2-theta values for at least ten of the peaks of highest intensity in the X-ray powder diffraction pattern shown in FIG. 1.

* * * * *

UNITED STATES PATENT AND TRADEMARK OFFICE
CERTIFICATE OF CORRECTION

PATENT NO.         : 7,368,573 B2                                    Page 1 of 1
APPLICATION NO. : 11/424488
DATED              : May 6, 2008
INVENTOR(S)        : Peter Bertinato et al.

It is certified that error appears in the above-identified patent and that said Letters Patent is hereby corrected as shown below:

On the title page item (54) and Col. 1, line 1, please replace the current title of this application which reads "TRIAMIDE-SUBSTITUTED HETEROBICYCLIC COMPOUNDS" with --SUBSTITUTED QUINOLINE COMPOUNDS--.

Signed and Sealed this

Nineteenth Day of August, 2008

JON W. DUDAS
*Director of the United States Patent and Trademark Office*